(12) United States Patent
Katsura

(10) Patent No.: US 10,241,031 B2
(45) Date of Patent: Mar. 26, 2019

(54) MEASURING DEVICE AND MEASURING METHOD

(71) Applicant: OSAKA UNIVERSITY, Osaka (JP)

(72) Inventor: Makoto Katsura, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 43 days.

(21) Appl. No.: 15/324,160

(22) PCT Filed: Jul. 1, 2015

(86) PCT No.: PCT/JP2015/069026
§ 371 (c)(1),
(2) Date: Jan. 5, 2017

(87) PCT Pub. No.: WO2016/006515
PCT Pub. Date: Jan. 14, 2016

(65) Prior Publication Data
US 2017/0160190 A1 Jun. 8, 2017

(30) Foreign Application Priority Data
Jul. 8, 2014 (JP) .................. 2014-140698

(51) Int. Cl.
*G01N 21/27* (2006.01)
*G01R 19/00* (2006.01)
(Continued)

(52) U.S. Cl.
CPC ....... *G01N 21/274* (2013.01); *G01B 9/02083* (2013.01); *G01D 3/022* (2013.01);
(Continued)

(58) Field of Classification Search
CPC .................................................. G01N 21/274
(Continued)

(56) References Cited

U.S. PATENT DOCUMENTS 6,147,762 A 11/2000 Haschberger et al.
6,911,925 B1 6/2005 Slavin
(Continued)

FOREIGN PATENT DOCUMENTS

DE 101 63 504 A1 7/2003
EP 1 647 810 A1 4/2006
(Continued)

OTHER PUBLICATIONS

The extended European search report issued by the European Patent Office dated Jan. 31, 2018, which corresponds to EP15819573.5-1022 and is related to U.S. Appl. No. 15/324,160.

(Continued)

*Primary Examiner* — Ricky Ngon
(74) *Attorney, Agent, or Firm* — Studebaker & Brackett PC

(57) ABSTRACT

A measuring device (1) includes a first signal generation section (3) and a first removal section (5). The first signal generation section (3) generates a first source signal (x1(t)) including a fundamental and a plurality of harmonics based on a first physical quantity (p1) and a second physical quantity (p2). The first removal section (5) removes some or all of the harmonics from the first source signal (x1(t)). The first source signal (x1(t)) is a periodic signal, and one period of the first source signal (x1(t)) includes a first signal (p1), a second signal (p2), and a reference signal (pr). The first signal (p1) has a first duration (w1) and indicates the first physical quantity (p1). The second signal (p2) has a second duration (w2) and indicates the second physical quantity (p2). The reference signal (pr) has a third duration (w3) and indicates the reference physical quantity (pr).

15 Claims, 29 Drawing Sheets

(51) Int. Cl.
   *G01B 9/02* (2006.01)
   *G01J 3/28* (2006.01)
   *G02B 6/28* (2006.01)
   *G02F 1/35* (2006.01)
   *G02F 1/37* (2006.01)
   *G01D 3/02* (2006.01)

(52) U.S. Cl.
   CPC ............... *G01J 3/28* (2013.01); *G01R 19/00* (2013.01); *G02B 6/28* (2013.01); *G02F 1/353* (2013.01); *G02F 1/37* (2013.01); *G01J 2003/2843* (2013.01); *G01J 2003/2869* (2013.01)

(58) Field of Classification Search
   USPC ....................................................... 702/127
   See application file for complete search history.

(56) References Cited

U.S. PATENT DOCUMENTS

| | | | |
|---|---|---|---|
| 7,286,215 B2 | 10/2007 | Imura | |
| 2004/0118995 A1 | 6/2004 | Curbelo | |
| 2005/0128475 A1 | 6/2005 | Imura | |
| 2007/0222979 A1* | 9/2007 | Van Der Laan | G01N 21/278 356/243.1 |
| 2011/0266987 A1* | 11/2011 | Markunas | H02P 21/18 318/400.24 |

FOREIGN PATENT DOCUMENTS

| | | | |
|---|---|---|---|
| JP | H07-146756 A | 6/1995 | |
| JP | 2002-174551 A | 6/2002 | |
| JP | 2003-185498 A | 7/2003 | |
| JP | 2005-156242 A | 6/2005 | |
| JP | 2005-295542 A | 10/2005 | |
| JP | 2009-092447 A | 4/2009 | |

OTHER PUBLICATIONS

International Search Report issued in PCT/JP2015/069026; dated Sep. 29, 2015.
Kester et al.; Analog-Digital Conversion; Chapter 5 Testing Data Converters; 5.1 Testing DACS; Analog Devices Inc. Engineer; pp. 5.1-5.92.
Early, M.D. et al.; "A Simple Build-Up Method for the DC Voltage Scale of a Source"; IEEE Transactions on Instrumentation and Measurement; vol. 62, No. 6; Jun. 2013; pp. 1600-1607.
Francis; "Measuring Photometric Accuracy Using the Double Aperture Method"; Agilent Technologies; 1993; pp. 1-6.
Monteiro et al.; "Intrinsically Stable Light Source at Telecom Wavelengths"; Applied Physics Letters 103, 051109; 2013; pp. 051109-1 to 051109-4.
Salzberg et al.; "An ultra-stable non-coherent light source for optical measurements in neuroscience and cell physiology"; Journal of Neuroscience Methods 141; 2005; pp. 165-169.
Upstone; "Ultraviolet/Visible Light Absorption Spectrophotometry in Clinical Chemistry"; Encyclopedia of Analytical Chemistry; pp. 1699-1714.
Daqarta—Data AcQuisition and Real-Time Analysis; "Sound Card External DC-to-AC Modulator" (http://www.daqarta.com/dw_ggoo.htm); pp. 1-4.
Brom et al.; "Voltage linearity measurements using a binary Josephson system"; Measurement Science and Technology 18; 2007; pp. 3316-3320.
"NI-Mcal Calibration Methodology Improves Measurement Accuracy"; National Instruments; Oct. 8, 2015; (http://www.ni.com/whitepaper/3688/en/); pp. 1-3.
Hamamatsu Photonics; "MPPC (multi-pixel photon counters)"; (https://www.hamamatsu.com/jp/en/4004.html); pp. 1-2.
Hobbs; "Reaching the Shot Noise Limit for $10"; Optics & Photonics News; Apr. 1991; pp. 17-23.

* cited by examiner

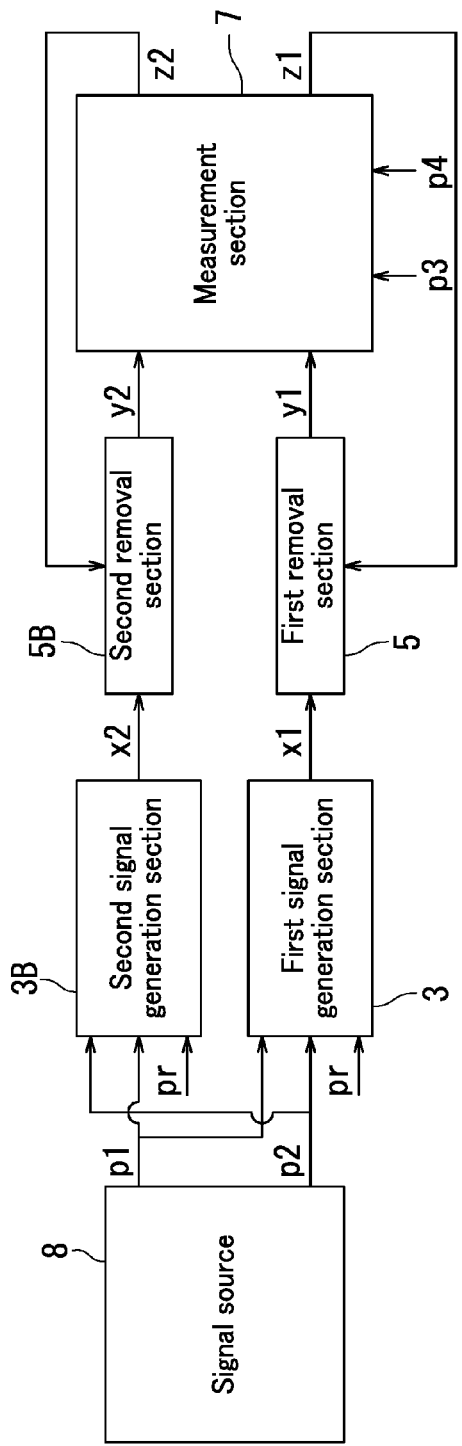
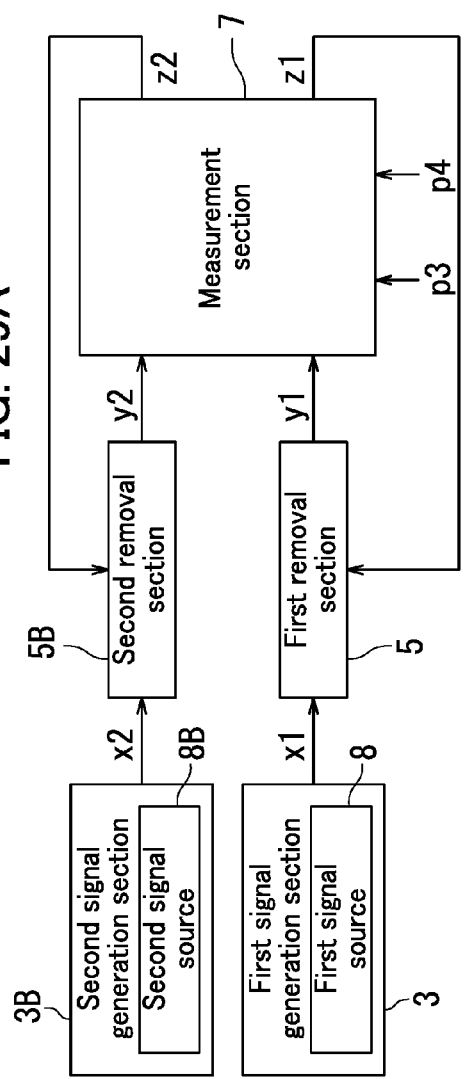
FIG. 29A
FIG. 29B

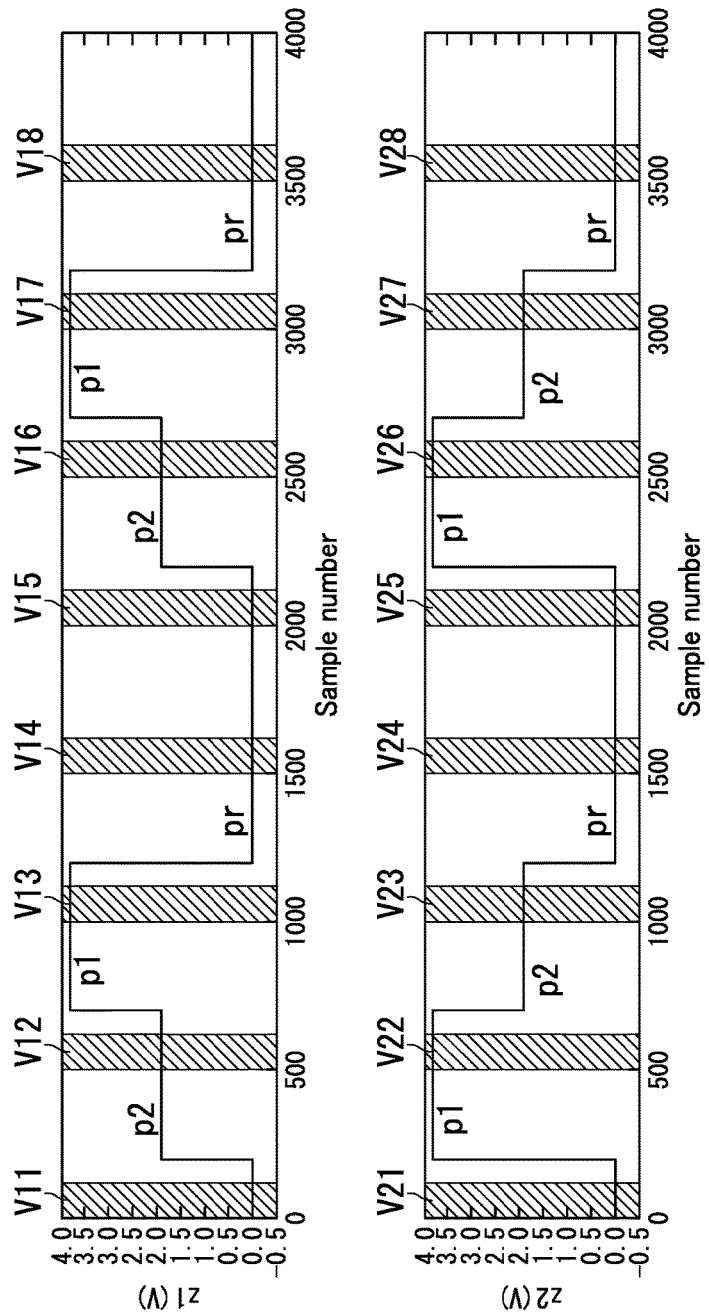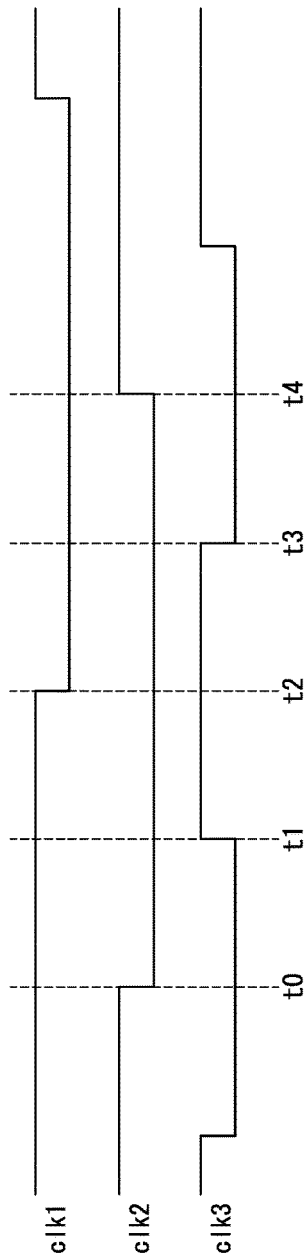
FIG. 33A  FIG. 33B  FIG. 33C  FIG. 33D  FIG. 33E

MEASURING DEVICE AND MEASURING METHOD

TECHNICAL FIELD

The present invention relates to measuring devices and measuring methods.

BACKGROUND ART

In general optical measurement such as spectroscopic measurement and voltage measurement, a ratio between a physical quantity x0 and a physical quantity x1 is determined. The spectroscopic measurement for example refers to measurement of wavelength dependency of optical properties of a measurement target sample through determination of a ratio between an intensity (physical quantity x1) of light that has interacted with the sample (typically, light transmitted through the sample) and an intensity (physical quantity x0) of light that has not interacted with the sample. The voltage measurement for example refers to measurement of a ratio between a reference voltage (physical quantity x0) and a measurement voltage (physical quantity x1).

Consider now the case where temporal variation of the physical quantity x0 and the physical quantity x1 is negligible as against the time required for the measurement, that is, the case where a random error can be reduced by any amount by averaging. When a ratio between the physical quantity x0 and the physical quantity x1 is to be determined precisely, improvement of precision of the measurement may be difficult due to non-linearity of a measuring device, that is, non-linearity of a relationship between measured amounts and measurement results. That is, measurement results include a non-linearity error. The non-linearity error refers to an error that occurs due to non-linearity of the measuring device.

Generally, multipoint calibration is performed in order to reduce influence of non-linearity of the measuring device. Regarding optical measurement, for example a light measuring apparatus described in Patent Literature 1 performs multipoint calibration. Specifically, the light measuring apparatus includes a calculation controlling circuit, a light receiving sensor array, and correction light emitting diodes (LEDs). The correction LEDs irradiate light onto the light receiving sensor array. The calculation controlling circuit calculates correction values at a plurality of known illuminance levels based on sensor output levels expected at the respective illuminance levels and actual sensor output levels while successively turning the correction LEDs on at the illuminance levels. At the time of an actual light measurement, the calculation controlling circuit corrects each sensor output level using a corresponding correction value. As a result, influence of non-linearity of the measuring apparatus is reduced. Regarding voltage measurement, for example multipoint calibration of a voltage ratio is performed by a voltage source including a Josephson device.

CITATION LIST

Patent Literature

[Patent Literature 1]
Japanese Patent Application Laid-Open Publication No. 2005-156242

SUMMARY OF INVENTION

Technical Problem

However, in order to reduce influence of non-linearity by multipoint calibration, a standard is needed that has linearity comparable to or higher than linearity desired to be achieved. It is technically difficult to prepare a standard having high linearity at least in spectroscopic measurement and voltage measurement. Multipoint calibration to a precision of for example 10 parts per million (ppm) in spectroscopic measurement or multipoint calibration to a precision of for example 10 parts per billion (ppb) in voltage measurement involves complicated procedures, takes significant time, and requires large-scale equipment.

The present invention has been achieved in consideration of the above problems and an objective thereof is to provide a measuring device and a measuring method that allow easy reduction of influence of non-linearity on measurement results.

Solution to Problem

A measuring device according to a first aspect of the present invention includes a first signal generation section and a first removal section. The first signal generation section generates a first source signal including a fundamental and a plurality of harmonics based on a first physical quantity and a second physical quantity. The first removal section removes some or all of the plurality of harmonics from the first source signal.

Preferably, in the measuring device according to the present invention, the first source signal is a periodic signal. Preferably, one period of the first source signal includes a first signal having a first duration and indicating the first physical quantity, a second signal having a second duration and indicating the second physical quantity, and a reference signal having a third duration and indicating a reference physical quantity.

Preferably, the measuring device according to the present invention further includes a measurement section, and the first removal section includes a first summing section, a harmonic generation section, a first Fourier transform section, and a first control section. The first summing section sums the first source signal and a harmonic signal having the same frequency as a removal target harmonic among the plurality of harmonics to output a first summed signal. The measurement section outputs the first summed signal in analog form as a first measurement signal in digital form. The harmonic generation section generates the harmonic signal. The first Fourier transform section calculates a plurality of harmonics included in the first measurement signal. The first control section causes the harmonic generation section to adjust either or both of an amplitude and a phase of the harmonic signal so that a harmonic that matches the removal target harmonic is removed from the first measurement signal.

Preferably, in the measuring device according to the present invention, each of the first physical quantity and the second physical quantity is a voltage, and each of the first source signal and the harmonic signal is an electric signal. Preferably, the measurement section includes an analog-digital conversion section. The analog-digital conversion section converts the first summed signal being an analog signal to a digital signal and outputs the digital signal as the first measurement signal.

Preferably, in the measuring device according to the present invention, each of the first physical quantity and the second physical quantity is an optical intensity, and each of the first source signal and the harmonic signal is an optical signal. Preferably, the measurement section includes a photoelectric conversion section and an analog-digital conversion section. The photoelectric conversion section converts the first summed signal being an optical signal to an electric signal. The analog-digital conversion section converts the electric signal being an analog signal to a digital signal and outputs the digital signal as the first measurement signal.

Preferably, in the measuring device according to the present invention, the measurement section includes a phase calculating section and a first ratio calculating section. The phase calculating section calculates a phase of a fundamental in the first measurement signal. The first ratio calculating section calculates a value of a ratio of the second physical quantity to the first physical quantity based on the phase of the fundamental in the first measurement signal.

Preferably, in the measuring device according to the present invention, the measurement section further includes a delay calculating section that calculates a delay time of the first measurement signal relative to the first summed signal. Preferably, the first ratio calculating section calculates the value of the ratio in accordance with an equation (1).

[Formula 1]

$$r = \frac{p2 - pr}{p1 - pr} = \tan\left(\frac{\pi}{4} + \theta + 2\pi f \tau\right) \quad (1)$$

r represents the value of the ratio.
p1 represents the first physical quantity.
p2 represents the second physical quantity.
pr represents a reference physical quantity.
θ represents the phase of the fundamental in the first measurement signal.
f represents a frequency of the fundamental in the first measurement signal.
τ represents the delay time.

Preferably, the measuring device according to the present invention has a non-linearity error measurement mode including a first mode and a second mode. Preferably, in each of the first mode and the second mode, the first signal generation section outputs the first source signal in which the first physical quantity is maintained constant and the second physical quantity is changed in a stepwise manner. Preferably, in the first mode, the first summing section sums the harmonic signal and the first source signal to output the first summed signal, and the measurement section outputs the first measurement signal from which the harmonic has been removed. Preferably, in the first mode, the first ratio calculating section calculates the value of the ratio for each second physical quantity based on the first measurement signal from which the harmonic has been removed. Preferably, in the second mode, the first summing section outputs the first source signal as the first summed signal without summing the harmonic signal and the first source signal, and the measurement section outputs the first measurement signal from which none of the harmonics has been removed. Preferably, in the second mode, the first ratio calculating section calculates the value of the ratio for each second physical quantity based on the first measurement signal from which none of the harmonics has been removed. Preferably, the measurement section further includes a first difference calculating section and a storage section. The first difference calculating section calculates a difference between the value of the ratio calculated in the first mode and the value of the ratio calculated in the second mode for each second physical quantity. The storage section stores therein the difference in association with the value of the ratio calculated in the second mode for each second physical quantity.

Preferably, the measuring device according to the present invention further includes a second signal generation section and a second removal section. The second signal generation section generates a second source signal including a fundamental and a plurality of harmonics and having a waveform of the first source signal with the first physical quantity and the second physical quantity interchanged. The second removal section removes some or all of the plurality of harmonics from the second source signal.

Preferably, the measuring device according to the present invention further includes a second signal generation section and a second removal section. The second signal generation section generates a second source signal including a fundamental and a plurality of harmonics and having a waveform of the first source signal with the first physical quantity and the second physical quantity interchanged. The second removal section removes some or all of the plurality of harmonics from the second source signal. Preferably, the second removal section includes a second summing section, a harmonic generation section, a second Fourier transform section, and a second control section. The second summing section sums the second source signal and a harmonic signal having the same frequency as a removal target harmonic among the plurality of harmonics in the second source signal to output a second summed signal. The measurement section outputs the second summed signal in analog form as a second measurement signal in digital form. The harmonic generation section generates the harmonic signal that is summed with the second source signal. The second Fourier transform section calculates a plurality of harmonics included in the second measurement signal. The second control section causes the harmonic generation section to adjust either or both of an amplitude and a phase of the harmonic signal that is summed with the second source signal so that a harmonic that matches the removal target harmonic in the second source signal is removed.

Preferably, in the measuring device according to the present invention, the measurement section includes a phase difference calculating section and a second ratio calculating section. The phase difference calculating section calculates a phase difference between a fundamental in the first measurement signal and a fundamental in the second measurement signal. The second ratio calculating section calculates a value of a ratio of the second physical quantity to the first physical quantity based on the phase difference.

Preferably, in the measuring device according to the present invention, the measurement section further includes a delay difference calculating section. The delay difference calculating section calculates a delay time difference between the first measurement signal and the second measurement signal. Preferably, the second ratio calculating section calculates the value of the ratio in accordance with an equation (2).

[Formula 2]

$$r = \frac{p2 - pr}{p1 - pr} = \tan\left(\frac{\pi}{4} + \Delta\theta + \frac{2\pi f \Delta t}{2}\right) \quad (2)$$

r represents the value of the ratio.
p1 represents the first physical quantity.
p2 represents the second physical quantity.
pr represents a reference physical quantity.
$\Delta\theta$ represents the phase difference.
f represents a frequency of the fundamental in the first measurement signal.
$\Delta\tau$ represents the delay time difference.

Preferably, the measuring device according to the present invention has a non-linearity error measurement mode including a first mode and a second mode. Preferably, in each of the first mode and the second mode, the first signal generation section generates the first source signal in which the first physical quantity is maintained at a constant level and the second physical quantity is changed in a stepwise manner. Preferably, in each of the first mode and the second mode, the second signal generation section generates the second source signal in which the first physical quantity is maintained at the constant level and the second physical quantity is changed in a stepwise manner. Preferably, in the first mode, the first summing section sums the harmonic signal and the first source signal to output the first summed signal, and the measurement section outputs the first measurement signal from which the harmonic has been removed. Preferably, in the first mode, the second summing section sums the harmonic signal and the second source signal to output the second summed signal, and the measurement section outputs the second measurement signal from which the harmonic has been removed. Preferably, in the first mode, the second ratio calculating section calculates the value of the ratio for each second physical quantity based on the first measurement signal from which the harmonic has been removed and the second measurement signal from which the harmonic has been removed. Preferably, in the second mode, the first summing section outputs the first source signal as the first summed signal without summing the harmonic signal and the first source signal, and the measurement section outputs the first measurement signal from which none of the harmonics has been removed. Preferably, in the second mode, the second summing section outputs the second source signal as the second summed signal without summing the harmonic signal and the second source signal, and the measurement section outputs the second measurement signal from which none of the harmonics has been removed. Preferably, in the second mode, the second ratio calculating section calculates the value of the ratio for each second physical quantity based on the first measurement signal from which none of the harmonics has been removed and the second measurement signal from which none of the harmonics has been removed. Preferably, the measurement section further includes a second difference calculating section and a storage section. The second difference calculating section calculates a difference between the value of the ratio calculated in the first mode and the value of the ratio calculated in the second mode for each second physical quantity. The storage section stores therein the difference in association with the value of the ratio calculated in the second mode for each second physical quantity.

Preferably, in the measuring device according to the present invention, the measurement section further includes a third ratio calculating section and a correction section. The third ratio calculating section calculates a value of a ratio of a fourth physical quantity to a third physical quantity. The correction section corrects the value of the ratio calculated by the third ratio calculating section based on the difference stored in the storage section.

A measuring method according to a second aspect of the present invention includes a step of generating a first source signal including a fundamental and a plurality of harmonics based on a first physical quantity and a second physical quantity, and a step of removing some or all of the plurality of harmonics from the first source signal.

Advantageous Effects of Invention

According to the present invention, influence of non-linearity of a measuring device on measurement results can be easily reduced by removing some or all of a plurality of harmonics, which are a cause of occurrence of a non-linearity error.

BRIEF DESCRIPTION OF DRAWINGS

FIG. 29A is a block diagram illustrating a measuring device according to Embodiment 9 of the present invention.

FIG. 29B is a block diagram illustrating the measuring device according to a variation of Embodiment 9 of the present invention.

FIG. 33A is a waveform diagram illustrating a first measurement signal from which none of harmonics has been removed.

FIG. 33B is a waveform diagram illustrating a second measurement signal from which none of harmonics has been removed.

FIG. 33C is a waveform diagram illustrating a clock clk1.

FIG. 33D is a waveform diagram illustrating a clock clk2.

FIG. 33E is a waveform diagram illustrating a clock clk3.

DESCRIPTION OF EMBODIMENTS

Figure 1:
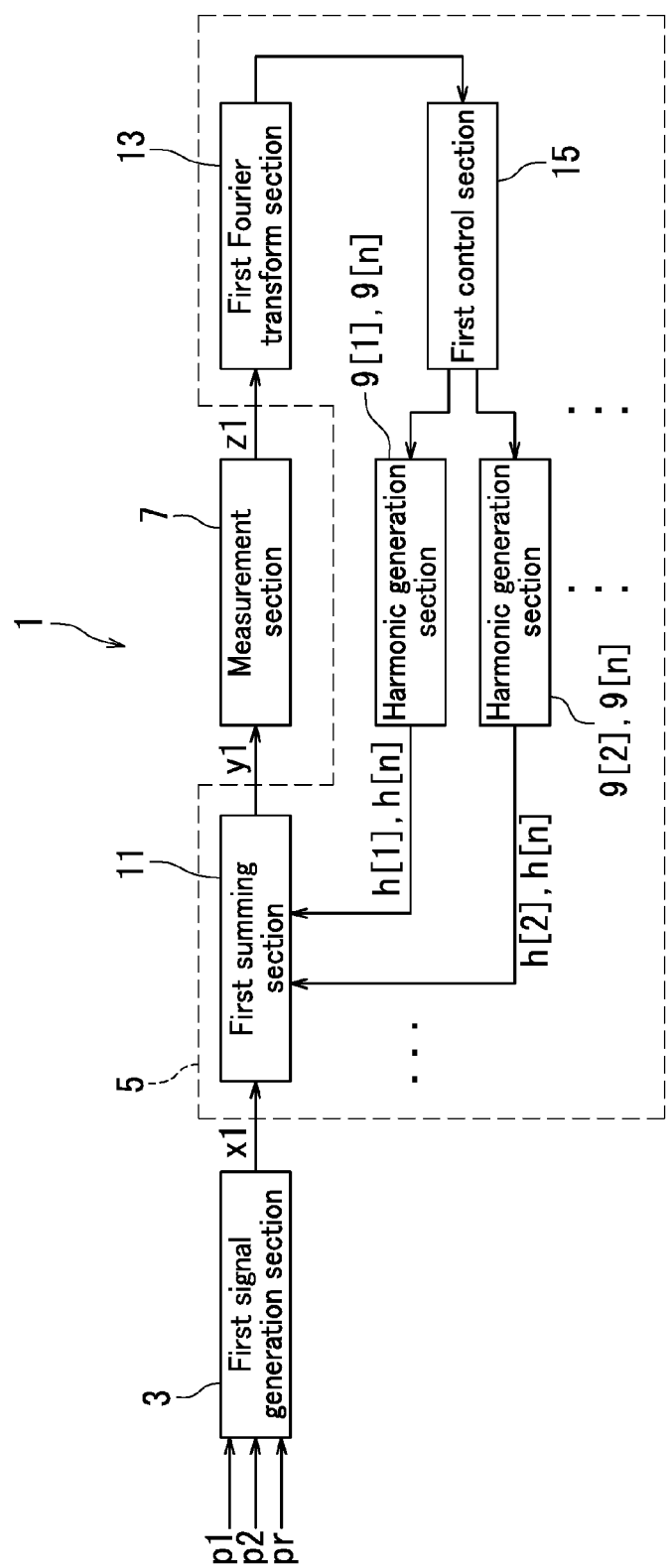
FIG. 1 is a block diagram illustrating a measuring device according to Embodiment 1 of the present invention.

The following describes embodiments of the present invention with reference to the drawings. Elements that are the same or equivalent are indicated by the same reference signs in the drawings and description thereof is not repeated.

(Embodiment 1)

FIG. 1 is a block diagram illustrating a measuring device 1 according to Embodiment 1 of the present invention. The measuring device 1 includes a first signal generation section 3 (first signal generation means), a first removal section 5 (first removal means), and a measurement section 7 (measurement means). The first signal generation section 3 generates a first source signal $x1(t)$ including a fundamental and a plurality of harmonics based on a first physical quantity p1 and a second physical quantity p2. In the present description, t represents time. The first removal section 5 removes some or all of the harmonics from the first source signal $x1(t)$.

According to Embodiment 1, influence of non-linearity of the measuring device 1 (measurement section 7) on measurement results can be easily reduced by removing some or all of the harmonics, which are a cause of occurrence of a non-linearity error.

The first removal section 5 includes N (N representing an integer greater than or equal to one) harmonic generation sections (harmonic generation means) 9[1] to 9[N], a first summing section 11 (first summing means), a first Fourier transform section 13 (first Fourier transform means), and a first control section 15 (first control means).

The number N of harmonic generation sections 9[1] to 9[N] is equal to the number of removal target harmonics in the first source signal $x1(t)$ that are to be removed by the first removal section 5. The harmonic generation sections 9[1] to 9[N] respectively generate harmonic signals h[1] to h[N].

Herein, the harmonic generation sections 9[1] to 9[N] will be collectively referred to as a harmonic generation section 9[n] (n representing an integer greater than or equal to one), and the harmonic signals h[1] to h[N] will be collectively referred to as a harmonic signal h[n].

The harmonic signal h[n] has the same frequency as a removal target harmonic among the plurality of harmonics included in the first source signal $x1(t)$. In the case where the removal target harmonic is a second-order harmonic, for example, the harmonic generation section 9[1] generates the harmonic signal h[1] having the same frequency as the second-order harmonic.

The first summing section 11 sums the harmonic signal h[n] and the first source signal $x1(t)$ to output a first summed signal $y1(t)$. The measurement section 7 outputs the first summed signal $y1(t)$, which is an analog signal, as a digital first measurement signal $z1(t)$. The first Fourier transform section 13 calculates a plurality of harmonics included in the first measurement signal $z1(t)$ through Fourier transform of the first measurement signal $z1(t)$.

The first control section 15 causes the harmonic generation section 9[n] to adjust either or both of an amplitude and a phase of the harmonic signal h[n] so that a harmonic that matches the removal target harmonic is removed from the first measurement signal $z1(t)$. In the case where the removal target harmonic is a second-order harmonic, for example, the first control section 15 causes the harmonic generation section 9[1] to adjust either or both of an amplitude and a phase of the harmonic signal h[1] having the same frequency as the second-order harmonic so that a second-order harmonic is removed from the first measurement signal $z1(t)$.

The first summing section 11 sums the first source signal $x1(t)$ and the harmonic signal h[n] having either or both of an adjusted amplitude and an adjusted phase to output the first summed signal $y1(t)$. The first summed signal $y1(t)$ is converted by the measurement section 7 to the first measurement signal z1(t), and the first measurement signal z1(t) is re-input into the first Fourier transform section 13.

The Fourier transform by the first Fourier transform section 13, the control of the harmonic generation section 9[n] by the first control section 15, the adjustment of either or both of the amplitude and the phase by the harmonic generation section 9[n], the summing by the first summing section 11, and the digital output by the measurement section 7 are repeated until harmonics that match the removal target harmonics are removed from the first measurement signal z1(t).

Figure 2:
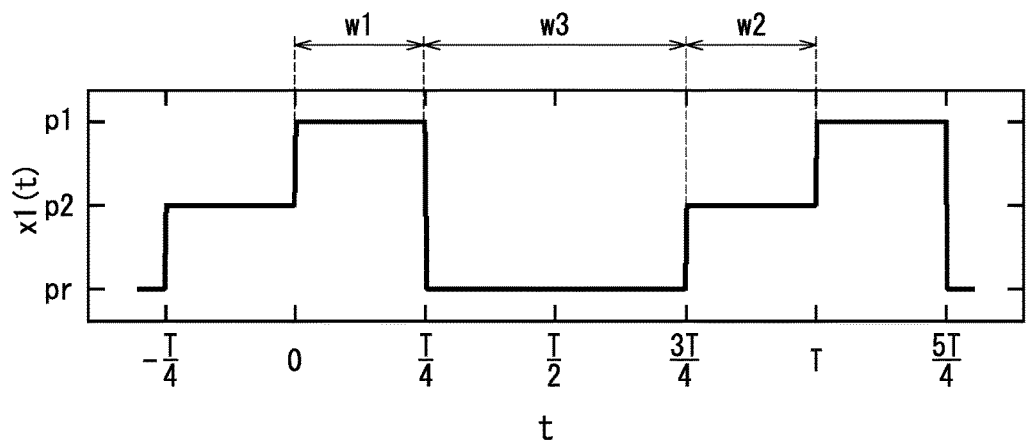
FIG. 2 is a waveform diagram illustrating a first source signal generated by a first signal generation section in FIG. 1.

The following describes the first source signal x1(t), the first summed signal y1(t), and the first measurement signal z1(t) in detail with reference to FIGS. 1 to 4. FIG. 2 is a waveform diagram illustrating the first source signal x1(t). The first signal generation section 3 generates the first source signal x1(t) based on the first physical quantity p1, the second physical quantity p2, and a reference physical quantity pr. The first source signal x1(t) is a periodic, staircase signal having a period T.

One period of the first source signal x1(t) includes a first signal p1 indicating the first physical quantity p1, a reference signal pr indicating the reference physical quantity pr, and a second signal p2 indicating the second physical quantity p2.

The first signal p1 indicating the first physical quantity p1 has a first duration w1 (=(¼) period) from time 0 to time T/4. The reference signal pr indicating the reference physical quantity pr has a third duration w3 (=(²⁄₄) period) from time T/4 to time 3T/4. The second signal p2 indicating the second physical quantity p2 has a second duration w2 (=(¼) period) from time 3T/4 to time T.

The first source signal x1(t) has a plurality of frequency components, not shown in FIG. 2. That is, the first source signal x1(t) includes a fundamental and a plurality of harmonics. The fundamental has a frequency f (=1/T). The plurality of harmonics respectively have frequencies 2f, 3f, 5f That is, each of the frequencies of the harmonics is a frequency that is k times the frequency f. k is an integer greater than or equal to two excluding multiples of four. Each of fundamentals of the first summed signal y1(t) and the first measurement signal z1(t) that are generated from the first source signal x1(t) has a frequency equal to the frequency f of the fundamental in the first source signal x1(t). Accordingly, the frequency of each of harmonics of the first summed signal y1(t) is a frequency k times the frequency f, and the frequency of each of harmonics of the first measurement signal z1(t) is a frequency k times the frequency f. However, k may be a multiple of four in the cases of the harmonics in the first summed signal y1(t) and the first measurement signal z1(t).

Figure 3:
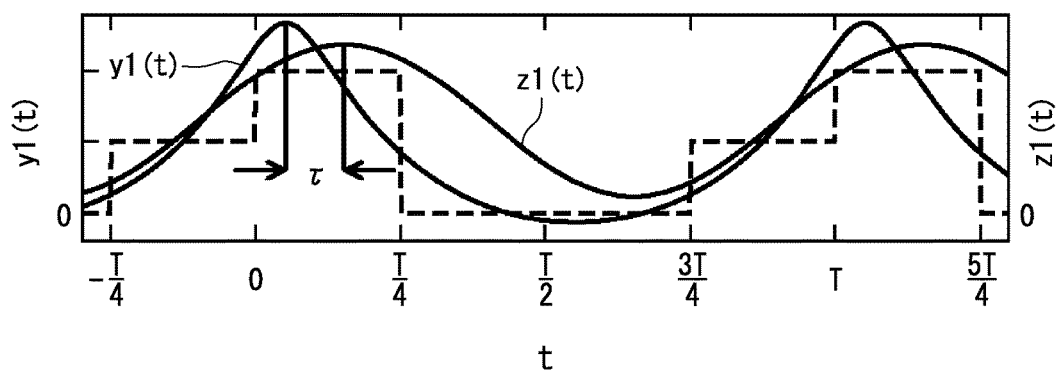
FIG. 3 is a waveform diagram illustrating a first summed signal generated by a first summing section in FIG. 1 and a first measurement signal generated by a first measurement section in FIG. 1.

FIG. 3 is a waveform diagram illustrating the first summed signal y1(t) and the first measurement signal z1(t). The first summed signal y1(t) is generated by summing the first source signal x1(t) and the harmonic signal h[n]. In FIG. 3, the harmonics remain in the first summed signal y1(t). The measurement section 7 measures the first summed signal y1(t) and generates the first measurement signal z1(t) as a result of the measurement. Then, Fourier transform of the first measurement signal z1(t) is performed, and in the example illustrated in FIG. 3, feed back control of the harmonic generation section 9[n] is performed so that no harmonics remain. As a result, the first measurement signal z1(t) including no harmonics is obtained. That is, the first measurement signal z1(t) is a sine wave including only the fundamental.

Figure 4:
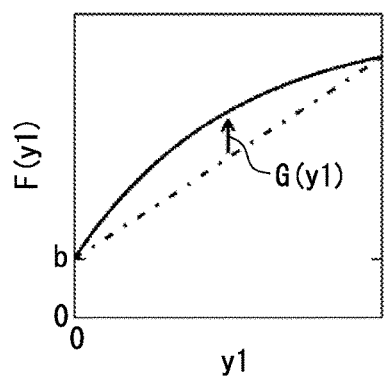
FIG. 4 is a diagram illustrating input/output characteristics of a measurement section in FIG. 1.

The first measurement signal z1(t) illustrated in FIG. 3 is calculated using a non-linear response function F(y1) shown in FIG. 4. FIG. 4 is a diagram illustrating an example of input/output characteristics of the measurement section 7. The measurement section 7 has non-linearity. The non-linearity of the measurement section 7 is represented by the non-linear response function F(y1). y1 represents any input. The non-linearity of the measurement section 7 causes a non-linearity error G(y1). The first measurement signal z1(t) is represented by a non-linear response function F (y1(t−τ)). τ represents a delay time by which the first measurement signal z1(t) is delayed relative to the first summed signal y1(t). The delay time τ is specific to the measurement section 7 and is frequency-independent.

Figure 5A:
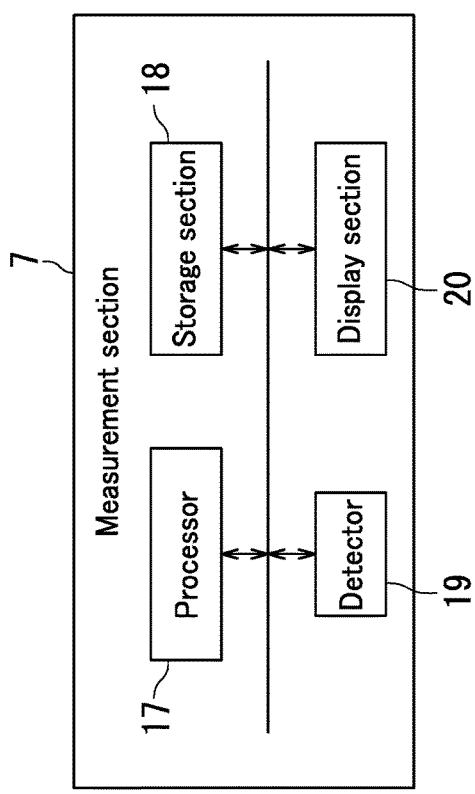
FIG. 5A is a diagram illustrating an electrical configuration of the measurement section in FIG. 1.
Figure 5B:
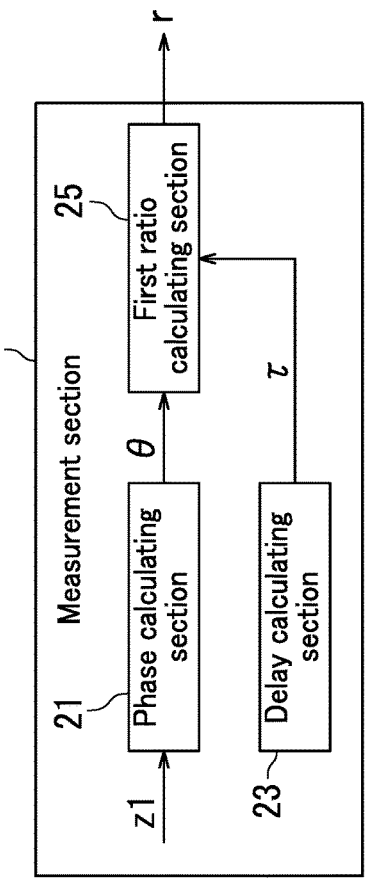
FIG. 5B is a functional block diagram of the measurement section in FIG. 1.

The following describes a method for calculating a value r of a ratio of the second physical quantity p2 to the first physical quantity p1 with reference to FIGS. 3 and 5A-5B. The measurement section 7 calculates the value r of the ratio. FIG. 5A is a diagram illustrating an electrical configuration of the measurement section 7. The measurement section 7 includes a processor 17, a storage section 18, a detector 19, and a display section 20.

The processor 17 is for example a central processing unit (CPU), a micro controller unit (MCU), or a field-programmable gate array (FPGA). The processor 17 may include a digital signal processor (DSP). The storage section 18 is for example semiconductor memory such as random access memory (RAM), read only memory (ROM), and flash memory. The storage section 18 may include an auxiliary storage device such as a hard disk drive. The storage section 18 is an example of what may be referred to as a storage medium. The detector 19 detects the analog first summed signal y1(t) and outputs the first summed signal y1(t) as the digital first measurement signal z1(t). The detector 19 for example includes an analog-digital converter in the case of voltage measurement. The detector 19 for example includes a photoelectric conversion section and an analog-digital converter in the case of optical measurement. The display section 20 displays a measurement result (for example, the value r of the ratio). The display section 20 is for example a liquid crystal display.

FIG. 5B is a functional block diagram of the measurement section 7. The measurement section 7 includes a phase calculating section 21 (phase calculating means), a delay calculating section 23 (delay calculating means), and a first ratio calculating section 25 (first ratio calculating means). The processor 17 functions as the phase calculating section 21, the delay calculating section 23, and the first ratio calculating section 25 through execution of a computer program stored in the storage section 18.

The first ratio calculating section 25 calculates the value r of the ratio of the second physical quantity p2 to the first physical quantity p1 based on a phase θ of the fundamental in the first measurement signal z1(t). That is, the phase calculating section 21 calculates the phase θ of the fundamental. The delay calculating section 23 calculates the delay time τ of the first measurement signal z1(t) relative to the first summed signal y1(t). The first ratio calculating section 25 calculates the value r of the ratio in accordance with an equation (1). In the equation (1), pr represents the reference physical quantity, and f represents the frequency of the fundamental in the first measurement signal z1(t). In Embodiment 1, pr=0.

[Formula 3]

$$r = \frac{p2 - pr}{p1 - pr} = \tan\left(\frac{\pi}{4} + \theta + 2\pi f \tau\right) \quad (1)$$

As illustrated in FIG. 3, the harmonics remain in the first summed signal y1(t). However, in a configuration in which a characteristic frequency of the measurement section 7 is sufficiently higher than the frequency of the fundamental, an input signal that outputs a sine wave has peaks at the same positions as peak positions of a sine wave, although the delay time τ is present. Accordingly, the value r of the ratio can be calculated from the phase θ in accordance with the equation (1) as long as the delay time τ is determined in advance by measuring the phase θ on the assumption that p1=p2. In this case, at the same time, correction is performed on a reference point in the time axis for calculation of the phase θ. According to Embodiment 1, the value r of the ratio can be calculated easily by measuring the phase θ of the fundamental and using the equation (1).

Figure 6:
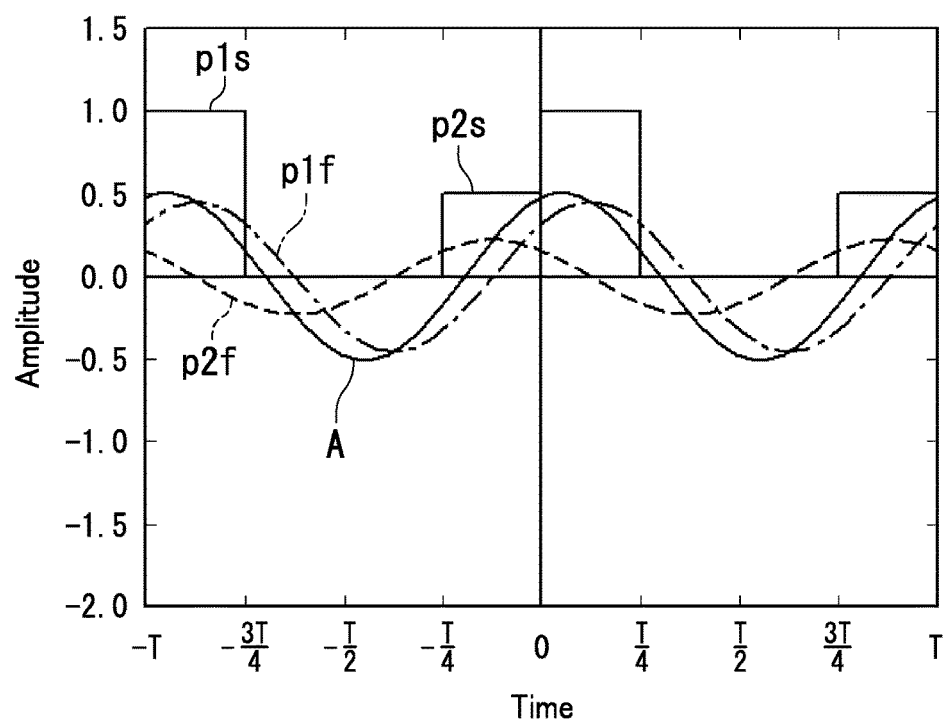
FIG. 6 is a waveform diagram for schematically describing an equation (1) that is used by the measurement section in FIG. 1.
Figure 7:
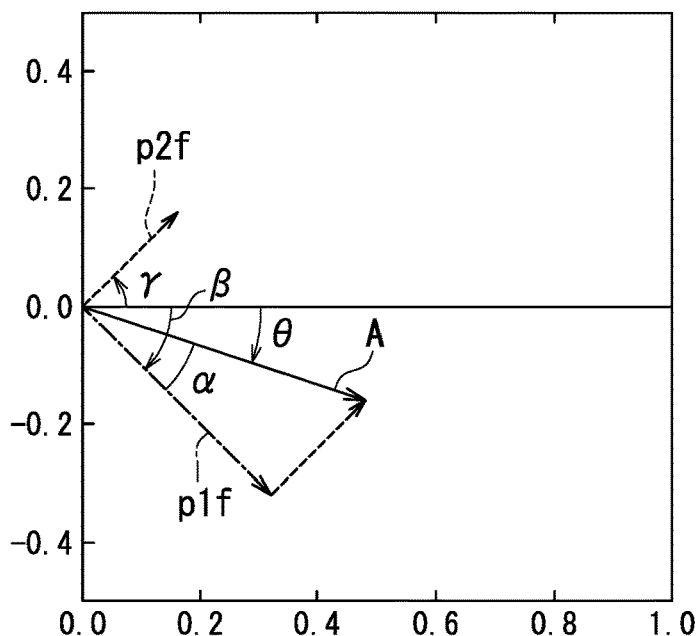
FIG. 7 is a diagram illustrating a vector for schematically describing the equation (1) that is used by the measurement section in FIG. 1.

The following schematically describes the equation (1) assuming the delay time τ is 0 with reference to FIGS. 6 and 7. FIG. 6 is a waveform diagram for schematically describing the equation (1). FIG. 7 is a diagram illustrating a vector for schematically describing the equation (1).

FIG. 6 illustrates a square wave p1s only of the first physical quantity p1, a square wave p2s only of the second physical quantity p2, a fundamental p1f of the square wave p1s, a fundamental p2f of the square wave p2s, and a composite wave A. The composite wave A is a wave obtained by combining the fundamental p1f and the fundamental p2s.

As illustrated in FIGS. 6 and 7, the fundamental p1f is a sine wave having a phase β of −45 degrees and an amplitude of ($\sqrt{2}$× (p1/π)), and can be represented as a vector p1f in a complex plane. The fundamental p2f is a sine wave having a phase γ of 45 degrees and an amplitude of ($\sqrt{2}$× (p2/π)), and can be represented as a vector p2f in a complex plane. The composite wave A can be represented as a resultant vector A. An angle α is determined to be 45 degrees+θ using the phase θ of the composite vector A. The value r of the ratio is therefore represented by an equation (1A). The phase β, the phase γ, and the phase θ each include a plus or minus sign. In the example illustrated in FIG. 7, the phase β and the phase θ are each a negative value, and the phase γ is a positive value.

[Formula 4]

$$r = \frac{p2 - pr}{p1 - pr} = \tan\alpha = \tan\left(\frac{\pi}{4} + \theta\right) \quad (1A)$$

Figure 8:
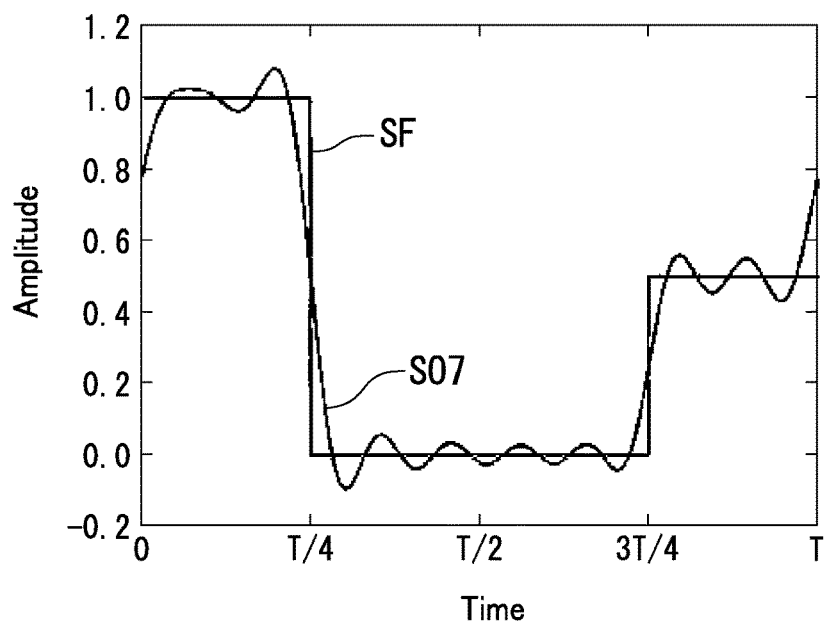
FIG. 8 is a waveform diagram illustrating a staircase signal.
Figure 9:
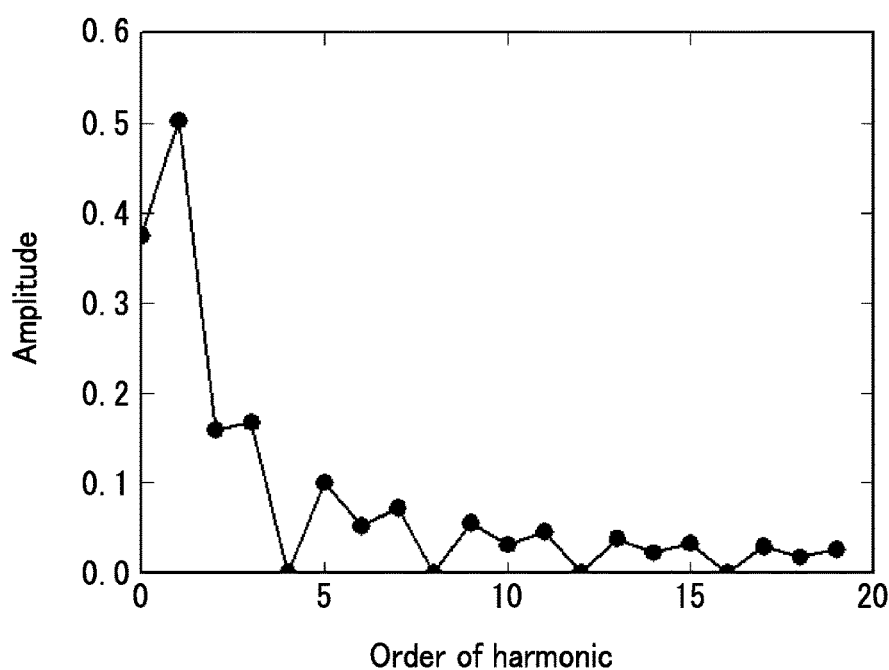
FIG. 9 is a diagram illustrating frequency distribution of the staircase signal.

The following describes influence of harmonics of a staircase signal SF on a non-linearity error with reference to FIGS. 8 to 11. FIG. 8 is a waveform diagram illustrating the staircase signal SF. The staircase signal SF has the same waveform as the first source signal x1(t) illustrated in FIG. 2 and is generated based on the first physical quantity p1 (=1), the second physical quantity p2 (=0.5), and the reference physical quantity pr (=0). FIG. 9 is a diagram illustrating frequency distribution of the staircase signal SF. The staircase signal SF includes a plurality of low-order to high-order harmonics.

Suppose that the staircase signal SF is measured using a non-linear measuring device. In such a situation, generally, an output signal includes a non-linearity error although the output signal is a staircase signal similar to an input signal so long as frequency dependency of the delay time of the measuring device is negligible. A height ratio r of the staircase signal SF can be calculated from the phase θ of the fundamental having the frequency f as indicated by the equation (1). Influence of non-linearity in frequency space will now be considered.

Operating a non-linear function upon the harmonics of the staircase signal SF causes mixing of harmonics, mixing of a $0^{th}$-order term (constant) with a harmonic, and mixing of a fundamental with harmonics. As a result, a new fundamental is generated. In a situation in which the new fundamental has a different phase from the original fundamental, the fundamentals are phase-shifted with respect to one another. Such fundamental phase shifting causes a non-linearity error.

A measuring device is now defined by a quadratic non-linearity function (z=x +0.5×x$^2$). The following describes fundamental phase shifting due to mixing with harmonics in the case where the staircase signal SF is measured using the thus defined measuring device.

Figure 10:
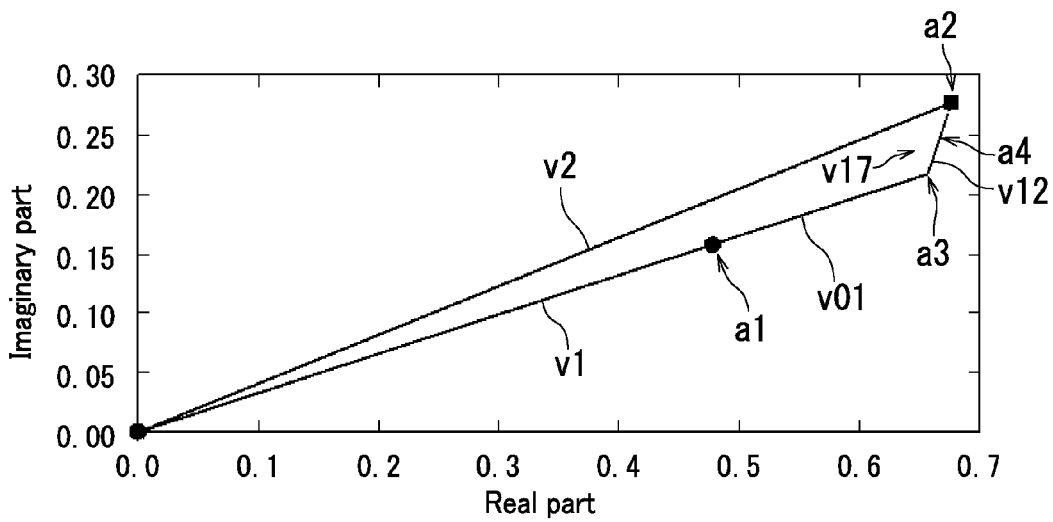
FIG. 10 is a diagram illustrating fundamental phase shifting due to mixing of harmonics.
Figure 11:
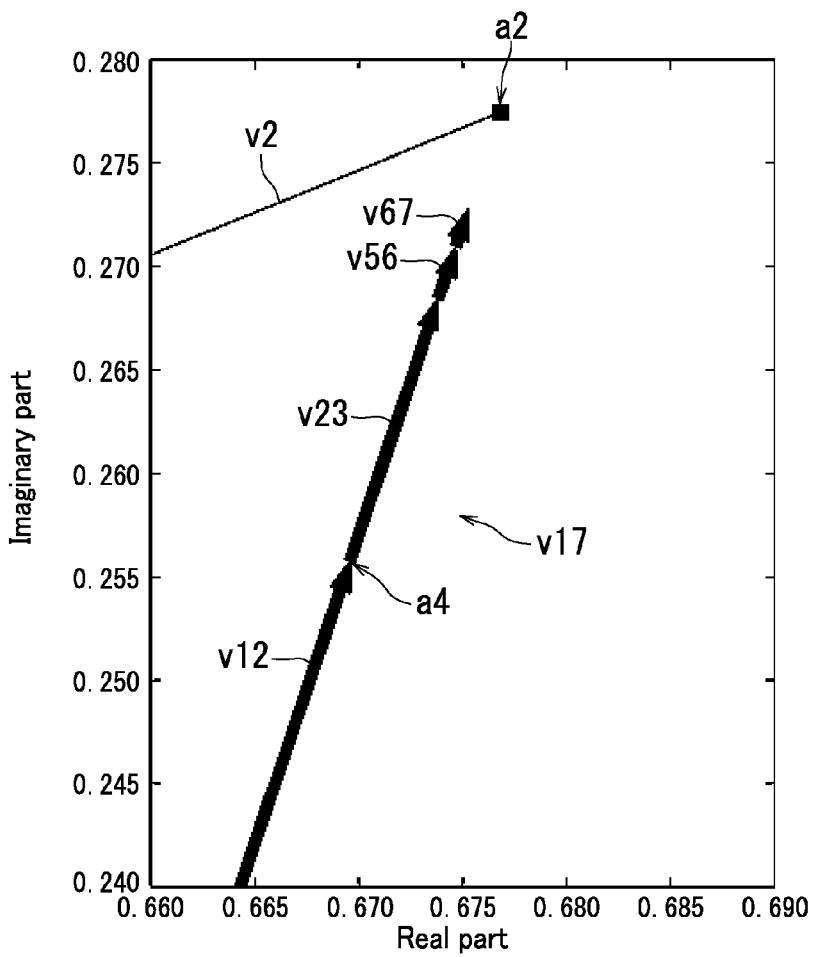
FIG. 11 is an enlarged view of a portion of a straight line in FIG. 10.

FIG. 10 is a diagram illustrating fundamental phase shifting due to mixing with harmonics. FIG. 11 is an enlarged view of a straight line v17 in FIG. 10. The fundamental corresponding to a true value (the original fundamental) is represented by a straight line v1 extending from the origin to point a1. The fundamental corresponding to a measurement value including all the harmonics (the new fundamental) is represented by a straight line v2 extending from the origin to point a2. It can be confirmed that the fundamentals are phase-shifted with respect to one another.

A straight line v01 extending from point a1 to point a3 corresponds to mixing of the $0^{th}$-order term with the first-order term. The first-order term represents the original fundamental. It can be confirmed that mixing of the $0^{th}$-order term with the first order term has no influence on the phase of the original fundamental.

A straight line v12 extending from point a3 to point a4 corresponds to mixing of the first-order term with a second-order harmonic. A straight line v23 corresponds to mixing of the second-order harmonic with a third-order harmonic. A straight line v56 corresponds to mixing of a fifth-order harmonic with a sixth-order harmonic. A straight line v67 corresponds to mixing of the sixth-order harmonic with a seventh-order harmonic. It should be noted that there is no forth-order harmonic.

It can be confirmed that mixing of the first-order term with the second-order harmonic, mixing of the second-order harmonic with the third-order harmonic, mixing of the fifth-order harmonic with the sixth-order harmonic, and mixing of the sixth-order harmonic with the seventh-order harmonic have influence on the phase of the original fundamental. Mixing of the first-order term with the second-order harmonic shifts the phase of the original fundamental to the greatest extent. Mixing of the second-order harmonic with the third-order harmonic shifts the phase of the original fundamental to the second greatest extent. That is, a lower-order harmonic has greater influence on the phase of the original fundamental, shifting the phase of the original fundamental to a greater extent.

Since the value r of the ratio is expressed using the phase θ of the fundamental as shown in the equation (1), the phase shifting of the original fundamental causes the value r of the ratio to deviate from the true value and include a non-linearity error. Since the harmonics cause phase shifting of the original fundamental, it is thought that the harmonics are a cause of the non-linearity error included in the value r of the ratio. A lower-order harmonic shifts the phase of the original fundamental to a greater extent. That is, the low-order harmonics are responsible for a majority of the non-linearity error. Generally, the non-linearity error changes only modestly relative to the measurement value. It is therefore thought that the high-order harmonics, which have a small amplitude, have little influence on the degree of the non-linearity error.

As illustrated in FIG. 9, the staircase signal SF includes higher-order harmonics than the seventh-order harmonic, but the amplitude of the higher-order harmonics is small. Accordingly, the staircase signal SF can be sufficiently reproduced using a signal S07 including the $0^{th}$-order to seventh-order harmonics as illustrated in FIG. 8.

Since harmonics, particularly low-order harmonics are responsible for a non-linearity error as described above, the measuring device 1 reduces influence of non-linearity of the measuring device 1 on measurement results by removing some or all of the harmonics. Which orders of harmonics should be removed and to what degree a non-linearity error can be reduced by the harmonic removal can for example be estimated through numerical simulation assuming non-linearity of the measurement section 7.

Figure 12:
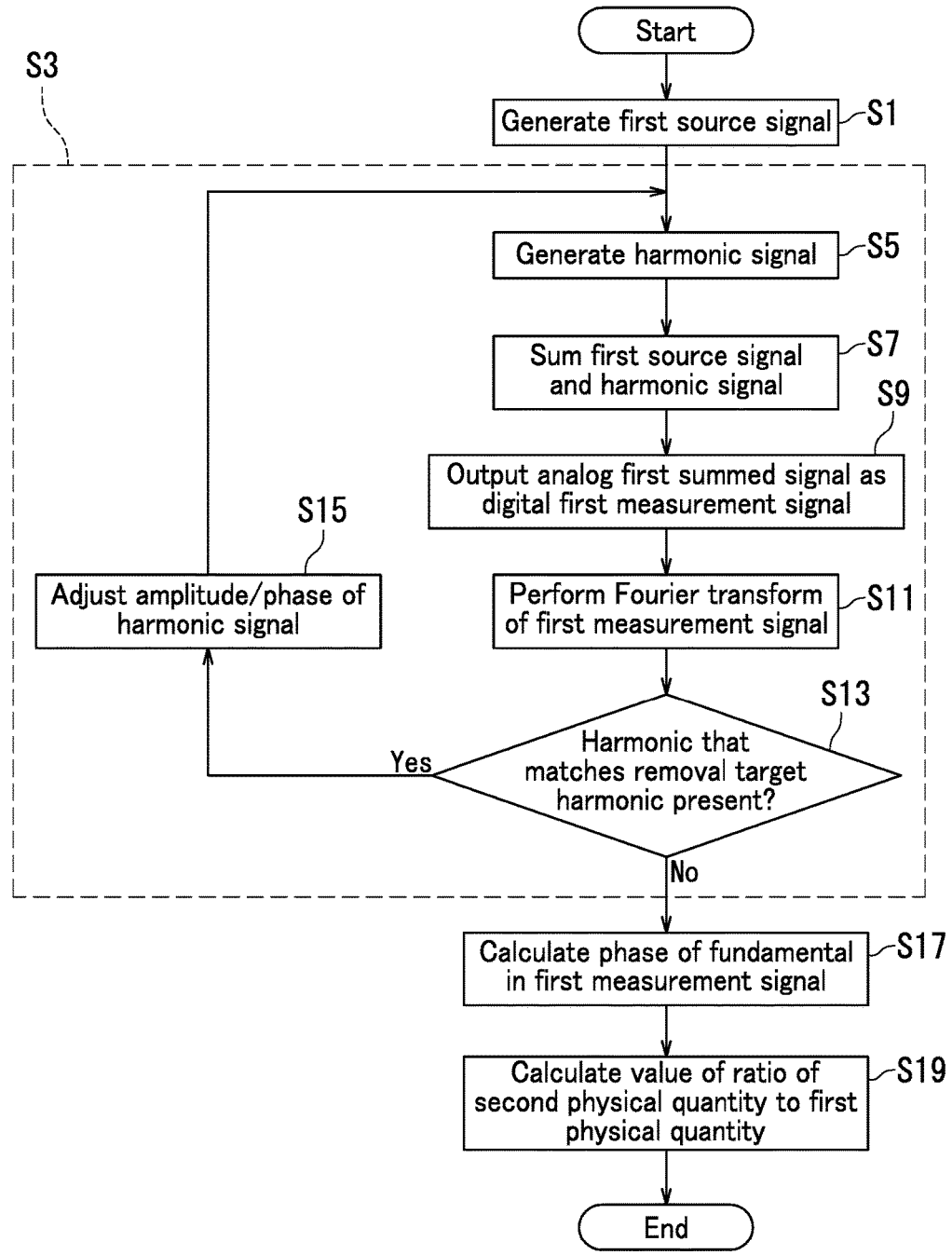
FIG. 12 is a flowchart illustrating a measuring method that is performed by the measuring device according to Embodiment 1 of the present invention.

The following describes a flow of a measuring method that is performed by the measuring device 1 with reference to FIGS. 1, 5A-5B, and 12. FIG. 12 is a flowchart illustrating the measuring method. The measuring device 1 performs processes in steps S1 to S19. Step S3 includes steps S5 to S15.

In Step S1, the first signal generation section 3 generates the first source signal x1(t) including a fundamental and a plurality of harmonics based on the first physical quantity p1, the second physical quantity p2, and the reference physical quantity pr.

In Step S3, the first removal section 5 removes some or all of the harmonics from the first source signal x1(t).

That is, in Step S5, the harmonic generation section 9[n] generates the harmonic signal h[n]. In Step S7, the first summing section 11 sums the first source signal x1(t) and the harmonic signal h[n] to output the first summed signal y1(t). In Step S9, the measurement section 7 (the detector 19) outputs the first summed signal y1(t), which is an analog signal, as the digital first measurement signal z1(t).

In Step S11, the first Fourier transform section 13 calculates harmonics included in the first measurement signal z1(t) through Fourier transform of the first measurement signal z1(t). In Step S13, the first control section 15 determines whether or not the first measurement signal z1(t) includes a harmonic that matches a removal target harmonic. If a result of the determination is positive (Yes in Step S13), the first control section 15 takes the process to Step S15. If the result of the determination is negative (No in Step S13), the first control section 15 takes the process to Step S17.

In Step S15, the first control section 15 causes the harmonic generation section 9[n] to adjust either or both of the amplitude and the phase of the harmonic signal h[n] so that the harmonic that matches the removal target harmonic is removed from the first measurement signal z1(t). Subsequently, the process proceeds to Step S5. The processes in Steps S5 to S15 are repeated until harmonics that match the removal target harmonics are removed from the first measurement signal z1(t). Through the above-described feedback control, the removal target harmonics can be removed reliably.

In Step S17, the phase calculating section 21 calculates the phase θ of the fundamental in the first measurement signal z1(t). In Step S19, the first ratio calculating section 25 calculates the value r of the ratio of the second physical quantity p2 to the first physical quantity p1 in accordance with the equation (1). It should be noted that the delay calculating section 23 calculates in advance the delay time τ based on the phase θ when p1=p2 in accordance with the equation (1).

According to Embodiment 1, as described above with reference to FIGS. 1 to 12, influence of non-linearity of the measurement section 7 (the detector 19) can be reduced by removing some or all of the harmonics from the first measurement signal z1(t). As a result, a non-linearity error included in the value r of the ratio can be reduced. It is not that non-linearity of the measurement section 7 is reduced, but influence of the non-linearity of the measurement section 7 is reduced. Therefore, the measurement section 7, for example, the detector 19 does not need to be improved. Accordingly, even if the detector 19 is an existing product, the non-linearity error included in the value r of the ratio can be reduced.

According to Embodiment 1, as described with reference to FIGS. 1 and 5A-5B, the value r of the ratio is calculated from the phase θ of the fundamental in the first measurement signal z1(t) from which some or all of the harmonics have been removed. That is, reduction of non-linearity of the measurement section 7 is performed at the same time as the measurement. Thus, the measuring device 1 in Embodiment 1 is utilized in simultaneous calibration. Since reduction of influence of non-linearity is performed at the same time as the measurement, such calibration is less likely to be influenced by a drift in non-linearity of the measurement section 7, unlike typical multipoint calibration. Typical multipoint calibration has a time difference between calibration and measurement. Accordingly, there may be a drift in non-linearity of the measuring device.

According to Embodiment 1, as described with reference to FIGS. 2 and 5A-5B, no other reference point than the reference physical quantity pr (i.e., zero point) is required unlike typical multipoint calibration. For example, assuming that the second physical quantity p2 is measured using the first physical quantity p1 as a reference signal, the measuring device 1 will perform calibration using two references (the reference physical quantity pr and the first physical quantity p1) as in the case of typical two-point calibration. Embodiment 1 uses only two references as in the case of two-point calibration but has the same effect as multipoint calibration, reducing influence of non-linearity on measurement results without reducing non-linearity of the measurement section 7. It should be noted that according to typical two-point calibration, correction is limited to within the range of linearity, and only calibration of offset and gain is enabled.

According to Embodiment 1, as described with reference to FIG. 2, the first source signal x1(t) is generated that includes the first signal p1 having the first duration w1, the reference signal pr having the third duration w3, and the second signal p2 having the second duration w2. As a result, the value r of the ratio can be determined through simple calculation represented by the equation (1).

(Embodiment 2)

The following describes a measuring device 1 according to Embodiment 2 of the present invention with reference to FIGS. 1, 2, 5A-5B, and 13. As the measuring device 1 according to Embodiment 2, the measuring device 1 according to Embodiment 1 is applied to voltage measurement. Accordingly, each of the first physical quantity p1, the second physical quantity p2, and the reference physical quantity pr in FIG. 1 is a voltage. Each of the first source signal x1(t), the first summed signal y1(t), the first measurement signal z1(t), and the harmonic signal h[n] is an electric signal. The measuring device 1 is utilized in simultaneous calibration.

Figure 13:
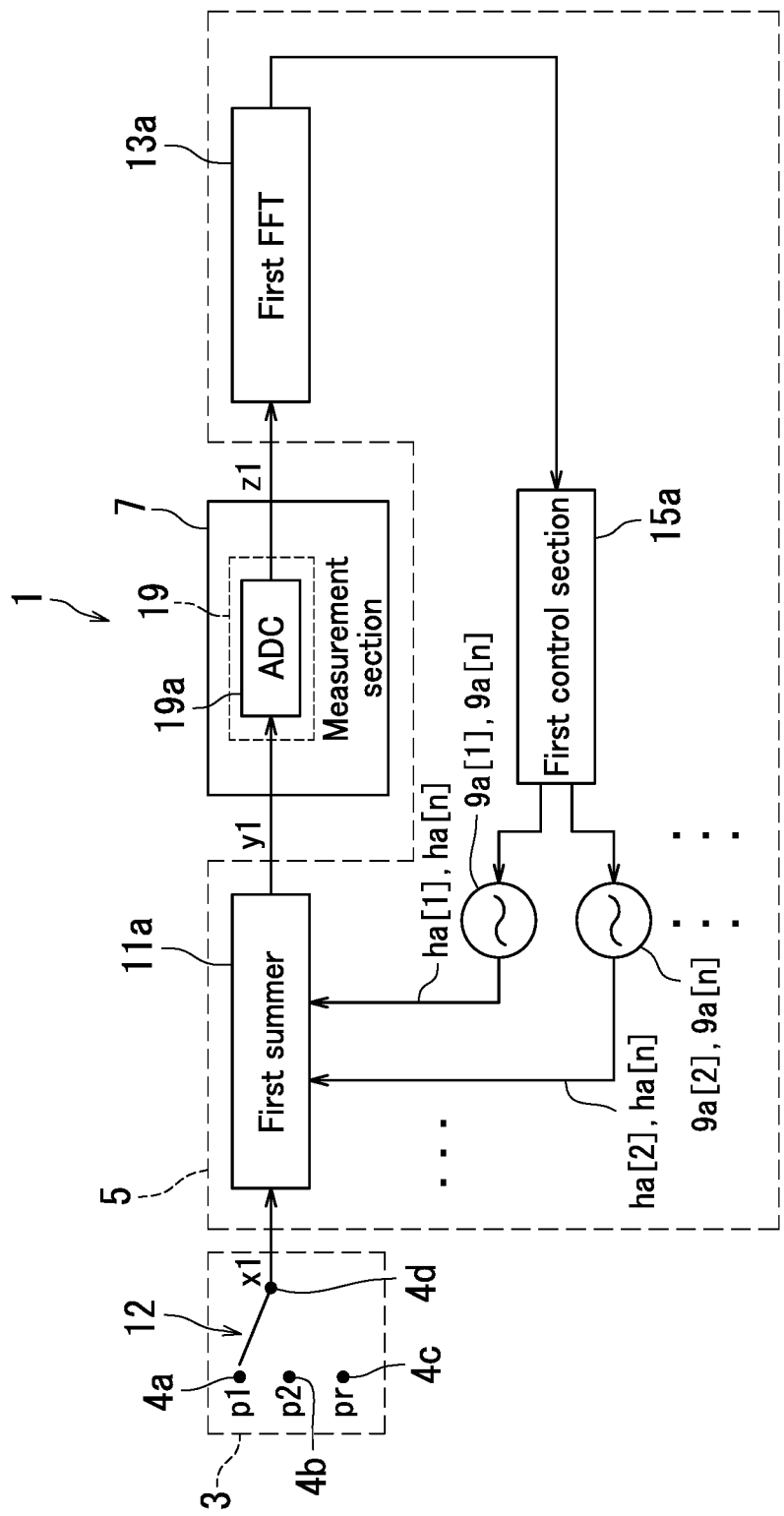
FIG. 13 is a block diagram illustrating a measuring device according to Embodiment 2 of the present invention.

FIG. 13 is a block diagram illustrating the measuring device 1 according to Embodiment 2. The measuring device 1 includes a first signal generation section 3 (first signal generation means), a first removal section 5 (first removal means), and a measurement section 7 (measurement means). An electrical configuration of the measurement section 7 is the same as the electrical configuration of the measurement section 7 illustrated in FIG. 5A. A detector 19 according to Embodiment 2 includes an analog-digital converter 19a (hereinafter, referred to as an "ADC 19a") (analog-digital conversion section or analog-digital conversion means). The ADC 19a converts an analog signal to a digital signal.

The first signal generation section 3 includes a switch 12, and the switch 12 includes contacts 4a to 4d. A voltage p1 is applied to the contact 4a as the first physical quantity p1. A voltage p2 is applied to the contact 4b as the second physical quantity p2. A voltage pr is applied to the contact 4c as the reference physical quantity pr. In Embodiment 2, the voltage pr is 0 V.

The switch 12 switches the contact that is connected with the contact 4d among the contacts 4a to 4c thereby to generate the staircase first source signal x1(t). That is, as illustrated in FIG. 2, the switch 12 connects the contact 4a with the contact 4d during an interval from time 0 to time T/4, connects the contact 4c with the contact 4d during an interval from time T/4 to time 3T/4, and connects the contact 4b with the contact 4d during an interval from time 3T/4 to time T. The switch 12 repeats such connection to generate the periodic, staircase first source signal x1(t).

The first removal section 5 includes N (N representing an integer greater than or equal to one) oscillators 9a[1] to 9a[N] (harmonic generation means), a first summer 11a (first summing means), a first fast Fourier transform device 13a (hereinafter, referred to as a "first FFT 13a" (first Fourier transform section or first Fourier transform means), and a first control section 15a (first control means).

The number N of oscillators 9a[1] to 9a[N] is equal to the number of removal target harmonics in the first source signal x1(t) that are to be removed by the first removal section 5. The oscillators 9a[1] to 9a[N] respectively generate harmonic electric signals ha[1] to ha[N].

Herein, the oscillators 9a[1] to 9[N] will be collectively referred to as an oscillator 9a[n] (n representing an integer greater than or equal to one), and the harmonic electric signals ha[1] to ha[N] will be collectively referred to as a harmonic electric signal ha[n].

The harmonic electric signal ha[n] has the same frequency as a removal target harmonic among the plurality of harmonics included in the first source signal x1(t).

The first summer 11a sums the harmonic electric signal ha[n] and the first source signal x1(t) to output the first summed signal y1(t). The ADC 19a converts the first summed signal y1(t), which is an analog signal, to a digital signal and outputs the digital signal as the first measurement signal z1(t). The first FFT 13a performs fast Fourier transform to calculate a plurality of harmonics included in the first measurement signal z1(t).

The first control section 15a causes the oscillator 9a[n] to adjust either or both of an amplitude and a phase of the harmonic electric signal ha[n] so that a harmonic that matches the removal target harmonic is removed from the first measurement signal z1(t). As in Embodiment 1, the control of the oscillator 9a[n] by the first control section 15a, the adjustment of either or both of the amplitude and the phase by the oscillator 9a[n], the summing by the first summer 11a, and the analog-digital conversion by the detector 19, and the fast Fourier transform by the first FFT 13a are repeated until harmonics that match the removal target harmonics are removed from the first measurement signal z1(t).

As in Embodiment 1, the measurement section 7 includes a phase calculating section 21, a delay calculating section 23, and a first ratio calculating section 25. As in Embodiment 1, the measurement section 7 calculates the value r of the ratio in accordance with the equation (1).

Furthermore, as in Embodiment 1, the measuring device 1 performs the measuring method illustrated by the flowchart in FIG. 12. In the case of Embodiment 2, the harmonic generation section 9[n] is replaced with the oscillator 9a[n], the harmonic signal h[n] is replaced with the harmonic electric signal ha[n], the first summing section 11 is replaced with the first summer 11a, the first Fourier transform section 13 is replaced with the first FFT 13a, and the first control section 15 is replaced with the first control section 15a in the illustration in FIG. 12.

According to Embodiment 2, as described above with reference to FIG. 13, influence of non-linearity of the measurement section 7 (the ADC 19a) can be reduced by removing some or all of the harmonics from the first measurement signal z1(t) in voltage measurement. As a result, a non-linearity error included in the value r of the ratio, that is, a voltage ratio can be reduced. In addition to the above, Embodiment 2 also achieves the same effects as Embodiment 1.

Furthermore, the measuring device 1 according to Embodiment 2 can be applied to direct current voltage measurement. The measuring device 1 is effectively utilized in simultaneous calibration in direct current voltage measurement.

In direct current voltage measurement, the measuring device 1 can be applied to a commercially-available high-end digital voltmeter (digital multimeter) including an analog-digital converter (AD converter) adopting a double integration technique or a multiple integration technique.

A digital voltmeter having a linearity of 10 ppb can for example be achieved. Measurement of a voltage ratio (the value r of the ratio) is a basic aspect of voltage measurement. Therefore, linear voltage ratio measurement is a necessary technique for achieving a high-precision digital voltmeter. Linearity can be further improved by for example employing a commercially-available high-end digital voltmeter as the measurement section 7. A digital voltmeter having a linearity of 10 ppb can be utilized for high-precision physical measurement as well as for secondary calibration. The measuring device 1 may be produced as a new digital voltmeter rather than being applied to an existing digital voltmeter.

In direct current voltage measurement, the measuring device 1 can be applied to a relatively inexpensive digital voltmeter including a delta-sigma or successive-approximation-register (SAR) AD converter. A digital voltmeter having a linearity of 1 ppm can for example be achieved. A delta-sigma or SAR digital voltmeter has a relatively high S/N ratio but does not have sufficient linearity. A low-cost digital voltmeter having a linearity of 1 ppm can for example be achieved by employing a delta-sigma or SAR digital voltmeter as the measurement section 7.

Some analog band-elimination filters used in voltage measurement employ a method involving phase-inverting an output from a bandpass filter and summing the output and an original signal. The first FFT 13a, the first control section 15a, and the oscillator 9a[h] according to Embodiment 2 achieve a multichannel band-elimination filter by phase detection using digital signal processing.

(Embodiment 3)

The following describes a measuring device 1 according to Embodiment 3 of the present invention with reference to FIGS. 1, 2, 5A-5B, and 14. As the measuring device 1 according to Embodiment 3, the measuring device 1 according to Embodiment 1 is applied to optical measurement such as spectroscopic measurement. Accordingly, each of the first physical quantity p1, the second physical quantity p2, and the reference physical quantity pr in FIG. 1 is an optical intensity. Each of the first source signal x1(t), the harmonic signal h[n], and the first summed signal y1(t) is an optical signal. The first measurement signal z1(t) is an electric signal. The measuring device 1 is utilized in simultaneous calibration.

Figure 14:
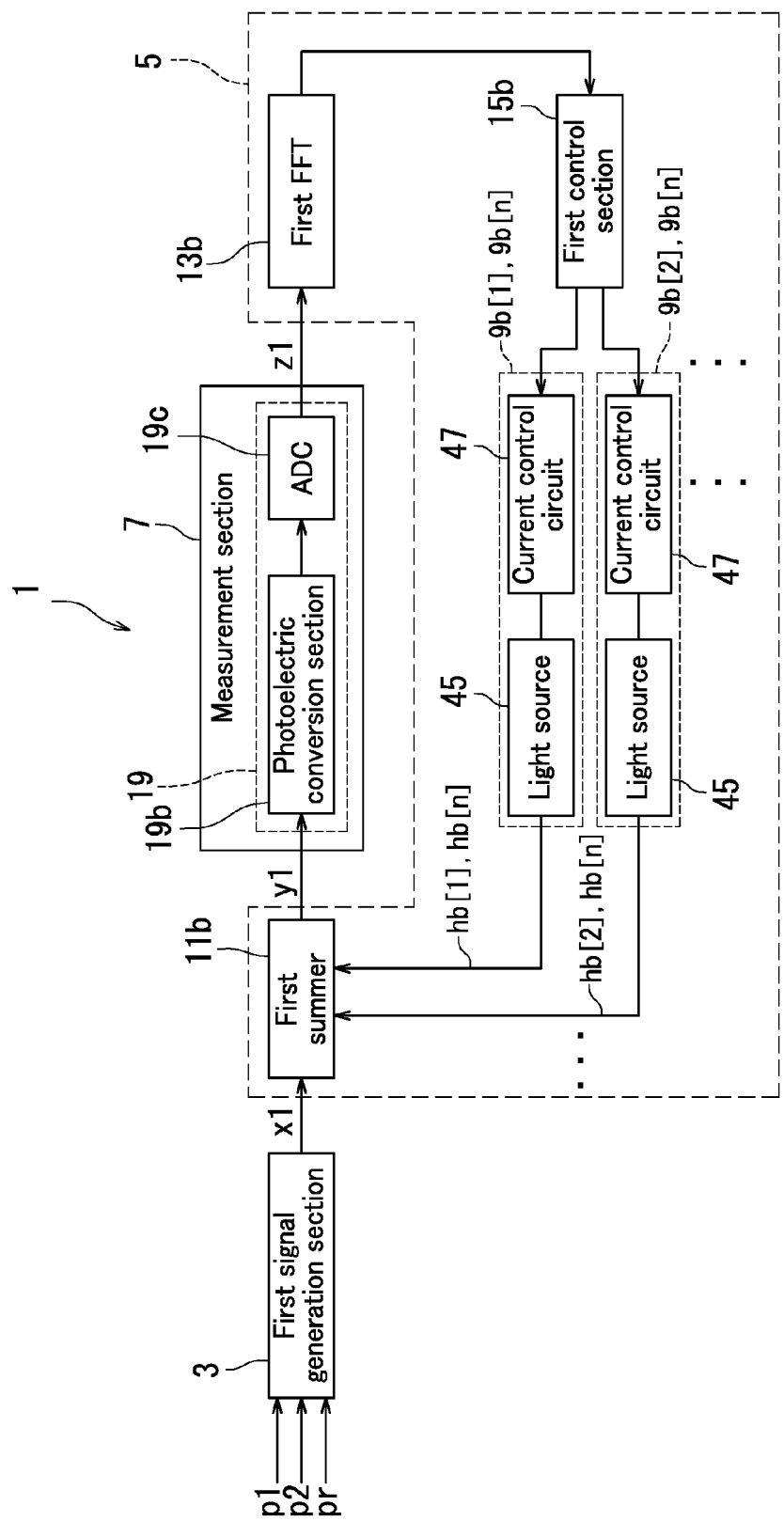
FIG. 14 is a block diagram illustrating a measuring device according to Embodiment 3 of the present invention.

FIG. 14 is a block diagram illustrating the measuring device 1 according to Embodiment 3. The measuring device 1 includes a first signal generation section 3 (first signal generation means), a first removal section 5 (first removal means), and a measurement section 7 (measurement means). An electrical configuration of the measurement section 7 is the same as the electrical configuration of the measurement section 7 illustrated in FIG. 5A. A detector 19 according to Embodiment 3 includes a photoelectric conversion section 19b (photoelectric conversion means) and an analog-digital converter 19c (hereinafter, referred to as an "ADC 19c") (analog-digital conversion section or analog-digital conversion means). The photoelectric conversion section 19b converts a received optical signal to an electric signal. The photoelectric conversion section 19b is for example a photomultiplier tube or an image sensor (for example, a CCD image sensor or a CMOS image sensor). The ADC 19c converts an analog signal to a digital signal.

Light having an optical intensity p1 as the first physical quantity p1, light having an optical intensity p2 as the second physical quantity p2, and light having an optical intensity pr as the reference physical quantity pr are input into the first signal generation section 3. The optical intensity pr according to Embodiment 3 is a level indicative of a dark state.

The first signal generation section 3 generates the staircase first source signal x1(t) through switching among the light having the optical intensity p1, the light having the optical intensity p2, and the light having the optical intensity pr, and outputs the first source signal x1(t) to a first summer 11b. That is, as illustrated in FIG. 2, the first signal generation section 3 emits the light having the optical intensity p1 during the interval from time 0 to time T/4, emits no light during the interval from time T/4 to time 3T/4, and emits light having the optical intensity p2 during the interval from time 3T/4 to time T. The signal generation section 3 repeats such light emission to generate the periodic, staircase first source signal x1(t). The dark state is achieved through the first signal generation section 3 emitting no light.

The first removal section 5 includes N (N representing an integer greater than or equal to one) harmonic generation sections 9b[1] to 9b[N] (harmonic generation means), the first summer 11b, a first fast Fourier transform device 13b (hereinafter, referred to as a "first FFT 13b") (first Fourier transform section or first Fourier transform means), and a first control section 15b (first control means).

The number N of harmonic generation sections 9b[1] to 9b[N] is equal to the number of removal target harmonics in the first source signal x1(t) that are to be removed by the first removal section 5. The harmonic generation sections 9b[1] to 9b[N] respectively generate harmonic optical signals hb[1] to hb[N] and emit them to the first summer 11b.

Herein, the harmonic generation sections 9b[1] to 9b[N] will be collectively referred to as a harmonic generation section 9b[n] (n representing an integer greater than or equal to one), and the harmonic optical signals hb[1] to hb[N] will be collectively referred to as a harmonic optical signal hb[n].

The harmonic optical signal hb[n] has the same frequency as a removal target harmonic among the plurality of harmonics included in the first source signal x1(t).

The harmonic generation section 9b[n] includes a light source 45 and a current control circuit 47. The light source 45 is for example an LED. The current control circuit 47 is controlled by the first control section 15b and controls or chops electric current that is supplied to the light source 45 to control an amount of light that is emitted by the light source 45. As a result, the current control circuit 47 can adjust either or both of the amplitude and the phase of the harmonic optical signal hb[n]. In accordance with the current control circuit 47, the light source 45 generates a square optical signal and emits the signal as the harmonic optical signal hb[n]. The light source 45 may for example be a laser. In such a configuration, the harmonic generation section 9b[n] for example includes an optical system instead of the current control circuit 47. The optical system chops the optical signal output by the light source 45 and having a constant intensity to generate the square optical signal and emits the signal as the harmonic optical signal hb[n].

Non-linearity, which poses a problem when a linearity of for example 10 ppm is to be achieved, is related to intensity distribution in a detection surface of a photodetector. The harmonic generation section 9b[n] therefore generates the harmonic optical signal hb[n] such that the harmonic optical signal hb[n] has the same intensity distribution as the first source signal x1(t) in a detection surface of the photoelectric conversion section 19b.

The summer 11b sums the harmonic optical signal hb[n] and the first source signal x1(t) to output the first summed signal y1(t).

The first summer 11b is for example a bifurcated optical fiber. The bifurcated optical fiber includes a plurality of input optical fibers, an output optical fiber, and an optical coupler that connects the input optical fibers and the output optical fiber. In such a configuration, the first source signal x1(t) is input into one of the input optical fibers. The harmonic optical signal hb[n] is input into the corresponding input optical fiber. As a result, the first source signal x1(t) and the harmonic optical signal hb[n] are summed, and the first summed signal y1(t) is emitted from the output optical fiber.

Alternatively, the first summer 11b for example includes a plurality of stages of half mirror that are in a linear arrangement. In such a configuration, the first source signal x1(t) is input into a first one of the stages of half mirror. The harmonic optical signal hb[n] is input into the corresponding stage of half mirror. As a result, the first source signal x1(t) and the harmonic optical signal hb[n] are summed, and the first summed signal y1(t) is emitted from a last one of the stages of half mirror.

The first summed signal y1(t) is input into the photoelectric conversion section 19b of the detector 19, and the photoelectric conversion section 19b receives the first summed signal y1(t). The photoelectric conversion section 19b converts the first summed signal y1(t), which is an optical signal, to an electric signal and inputs the electric signal into the ADC 19c. The ADC 19c converts the input electric signal, which is an analog signal, to a digital signal and outputs the digital signal as the first measurement signal z1(t). The first FFT 13b performs fast Fourier transform to calculate a plurality of harmonics included in the first measurement signal z1(t).

The first control section 15b causes the harmonic generation section 9b[n] to adjust either or both of the amplitude and the phase of the harmonic optical signal hb[n] so that a harmonic that matches the removal target harmonic is removed from the first measurement signal z1(t). As in Embodiment 1, the control of the harmonic generation section 9b[n] by the first control section 15b, the adjustment of either or both of the amplitude and the phase by the harmonic generation section 9b[n], the summing by the first summer 11a, the photoelectric conversion and the analog-digital conversion by the detector 19, and the Fourier transform by the first FFT 13b are repeated until harmonics that match the removal target harmonics are removed from the first measurement signal z1(t).

As in Embodiment 1, the measurement section 7 includes a phase calculating section 21, a delay calculating section 23, and a first ratio calculating section 25. As in Embodiment 1, the measurement section 7 calculates the value r of the ratio in accordance with the equation (1).

Furthermore, as in Embodiment 1, the measuring device 1 performs the measuring method illustrated by the flow-chart in FIG. 12. In the case of Embodiment 3, the harmonic generation section 9[n] is replaced with the harmonic generation section 9b[n], the harmonic signal h[n] is replaced with the harmonic optical signal hb[n], the first summing section 11 is replaced with the first summer 11b, the first Fourier transform section 13 is replaced with the first FFT 13b, and the first control section 15 is replaced with the first control section 15b in the illustration in FIG. 12.

Figure 15:
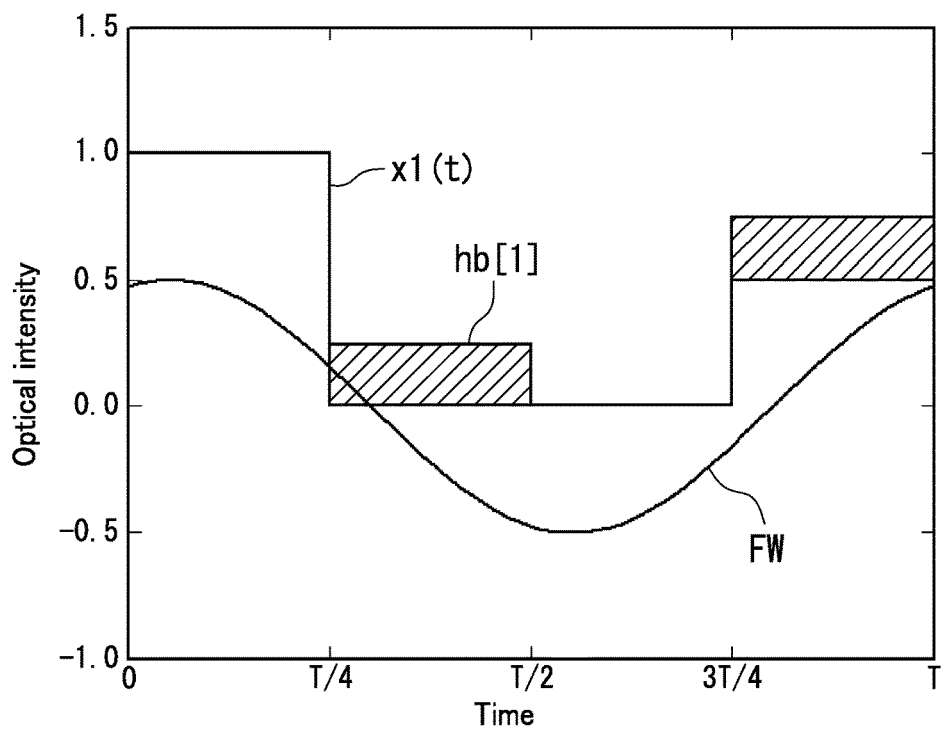
FIG. 15 is a waveform diagram illustrating removal of a second-order harmonic by a first removal section in FIG. 14.

The following describes removal of a harmonic using the harmonic optical signal hb[n] in detail with reference to FIGS. 14 to 17. FIG. 15 is a waveform diagram illustrating removal of a second-order harmonic. FIG. 15 illustrates the first source signal x1(t), a fundamental FW in the first source signal x1(t), and the harmonic optical signal hb[1].

In order to remove the second-order harmonic included in the first source signal x1(t), the harmonic generation section 9b[1] generates the harmonic optical signal hb[1] having the same frequency as the second-order harmonic and outputs the harmonic optical signal hb[1] to the first summer 11b. The harmonic optical signal hb[1] is represented by shaded areas in FIG. 15.

Figure 16:
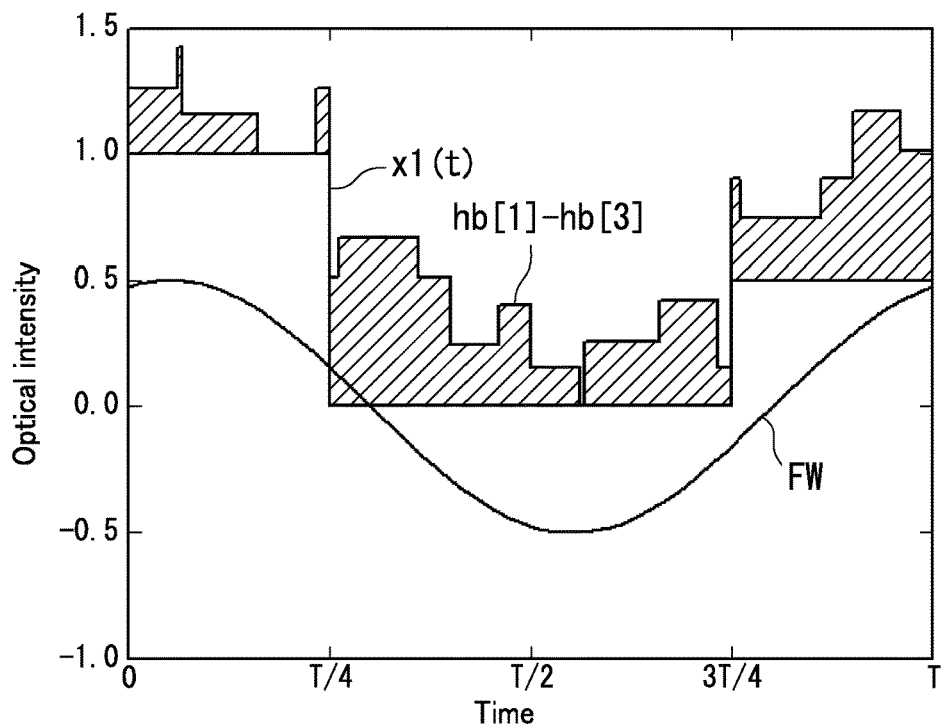
FIG. 16 is a waveform diagram illustrating removal of a second-order harmonic to a fifth-order harmonic by the first removal section in FIG. 14.

FIG. 16 is a waveform diagram illustrating removal of the second-order harmonic, a third-order harmonic, and a fifth-order harmonic. There is no fourth-order harmonic. FIG. 16 illustrates the first source signal x1(t), the fundamental FW of the first source signal x1(t), and the harmonic optical signals hb[1] to hb[3].

In order to remove the second-order harmonic included in the first source signal x1(t), the harmonic generation section 9b[1] generates the harmonic optical signal hb[1] having the same frequency as the second-order harmonic and emits the harmonic optical signal hb[1] to the first summer 11b. In order to remove the third-order harmonic, the harmonic generation section 9b[2] generates the harmonic optical signal hb[2] having the same frequency as the third-order harmonic and emits the harmonic optical signal hb[2] to the first summer 11b. In order to remove the fifth-order harmonic, the harmonic generation section 9b[3] generates the harmonic optical signal hb[3] having the same frequency as the fifth-order harmonic and emits the harmonic optical signal hb[3] to the first summer 11b. The harmonic optical signals hb[1] to hb[3] are represented by shaded areas in FIG. 16.

Figure 17:
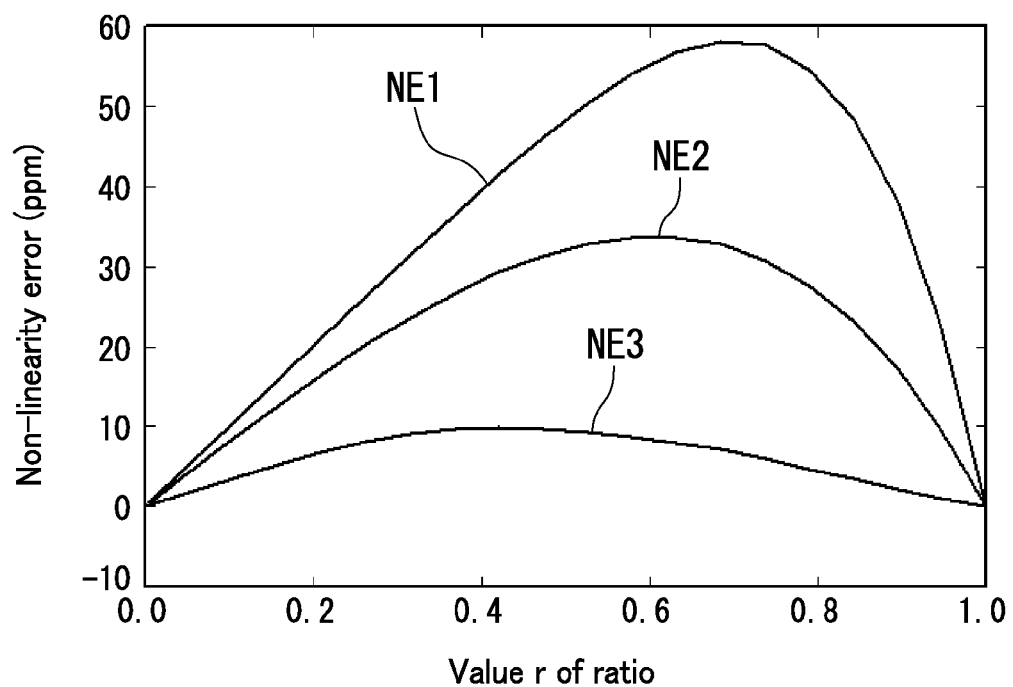
FIG. 17 is a diagram illustrating reduction of a non-linearity error by the measuring device according to Embodiment 3 of the present invention.

FIG. 17 is a diagram illustrating reduction of a non-linearity error by harmonic removal. A curve NE1 represents the non-linearity error in the value r of the ratio in a case where no harmonic is removed. A curve NE2 represents the non-linearity error in the value r of the ratio in a case where the second-order harmonic is removed using the harmonic optical signal hb[1] illustrated in FIG. 15. A curve NE3 represents the non-linearity error in the value r of the ratio in a case where the second-order harmonic, the third-order harmonic, and the fifth-order harmonic are removed using the harmonic optical signals hb[1] to hb[3] illustrated in FIG. 16.

The non-linearity error is less in the case where the second-order harmonic is removed than in the case where no harmonic is removed. The non-linearity error is less in the case where the second-order harmonic, the third-order harmonic, and the fifth-order harmonic are removed than in the case where only the second-order harmonic is removed.

In the simulation illustrated in FIG. 17, because of non-linearity of the photoelectric conversion section 19b, the non-linearity error is made proportional to the sixth power of the optical intensity of the non-linearity error, the first physical quantity p1 is constant, and the second physical quantity p2 ($\leq$p1) is changed. The value r of the ratio is calculated in accordance with the equation (1).

According to Embodiment 3, as described above with reference to FIGS. 14 to 17, influence of non-linearity of the measurement section 7 (the photoelectric conversion section 19b and the ADC 19c) can be reduced by removing some or all of the harmonics from the first measurement signal z1(t) in optical measurement. As a result, a non-linearity error included in the value r of the ratio, that is, an optical intensity ratio can be reduced. In addition to the above, Embodiment 3 also achieves the same effects as Embodiment 1.

The measuring device 1 according to Embodiment 3 can be applied to spectroscopic measurement (ultraviolet, visible, or near-infrared light region). The measuring device 1 is effectively utilized in simultaneous calibration in spectroscopic measurement. Linearity in double-beam spectroscopic measurement can for example be improved. The measuring device 1 can for example be combined with a double-beam spectrophotometer. That is, linearity in double-beam spectroscopic measurement can be improved by inputting light having, as the first physical quantity p1, an optical intensity that has interacted with a measurement sample and light having, as the second physical quantity p2, an optical intensity that has not interacted with the measurement sample into the first signal generation section 3. Furthermore, a spectrophotometer having a linearity of 10 ppm can for example be achieved. Improvement in linearity of the spectrophotometer leads to improvement in precision of quantitative analysis using the spectrophotometer. Furthermore, it is possible to reduce an error in multivariate analysis, which is employed in a case where many signals overlap such as in a case of the near-infrared light region, because the multivariate analysis is performed assuming linearity of a spectrum.

(Embodiment 4)

Figure 18:
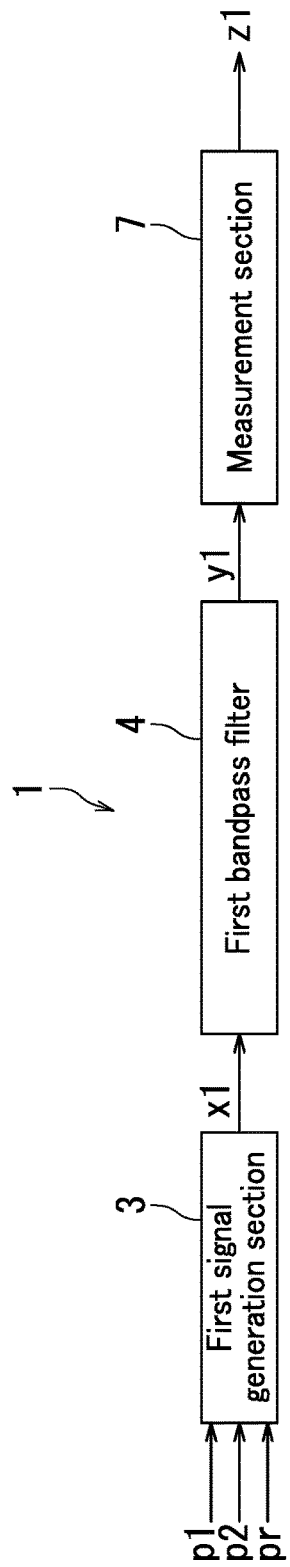
FIG. 18 is a block diagram illustrating a measuring device according to Embodiment 4 of the present invention.

The following describes a measuring device 1 according to Embodiment 4 of the present invention with reference to FIGS. 1 to 18. FIG. 18 is a block diagram illustrating the measuring device 1. The measuring device 1 includes a first bandpass filter 4 (first removal means) instead of the first removal section 5 of the measuring device 1 according to Embodiment 1. The measuring device 1 is utilized in simultaneous calibration.

The first bandpass filter 4 allows only the fundamental in the first source signal x1(t) to pass and outputs the fundamental to the measurement section 7 as a harmonic-removed signal y1(t) (corresponding to the first summed signal y1(t) in Embodiment 1). The measurement section 7 converts the harmonic-removed signal y1(t), which is an analog signal, to the digital first measurement signal z1(t). The measurement section 7 calculates the value r of the ratio in accordance with the equation (1).

The first bandpass filter 4 is for example an analog filter. The first bandpass filter 4 has a configuration that has no influence on the phase of the fundamental in the first source signal x1(t), that is, a configuration that prevents phase shifting between the fundamental in the first source signal x1(t) and the fundamental in the harmonic-removed signal y1(t) and prevents a drift in the phase shifting.

According to Embodiment 4, influence of non-linearity of the measurement section 7 (the detector 19) can be reduced by removing some or all of the harmonics from the first measurement signal z1(t). As a result, a non-linearity error included in the value r of the ratio can be reduced. In addition to the above, Embodiment 4 also achieves the same effects as Embodiment 1.

The measuring device 1 according to Embodiment 4 can be applied to voltage measurement. Accordingly, each of the first physical quantity p1, the second physical quantity p2, and the reference physical quantity pr in FIG. 18 is a voltage. Each of the first source signal x1(t), the harmonic-removed signal y1(t), and the first measurement signal z1(t) is an electric signal.

The measuring device 1 according to Embodiment 4 can also be applied to optical measurement such as spectroscopic measurement. Accordingly, each of the first physical quantity p1, the second physical quantity p2, and the reference physical quantity pr in FIG. 18 is an optical intensity. Each of the first source signal x1(t) and the harmonic-removed signal y1(t) is an optical signal. The first measurement signal z1(t) is an electric signal.

(Embodiment 5)

The following describes a measuring device 1 according to Embodiment 5 of the present invention with reference to FIGS. 1, 5A-5B, 19A-19B, and 20. The measuring devices 1 according to Embodiments 1 to 4 are utilized in simultaneous calibration. In contrast, the measuring device 1 according to Embodiment 5 is utilized not only in simultaneous calibration but also in multipoint calibration. When utilized in multipoint calibration, the measuring device 1 prepares a non-linearity error table in advance and corrects measurement values using the table.

The measuring device 1 according to Embodiment 5 includes the same configuration as the measuring device 1 according to Embodiment 1, and can determine the value r of the ratio while reducing influence of a non-linearity error by removing harmonics. Therefore, a difference between a measurement value determined without performing harmonic removal and a measurement value determined with performing harmonic removal represents the non-linearity error. Accordingly, the measuring device 1 is utilized in multipoint calibration by preparing the non-linearity error table.

The measuring device 1 according to Embodiment 5 has a non-linearity error reduction mode and a non-linearity error measurement mode. The measuring device 1 in the non-linearity error reduction mode operates in the same manner as the measuring device 1 according to Embodiment 1 and is utilized in simultaneous calibration. The following describes the non-linearity error measurement mode and utilization in multipoint calibration. The non-linearity error measurement mode of the measuring device 1 includes a first mode and a second mode.

Figure 19A:
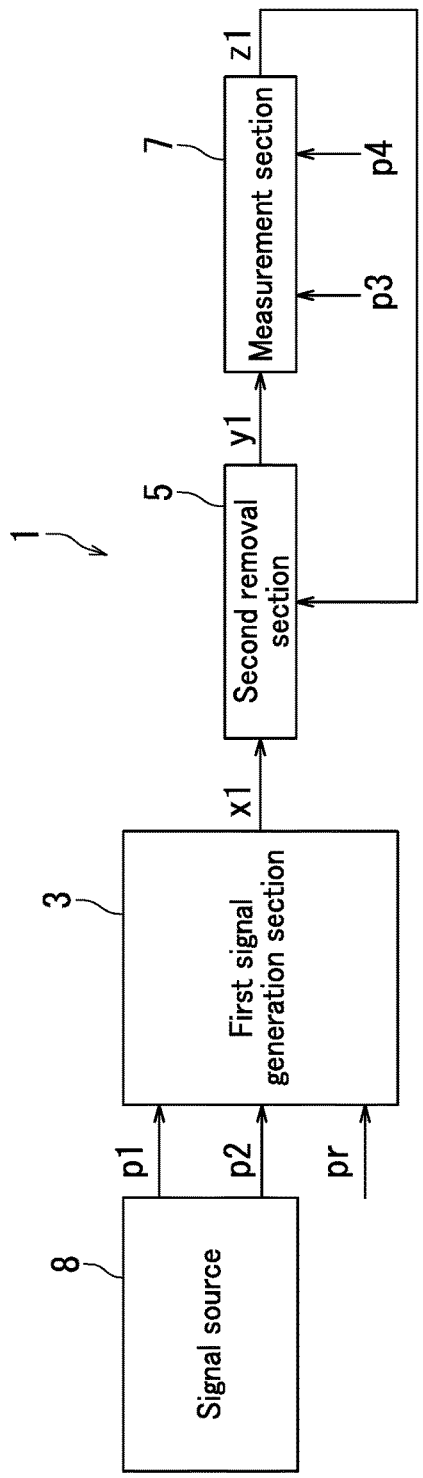
FIG. 19A is a block diagram illustrating a measuring device 1 according to Embodiment 5 of the present invention.

FIG. 19A is a block diagram illustrating the measuring device 1 according to Embodiment 5 of the present invention. The measuring device 1 includes a two-channel signal source 8 in addition to the configuration of the measuring device 1 according to Embodiment 1. The first signal generation section 3, the first removal section 5, and the measurement section 7 respectively have the same configurations as the configurations of the first signal generation section 3, the first removal section 5, and the measurement section 7 of the measuring device 1 according to Embodiment 1. An electrical configuration of the measurement section 7 according to Embodiment 5 is the same as the electrical configuration illustrated in FIG. 5A. However, the measurement section 7 has a different configuration from the configuration illustrated in FIG. 5B.

Figure 20:
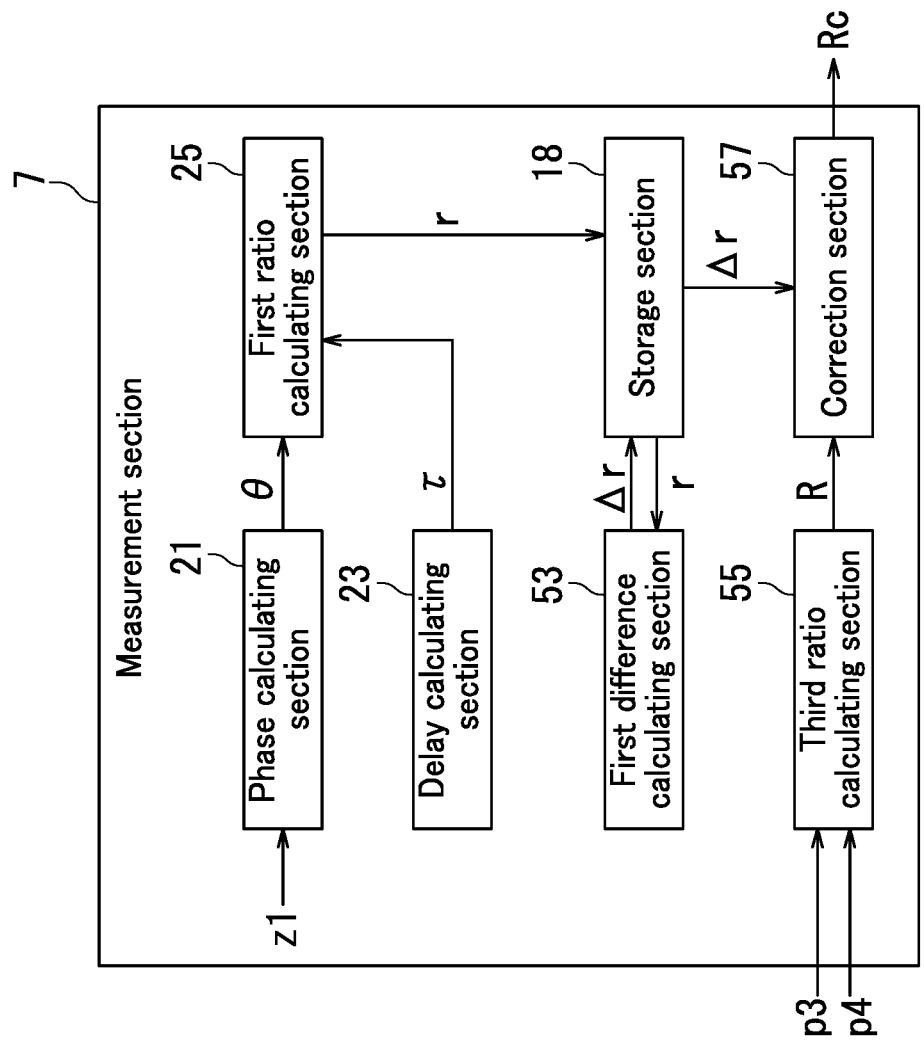
FIG. 20 is a functional block diagram illustrating a measurement section in FIG. 19.

FIG. 20 is a block diagram illustrating the measurement section 7. The measurement section 7 includes a first difference calculating section 53 (first difference calculating means), the storage section 18 (storage means), a third ratio calculating section 55 (third ratio calculating means), and a correction section 57 (correction means) in addition to the configuration of the measurement section 7 illustrated in FIG. 5B.

The processor 17 functions as the phase calculating section 21, the delay calculating section 23, the first ratio calculating section 25, the first difference calculating section 53, the third ratio calculating section 55, and the correction section 57 through execution of a computer program stored in the storage section 18.

The following describes operation of the measuring device 1 in the first mode with reference to FIGS. 1, 19A, and 20. The signal source 8 generates a first signal p1 indicating the first physical quantity p1, maintains the first physical quantity p1 constant, and outputs the first signal p1 to the first signal generation section 3. The first signal p1 is measured in advance to determine an approximate value of the first physical quantity p1. The thus determined first physical quantity p1 includes not only a non-linearity error but also offset and gain errors. The determined value of the first physical quantity p1 is set as an upper limit of the second physical quantity p2.

The signal source 8 also generates a second signal p2 indicating the second physical quantity p2, changes the second physical quantity p2 in a stepwise manner, and outputs the second signal p2 to the first signal generation section 3. Specifically, the signal source 8 changes the second physical quantity p2, and subsequently maintains the second physical quantity p2 constant. Thereafter, once a specific period of time has elapsed, the signal source 8 changes the second physical quantity p2 to a different value, and subsequently maintains the second physical quantity p2 constant. In accordance with the predetermined number of steps for changing the second physical quantity p2, the signal source 8 repeats changing and maintaining of the second physical quantity p2 until the second physical quantity p2 reaches the upper limit. The reference signal pr indicating the reference physical quantity pr is also input into the first signal generation section 3.

The ratio (p2/p1) is stable after the second physical quantity p2 is maintained constant, and a drift therein within the measurement time is negligible. Accuracy of the value of the first physical quantity p1 and the value of the second physical quantity p2 does not need to be high. Furthermore, the ratio (p2/p1) does not need to be known in advance. It should be noted that accuracy indicates a range within which a difference between the measurement value and a standard (for example, an international standard or a national standard) falls. In contrast, precision indicates variability of measurement values when measurement of the same physical quantity is repeated.

The first signal generation section 3 outputs the first source signal x1(t) in which the first physical quantity p1 is maintained constant and the second physical quantity p2 is changed in a stepwise manner. The first summing section 11 of the first removal section 5 sums the harmonic signal h[n] and the first source signal x1(t) to output the first summed signal y1(t). Having the harmonic signal h[n] added thereto, the first summed signal y1(t) is a signal from which a corresponding harmonic has been removed. The measurement section 7 inputs the first summed signal y1(t) and outputs the first measurement signal z1(t) from which the harmonic has been removed. In Embodiment 5, the first measurement signal z1(t) from which the harmonic has been removed is referred to as a first measurement signal z1a(t).

Based on the first measurement signal z1a(t), the first ratio calculating section 25 calculates the value r of the ratio of the second physical quantity p2 to the first physical quantity p1 for each second physical quantity p2. That is, the phase calculating section 21 calculates a phase θ of a fundamental in the first measurement signal z1a(t) for each physical quantity p2. The delay calculating section 23 calculates a delay time τ of the first measurement signal z1a(t). The first ratio calculating section 25 calculates the value r of the ratio in accordance with the equation (1) using the phase θ of the fundamental and the delay time τ of the first measurement signal z1a(t) for each physical quantity p2, and stores the value r of the ratio in the storage section 18. The value r of the ratio includes a reduced non-linearity error, and therefore the accuracy thereof is high. Through the above, the first mode has been described.

The following describes operation of the measuring device 1 in the second mode. Operation of the signal source 8 and the first signal generation section 3 is the same as the operation of the signal source 8 and the first signal generation section 3 in the first mode. The harmonic generation section 9[n] in the first removal section 5 does not generate the harmonic signal h[n]. Accordingly, the first summing section 11 outputs the first source signal x1(t) as the first summed signal y1(t) without summing the harmonic signal h[n] and the first source signal x1(t). Having no harmonic signal h[n] added thereto, the first summed signal y1(t) is a signal from which none of the harmonics has been removed. The measurement section 7 inputs the first summed signal y1(t) and outputs the first measurement signal z1(t) from which none of the harmonics has been removed. In Embodiment 5, the first measurement signal z1(t) from which none of the harmonics has been removed is referred to as a first measurement signal z1b(t).

Based on the first measurement signal z1b(t), the first ratio calculating section 25 calculates the value r of the ratio of the second physical quantity p2 to the first physical quantity p1 for each second physical quantity p2. That is, the phase calculating section 21 calculates the phase θ of the fundamental in the first measurement signal z1b(t) for each second physical quantity p2. The delay calculating section 23 calculates the delay time τ of the first measurement signal z1b(t). The first ratio calculating section 25 calculates the value r of the ratio in accordance with the equation (1) using the phase θ of the fundamental and the delay time τ of the first measurement signal z1b(t) for each physical quantity p2, and stores the value r of the ratio in the storage section 18. The value r of the ratio includes a non-linearity error that is not reduced. Through the above, the second mode has been described.

The first difference calculating section 53 acquires from the storage section 18 the value r of the ratio calculated in the first mode and the value r of the ratio calculated in the second mode for each second physical quantity p2. Subsequently, the first difference calculating section 53 calculates a difference Δr between the value r of the ratio calculated in the first mode and the value r of the ratio calculated in the second mode for each second physical quantity p2. The storage section 18 stores therein the difference Δr in association with the value r of the ratio calculated in the second mode for each second physical quantity p2.

As a result, a table associating the value r of the ratio calculated in the second mode with the difference Δr (hereinafter, referred to as an "error table") is created. The difference Δr represents the non-linearity error, and therefore the error table is a table associating the value r of the ratio calculated in the second mode with the non-linearity error. Preferably, the second physical quantity p2 is changed finely in a sufficiently large number of steps so that data in the error table is sufficiently continuous and sufficiently precise.

Since the error table is prepared, an analog signal p3 indicating a third physical quantity p3 and an analog signal p4 indicating a fourth physical quantity p4 can be input into the measurement section 7. The third physical quantity p3 corresponds to the first physical quantity p1, and the fourth physical quantity p4 corresponds to the second physical quantity p2. The analog signal p3 and the analog signal p4 are optionally input and are measurement targets. The measurement section 7 converts each of the analog signal p3 and the analog signal p4 to a digital signal and calculates a value R (=p4/p3) of a ratio of the fourth physical quantity p4 to the third physical quantity p3. The measurement section 7 then corrects the value R of the ratio using the error table and calculates a value Rc of the ratio including a reduced non-linearity error.

That is, the third ratio calculating section 55 calculates the value R of the ratio. Subsequently, the correction section 57 corrects the value R of the ratio based on the error table, that is, based on the difference Δr stored in the storage section 18 to calculate the value Rc of the ratio. In a case where data is not found in the error table, the non-linearity error is calculated through interpolation. In a case where a drift in the non-linearity error is negligible, the error table may be prepared before the measurement of the third physical quantity p3 and the fourth physical quantity p4, or the error table may be prepared after the measurement of the third physical quantity p3 and the fourth physical quantity p4.

Figure 19B:
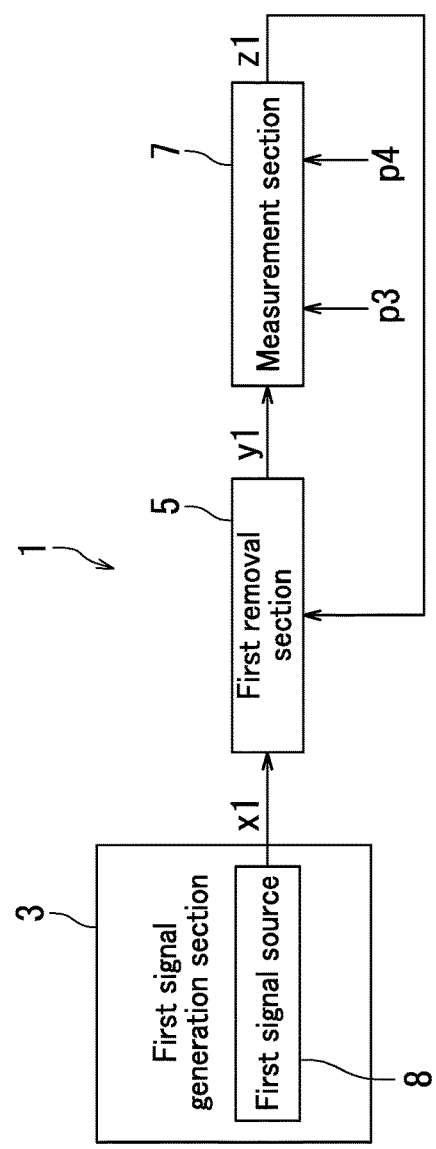
FIG. 19B is a block diagram illustrating the measuring device 1 according to a variation of Embodiment 5 of the present invention.

The following describes a measuring device 1 according to a variation of Embodiment 5 with reference to FIG. 19B. FIG. 19B is a block diagram illustrating the measuring device 1 according to the variation. The measuring device 1 includes a first signal source 8 instead of the signal source 8 of the measuring device 1 illustrated in FIG. 19A. The first signal source 8 is included in the first signal generation section 3. According to the variation, in each of the first and second modes, the first signal source 8 generates and outputs the first source signal x1(t) in which the first physical quantity p1 is maintained constant and the second physical quantity p2 is changed in a stepwise manner.

According to Embodiment 5 (hereinafter, including the variation thereof), as described above with reference to FIGS. 19A-19B and 20, it is possible to easily determine the value r of the ratio including a non-linearity error reduced through harmonic removal and the value r of the ratio including a non-linearity error that is not reduced. Therefore, the error table for achieving utilization in multipoint calibration can be easily prepared.

Furthermore, according to Embodiment 5, the value R of the ratio can be corrected using the error table. Therefore, it is not necessary to generate the first source signal x1(t) and it is not necessary to perform harmonic removal. As a result, the third physical quantity p3 and the fourth physical quantity p4, which fluctuate, can be measured.

Furthermore, the first signal generation section 3, the first removal section 5, and the measurement section 7 in Embodiment 5 can be replaced with the first signal generation section 3, the first removal section 5, and the measurement section 7 according to Embodiment 2. That is, the measuring device 1 according to Embodiment 5 can be applied to voltage measurement. Accordingly, for example an alternating current voltage meter or a high-speed voltage meter can be formed using the measuring device 1, and thus linearity of the alternating current voltage meter or the high-speed voltage meter can be improved.

Furthermore, the first signal generation section 3, the first removal section 5, and the measurement section 7 in Embodiment 5 can be replaced with the first signal generation section 3, the first removal section 5, and the measurement section 7 according to Embodiment 3. That is, the measuring device 1 according to Embodiment 5 can be applied to optical measurement. It is therefore possible to for example correct non-linearity of a light measuring device using the error table. The light measuring device is for example a double-beam spectrophotometer or a multi-channel optical meter (including a camera) such as a CCD image sensor and a CMOS image sensor. Non-linearity can be evaluated through comparison between an optical detection system having high linearity and an optical detection system having low linearity. Provision of a plurality of light sources such as LEDs that enable easy switching allows utilization in multipoint calibration.

(Embodiment 6)

The following describes a measuring device 1 according to Embodiment 6 of the present invention with reference to FIGS. 21 to 24. Unlike the measuring device according to Embodiment 1, in which a one-channel staircase signal (the first source signal x1(t)) is generated, the measuring device 1 according to Embodiment 6 generates a two-channel staircase signal (the first source signal x1(t) and a second source signal x2(t)). The measuring device 1 is utilized in simultaneous calibration. The following mainly describes differences between Embodiment 6 and Embodiment 1.

Figure 21:
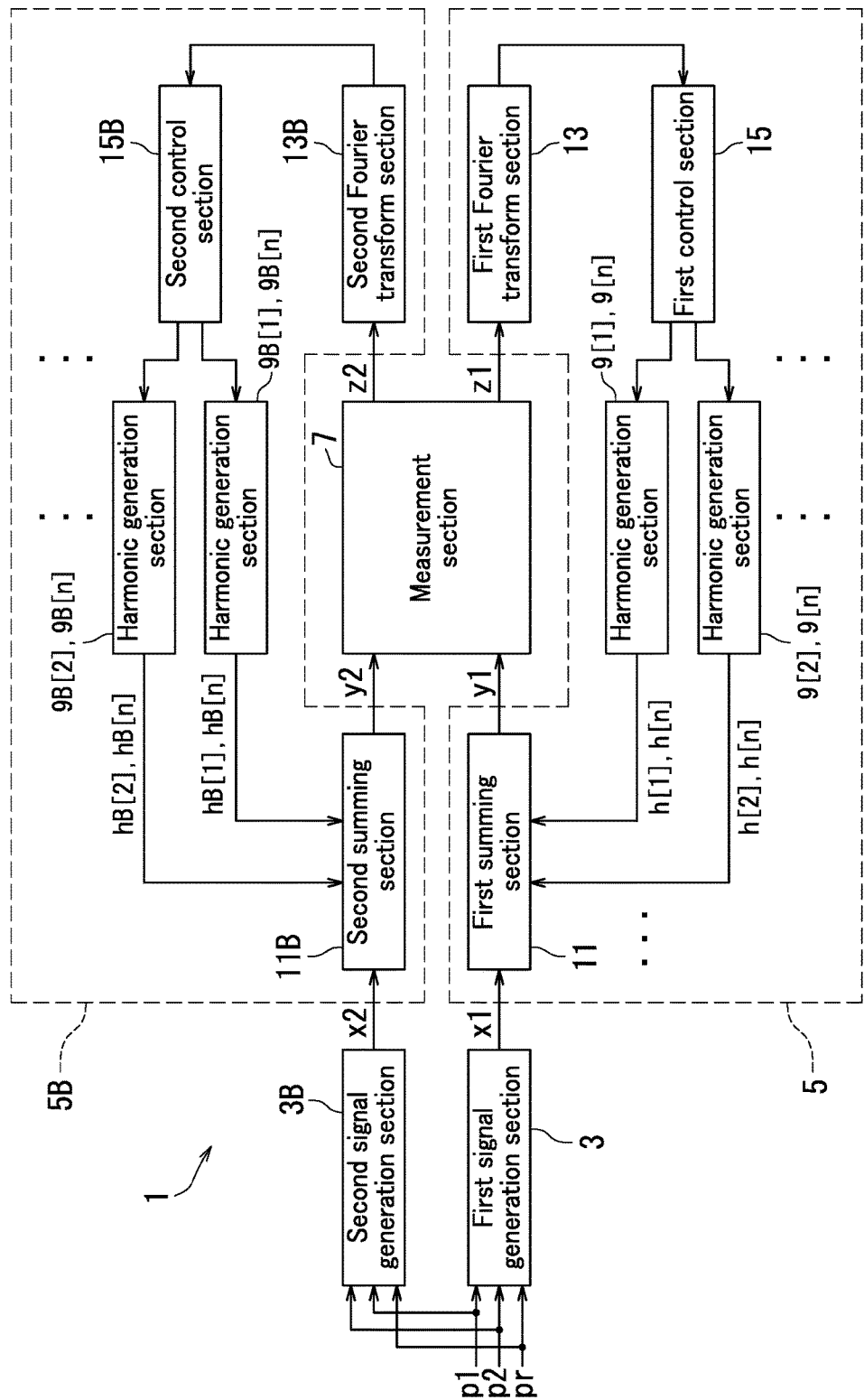
FIG. 21 is a block diagram illustrating a measuring device according to Embodiment 6 of the present invention.

FIG. 21 is a block diagram illustrating the measuring device 1 according to Embodiment 6. The measuring device 1 includes a second signal generation section 3B (second signal generation means) and a second removal section 5B (second removal means) in addition to the configuration of the measuring device 1 according to Embodiment 1.

Figure 22A:
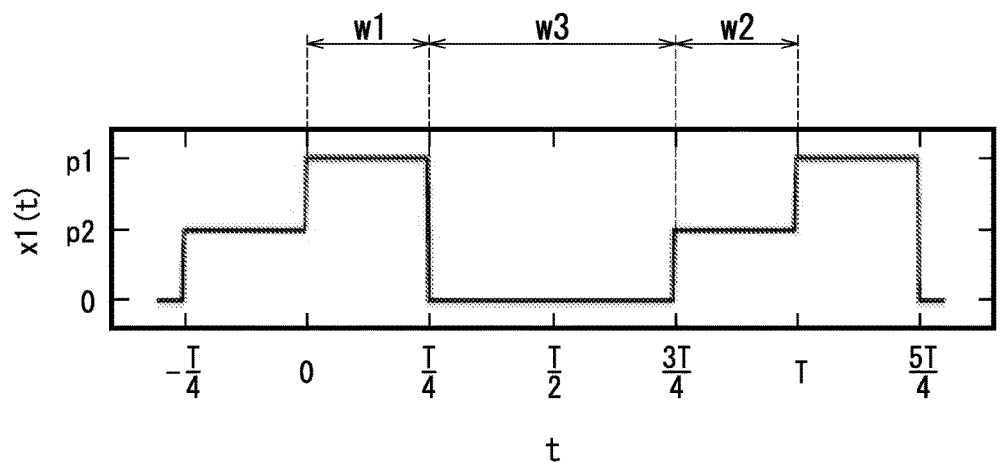
FIG. 22A is a waveform diagram illustrating a first source signal generated by a first signal generation section in FIG. 21.
Figure 22B:
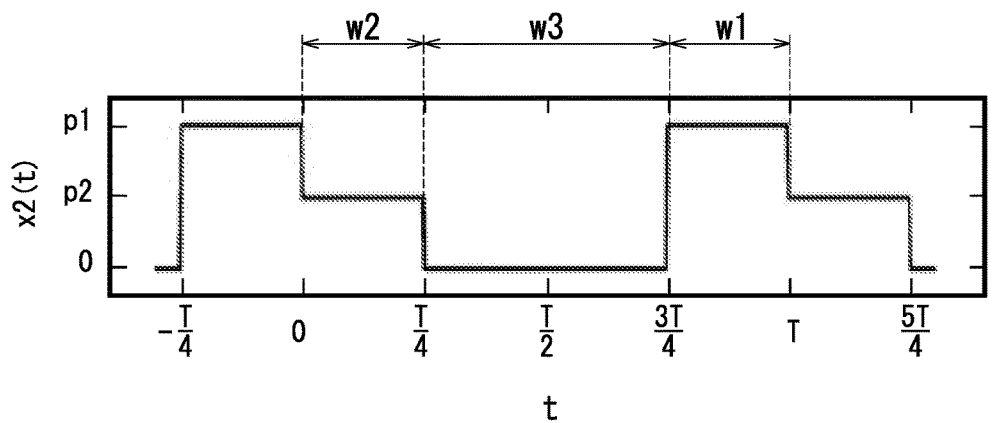
FIG. 22B is a waveform diagram illustrating a second source signal generated by a second signal generation section in FIG. 21A.

The second signal generation section 3B generates the second source signal x2(t) including a fundamental and a plurality of harmonics. FIG. 22A is a waveform diagram illustrating the first source signal x1(t). FIG. 22B is a waveform diagram illustrating the second source signal x2(t). The second source signal x2(t) has a waveform of the first source signal x1(t) with the first physical quantity p1 and the second physical quantity p2 interchanged.

That is, one period of the second source signal x2(t) includes the second signal p2 indicating the second physical quantity p2, the reference signal pr indicating the reference physical quantity pr, and the first signal p1 indicating the first physical quantity p1. The second signal p2 has the second duration w2 (=(¼) period) from time 0 to time T/4. The reference signal pr has the third duration w3 (=(2/4) period) from time T/4 to time 3T/4. The first signal p1 has the first duration w1 (=(¼) period) from time 3T/4 to time T. Furthermore, the frequency of the fundamental in the second source signal x2(t) is equal to the frequency f (=1/T) of the fundamental in the first source signal x1(t). The frequencies of the harmonics in the second source signal x2(t) are respectively equal to the frequencies of the harmonics in the first source signal x1(t).

Referring back to FIG. 21, the second removal section 5B removes some or all of the harmonics from the second source signal x2(t).

The second removal section 5B includes N (N representing an integer greater than or equal to one) harmonic generation sections 9B[1] to 9B[N] (harmonic generation means), a second summing section 11B (second summing means), a second Fourier transform section 13B (second Fourier transform section or second Fourier transform means), and a second control section 15B (second control means). Configurations of the harmonic generation sections 9B[1] to 9B[N], the second summing section 11B, the second Fourier transform section 13B, and the second control section 15B are respectively the same as the configurations of the harmonic generation sections 9[1] to 9[N], the first summing section 11, the first Fourier transform section 13, and the first control section 15.

That is, the harmonic generation sections 9B[1] to 9B[N] respectively generate harmonic signals hB[1] to hB[N].

Herein, the harmonic generation sections 9B [1] to 9B [N] will be collectively referred to as a harmonic generation section 9B [n] (n representing an integer greater than or equal to one), and the harmonic signals hB[1] to hB[N] will be collectively referred to as a harmonic signal hB[n].

The harmonic signal hB [n] has the same frequency as a removal target harmonic among the plurality of harmonics included in the second source signal x2(t). The removal target harmonic that is to be removed by the second removal section 5B is the same as the removal target harmonic that is to be removed by the first removal section 5.

The second summing section 11B sums the harmonic optical signal hB[n] and the second source signal x2(t) to output a second summed signal y2(t). The fundamental and the harmonics in the second summed signal y2(t) respectively have the same frequencies as the fundamental and the harmonics in the second source signal x2(t).

The measurement section 7 outputs the first summed signal y1(t), which is an analog signal, as the digital first measurement signal z1(t) and outputs the second summed signal y2(t), which is an analog signal, as a digital second measurement signal z2(t). An electrical configuration of the measurement section 7 is the same as the electrical configuration illustrated in FIG. 5A. A detector 19 in Embodiment 6 is a two-channel detector. The fundamental and the harmonics in the second measurement signal z2(t) respectively have the same frequencies as the fundamental and the harmonics in the second source signal x2(t).

The second Fourier transform section 13B calculates a plurality of harmonics included in the second measurement signal z2(t) through Fourier transform of the second measurement signal z2(t). The second control section 15B causes the harmonic generation section 9B [n] to adjust either or both of an amplitude and a phase of the harmonic signal hB [n] so that a harmonic that matches the removal target harmonic is removed from the second measurement signal z2(t).

The second summing section 11B sums the second source signal x2(t) and the harmonic signal hB [n] having either or both of an adjusted amplitude and an adjusted phase to output the second summed signal y2(t). The second summed signal y2(t) is converted by the measurement section 7 to the second measurement signal z2(t), and the second measurement signal z2(t) is re-input into the second Fourier transform section 13B.

The Fourier transform by the second Fourier transform section 13B, the control of the harmonic generation section 9B[n] by the second control section 15B, the adjustment of either or both of the amplitude and the phase by the harmonic generation section 9B[n], the summing by the second summing section 11B, and the digital output by the measurement section 7 are repeated until harmonics that match the removal target harmonics are removed from the second measurement signal z2(t).

Figure 23:
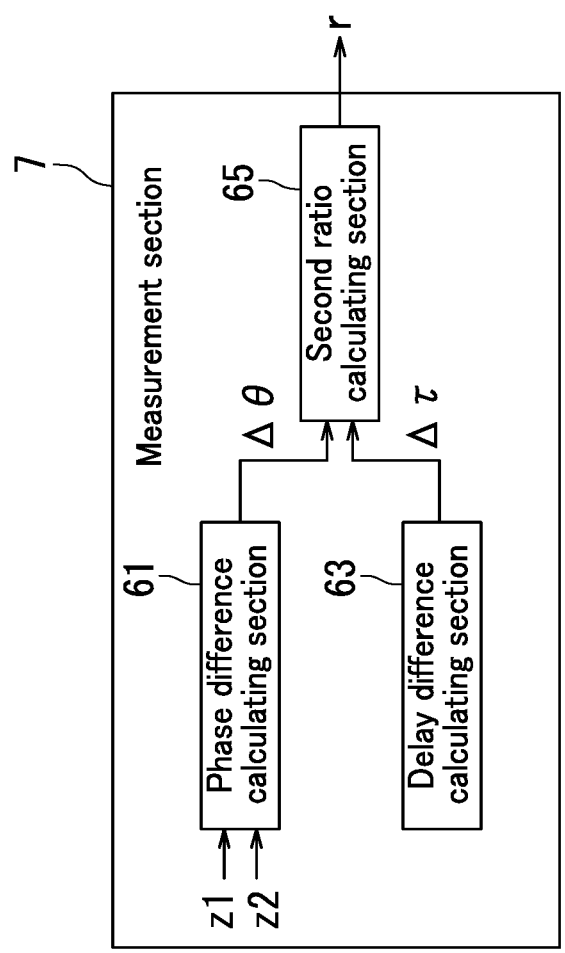
FIG. 23 is a functional block diagram illustrating the measurement section in FIG. 21.

The following describes a method for calculating the value r of the ratio of the second physical quantity p2 to the first physical quantity p1 with reference to FIG. 23. The measurement section 7 calculates the value r of the ratio. FIG. 23 is a functional block diagram of the measurement section 7. The measurement section 7 includes a phase difference calculating section 61 (phase difference calculating means), a delay difference calculating section 63 (delay difference calculating means), and a second ratio calculating section 65 (second ratio calculating means). The processor 17 functions as the phase difference calculating section 61, the delay difference calculating section 63, and the second ratio calculating section 65 through execution of a computer program stored in the storage section 18.

Based on a phase difference Δθ between the fundamental in the first measurement signal z1(t) and the fundamental in the second measurement signal z2(t), the second ratio calculating section 65 calculates the value r of the ratio of the second physical quantity p2 to the first physical quantity p1. That is, the phase difference calculating section 61 calculates the phase difference Δθ. The phase difference Δθ in Embodiment 6 represents shifting of the phase of the fundamental in the second measurement signal z2(t) relative to the phase of the fundamental in the first measurement signal z1(t). The delay difference calculating section 63 calculates a delay time difference2(t). The delay time difference Δτ in Embodiment 6 represents a difference between the delay time of the first measurement signal z1(t) and the delay time of the second measurement signal z2(t). The second ratio calculating section 65 calculates the value r of the ratio in accordance with an equation (2). In the equation (2), pr represents reference physical quantity, and f represents frequency of the fundamental in the first measurement signal z1(t). In Embodiment 6, pr=0.

[Formula 5]

$$r = \frac{p2 - pr}{p1 - pr} = \tan\left(\frac{\pi}{4} + \Delta\theta + \frac{2\pi f \Delta\tau}{2}\right) \quad (2)$$

The delay time difference Δτ can be determined by determining the phase difference Δθ in advance on the assumption that p1=p2 in the equation (2).

Figure 24:
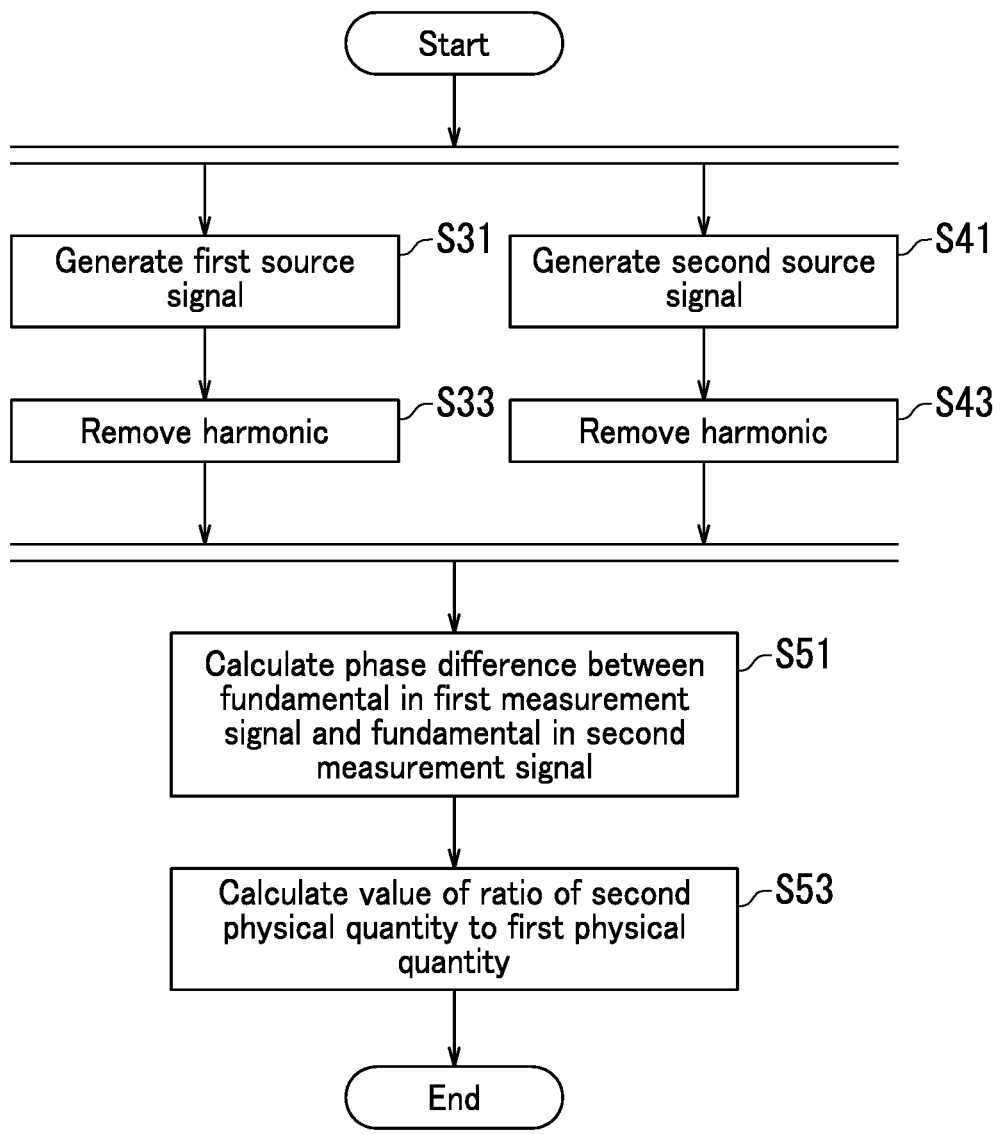
FIG. 24 is a flowchart illustrating a measuring method that is performed by the measuring device according to Embodiment 6 of the present invention.

The following describes a flow of a measuring method that is performed by the measuring device 1 with reference to FIGS. 21, 23, and 24. FIG. 24 is a flowchart illustrating the measuring method. The measuring device 1 performs processes in steps S31 to S53. The process in Step S31 is the same as the process in Step S1 in FIG. 12. The process in Step S33 is the same as the process in Step S3 in FIG. 12 and includes Steps S5 to S15 illustrated in FIG. 12.

That is, in Step S31, the first signal generation section 3 generates the first source signal x1(t). In Step S33, the first removal section 5 removes some or all of the harmonics from the first source signal x1(t).

Meanwhile, in Step S41, the second signal generation section 3B generates the second source signal x2(t). In Step S43, the second removal section 5B removes some or all of the harmonics from the second source signal x2(t).

The process in Step S43 includes the processes in Steps S5 to S15 illustrated in FIG. 12. In the case of Step S43, the harmonic signal h[n] is replaced with the harmonic signal hB[n], the first source signal x1(t) is replaced with the second source signal x2(t), the first summed signal y1(t) is replaced with the second summed signal y2(t), the first measurement signal z1(t) is replaced with the second measurement signal z2(t), the harmonic generation section 9[n] is replaced with the harmonic generation section 9B [n], the first summing section 11 is replaced with the second summing section 11B, the first Fourier transform section 13 is replaced with the second Fourier transform section 13B, and the first control section 15 is replaced with the second control section 15B in the description of Steps S5 to S15.

In Step S51, the phase difference calculating section 61 calculates the phase difference Δθ between the fundamental in the first measurement signal z1(t) and the fundamental in the second measurement signal z2(t). In Step S53, the second ratio calculating section 65 calculates the value r of the ratio of the second physical quantity p2 to the first physical quantity p1 in accordance with the equation (2). It should be noted that the delay difference calculating section 63 calculates in advance the delay time difference Δτ based on the phase difference Δθ when p1=p2 in accordance with the equation (2).

According to Embodiment 6, as described above with reference to FIGS. 21 to 24, influence of non-linearity of the measurement section 7 (the detector 19) on measurement results can be easily reduced by removing some or all of the harmonics, which are a cause of occurrence of a non-linearity error. In addition to the above, Embodiment 6 also achieves the same effects as Embodiment 1.

Furthermore, according to Embodiment 6, the value r of the ratio is calculated from the phase difference Δθ, and thus a task of searching for a reference point on the time axis for calculating the phase θ of the fundamental in the first measurement signal z1(t) can be omitted. Furthermore, there is no dead time.

The measuring device 1 according to Embodiment 6 can also be applied to voltage measurement and optical measurement. It is therefore possible to reduce a non-linearity error in the voltage ratio and the optical intensity ratio. In a case where the measuring device 1 is applied to voltage measurement, each of the first signal generation section 3 and the second signal generation section 3B has the same configuration as the configuration of the first signal generation section 3 according to Embodiment 2, each of the first removal section 5 and the second removal section 5B has the same configuration as the configuration of the first removal section 5 according to Embodiment 2, and the measurement section 7 has the same configuration as the configuration of the measurement section 7 according to Embodiment 2. In a case where the measuring device 1 is applied to optical measurement, each of the first signal generation section 3 and the second signal generation section 3B has the same configuration as the configuration of the first signal generation section 3 according to Embodiment 3, each of the first removal section 5 and the second removal section 5B has the same configuration as the configuration of the first removal section 5 according to Embodiment 3, and the measurement section 7 has the same configuration as the configuration of the measurement section 7 according to Embodiment 3.

(Embodiment 7)

Figure 25:
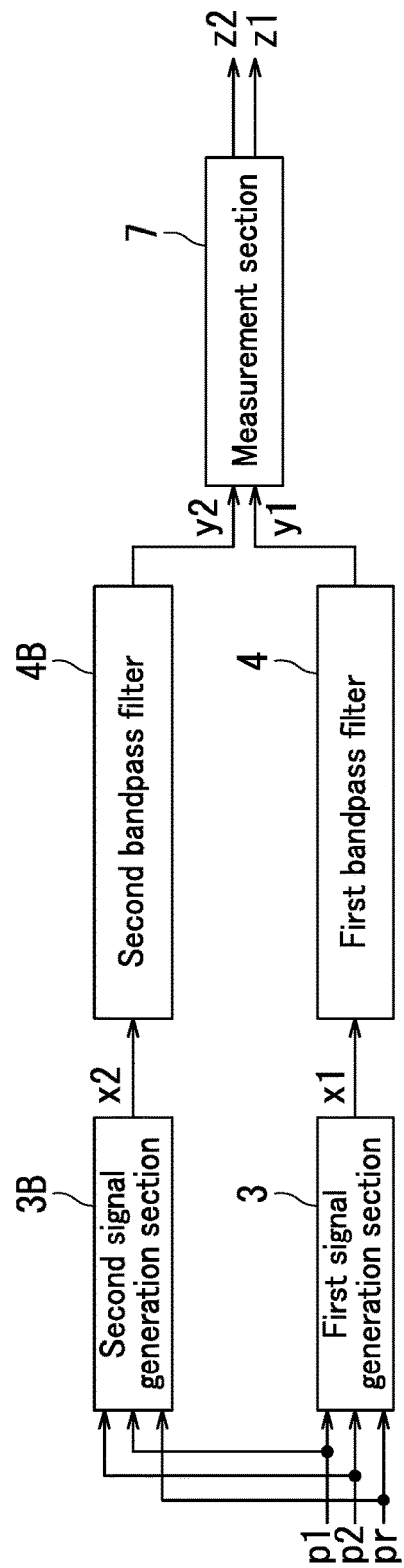
FIG. 25 is a block diagram illustrating a measuring device 1 according to Embodiment 7 of the present invention.

The following describes a measuring device 1 according to Embodiment 7 of the present invention with reference to FIGS. 21 to 25. FIG. 25 is a block diagram illustrating the measuring device 1 according to Embodiment 7. The measuring device 1 includes a first bandpass filter 4 (first removal means) and a second bandpass filter 4B (second removal means) instead of the first removal section 5 and the second removal section 5B of the measuring device 1 according to Embodiment 6. The first bandpass filter 4 has the same configuration as the configuration of the first bandpass filter 4 illustrated in FIG. 18.

The second bandpass filter 4B has the same properties as the first bandpass filter 4; the second bandpass filter 4B allows only the fundamental in the second source signal x2(t) to pass and outputs the fundamental to the measurement section 7 as a harmonic-removed signal y2(t) (corresponding to the second summed signal y2(t) in Embodiment 6).

The measurement section 7 converts the harmonic-removed signal y1(t), which is an analog signal, to the digital first measurement signal z1(t), and converts the harmonic-removed signal y2(t), which is an analog signal, to the digital second measurement signal z2(t). The measurement section 7 calculates the value r of the ratio in accordance with the equation (2).

According to Embodiment 7, influence of non-linearity of the measurement section 7 (the detector 19) can be reduced by removing some or all of the harmonics from the first measurement signal z1(t) and some or all of the harmonics from the second measurement signal z2(t). As a result, a non-linearity error included in the value r of the ratio can be reduced. In addition to the above, Embodiment 7 also achieves the same effects as Embodiment 6. The measuring device 1 can also be applied to voltage measurement and optical measurement.

(Embodiment 8)

The following describes a measuring device 1 according to Embodiment 8 of the present invention with reference to FIGS. 21 and 26 to 28. As the measuring device 1 according to Embodiment 8, the measuring device 1 according to Embodiment 6 illustrated in FIG. 21 is applied to voltage measurement. Accordingly, each of the first physical quantity p1, the second physical quantity p2, and the reference physical quantity pr in FIG. 21 is a voltage. Each of the first source signal x1(t), the first summed signal y1(t), the first measurement signal z1(t), the harmonic signal h[n], the second source signal x2(t), the second summed signal y2(t), the second measurement signal z2(t), and the harmonic signal hB[n] is an electric signal. Each of the first removal section 5 and the second removal section 5B in Embodiment 8 removes only a second-order harmonic. Therefore, N=1. The measuring device 1 is utilized in simultaneous calibration.

Figure 26:
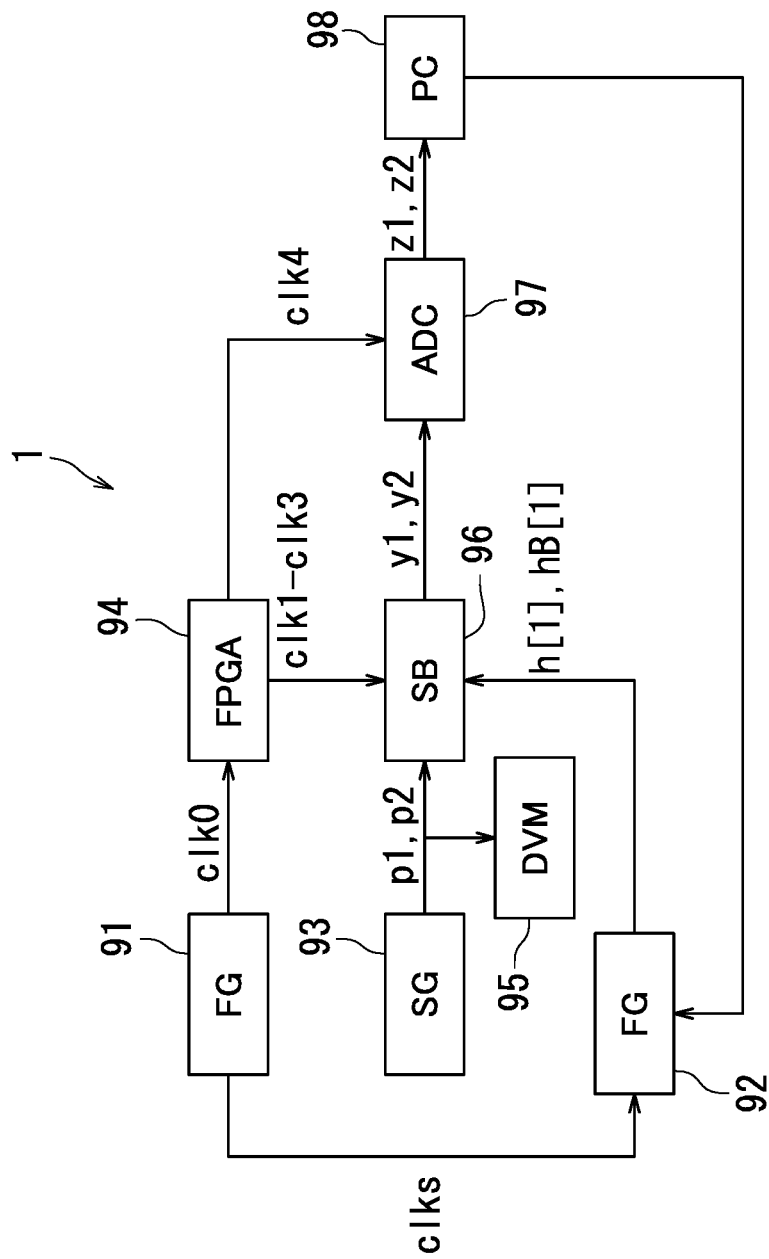
FIG. 26 is a block diagram illustrating a measuring device 1 according to Embodiment 8 of the present invention.

FIG. 26 is a block diagram illustrating the measuring device 1 according to Embodiment 8. The measuring device 1 includes a function generator 91 (hereinafter, referred to as an "FG 91", a function generator 92 (hereinafter referred to as an "FG 92"), a two-channel signal generator 93 (hereinafter, referred to as an "SG 93"), an FPGA 94, a digital voltmeter 95 (hereinafter, referred to as a "DVM 95", a switching board 96 (hereinafter, referred to as an "SB 96"), a two-channel analog-digital converter 97 (hereinafter, referred to as an "ADC 97"), and a personal computer 98 (hereinafter, referred to as a "PC 98").

The FG 91 supplies a base clock clk0 to the FPGA 94 and supplies a synchronous clock clks to the FG 92.

The FG2 operates in synchronization with the synchronous clock clks and generates the harmonic electric signal h[1] and the harmonic electric signal hB[1]. Each of the harmonic electric signal h[1] and the harmonic electric signal hB[1] has the same frequency as the second-order harmonic. The FG 92 functions as the harmonic generation section 9[1] and the harmonic generation section 9B[1].

The SG 93 generates a direct current voltage p1 as the first physical quantity p1 and a direct current voltage p2 as the second physical quantity p2. The FPGA 94 generates clocks clk1 to clk3 and a sampling clock clk4 based on the base clock clk0. The DVM 95 is a voltmeter and measures the direct current voltage p1 and the direct current voltage p2.

The SB 96 functions as the first signal generation section 3, the second signal generation section 3B, the first summing section 11, and the second summing section 11B. The SB 96 generates the first source signal x1(t) and the second source signal x2(t). The SB 96 further generates the first summed signal y1(t) and the second summed signal y2(t).

The ADC 97 converts the first summed signal y1(t), which is an analog signal, to a digital signal and outputs the digital signal as the first measurement signal z1(t) to the PC 98. The ADC 97 also converts the second summed signal y2(t), which is an analog signal, to a digital signal and outputs the digital signal as the second measurement signal z2(t) to the PC 98. The ADC 97 functions as the detector 19 (FIG. 5A).

The PC 98 functions as parts of the measurement section 7 (the phase difference calculating section 61, the delay difference calculating section 63, and the second ratio calculating section 65). The PC 98 measures the first measurement signal z1(t) and the second measurement signal z2(t), and calculates the value r of the ratio in accordance with the equation (2). The PC 98 also functions as the first Fourier transform section 13, the second Fourier transform section 13B, the first control section 15, and the second control section 15B.

Figure 27:
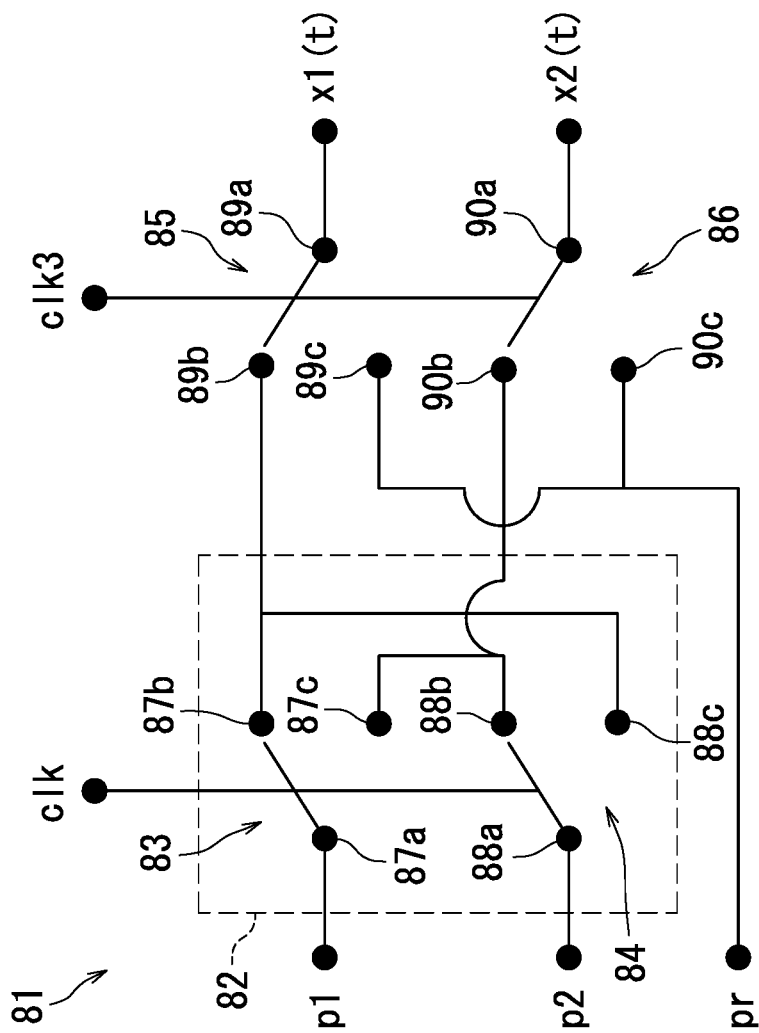
FIG. 27 is a conceptual diagram of a signal generation circuit that is mounted in a switching board in FIG. 26.

FIG. 27 is a schematic diagram of a signal generation circuit 81 that is mounted in the SB 96 illustrated in FIG. 26. The signal generation circuit 81 functions as the first signal generation section 3 and the second signal generation section 3B. The signal generation circuit 81 includes a switch section 82, a switch 85, and a switch 86.

The switch 85 is driven by the clock clk3 and includes contacts 89a to 89c. The switch 86 is driven by the clock clk3 and includes contacts 90a to 90c. The contact 89c is connected with the contact 90c. A voltage of 0 V is applied as the reference physical quantity pr to each of the contact 89c and the contact 90c. That is, the contact 89c and the contact 90c are grounded.

The switch section 82 is driven by the clock clk and includes a switch 83 and a switch 84. The clock clk in Embodiment 8 includes the clocks clk1 and clk2. The switch 83 includes contacts 87a to 87c. The switch 84 includes contacts 88a to 88c. The contact 87b, the contact 88c, and the contact 89b are connected with one another. The contact 87c, the contact 88b, and the contact 90b are connected with one another. The direct current voltage p1 is applied to the contact 87a, and the direct current voltage p2 is applied to the contact 88a.

The switch 83 and the switch 84 operate in synchronization. Thus, the switch 84 connects the contact 88a with the contact 88b when the switch 83 connects the contact 87a with the contact 87b. The switch 84 connects the contact 88a with the contact 88c when the switch 83 connects the contact 87a with the contact 87c.

The switch 85 and the switch 86 operate in synchronization. Thus, the switch 86 connects the contact 90a with the contact 90b when the switch 85 connects the contact 89a with the contact 89b. The switch 86 connects the contact 90a with the contact 90c when the switch 85 connects the contact 89a with the contact 89c.

The following describes operation of the signal generation circuit 81 with reference to FIGS. 22 and 27. During an interval from time 0 to time T/4, the contact 87a and the contact 87b are connected, the contact 89a and the contact 89b are connected, the contact 88a and the contact 88b are connected, and the contact 90a and the contact 90b are connected. Accordingly, the level of the first source signal x1(t) becomes the level of the direct current voltage p1, and the level of the second source signal x2(t) becomes the level of the direct current voltage p2.

During an interval from time T/4 to time 3T/4, the contact 89a and the contact 89c are connected, and the contact 90a and the contact 90c are connected. Accordingly, the level of the first source signal x1(t) and the level of the second source signal x2(t) each become 0 V.

During an interval from time 3T/4 to time T, the contact 88a and the contact 88c are connected, the contact 89a and the contact 89b are connected, the contact 87a and the contact 87c are connected, and the contact 90a and the contact 90b are connected. Accordingly, the level of the first source signal x1(t) becomes the level of the direct current voltage p2, and the level of the second source signal x2(t) becomes the level of the direct current voltage p1.

Figure 28:
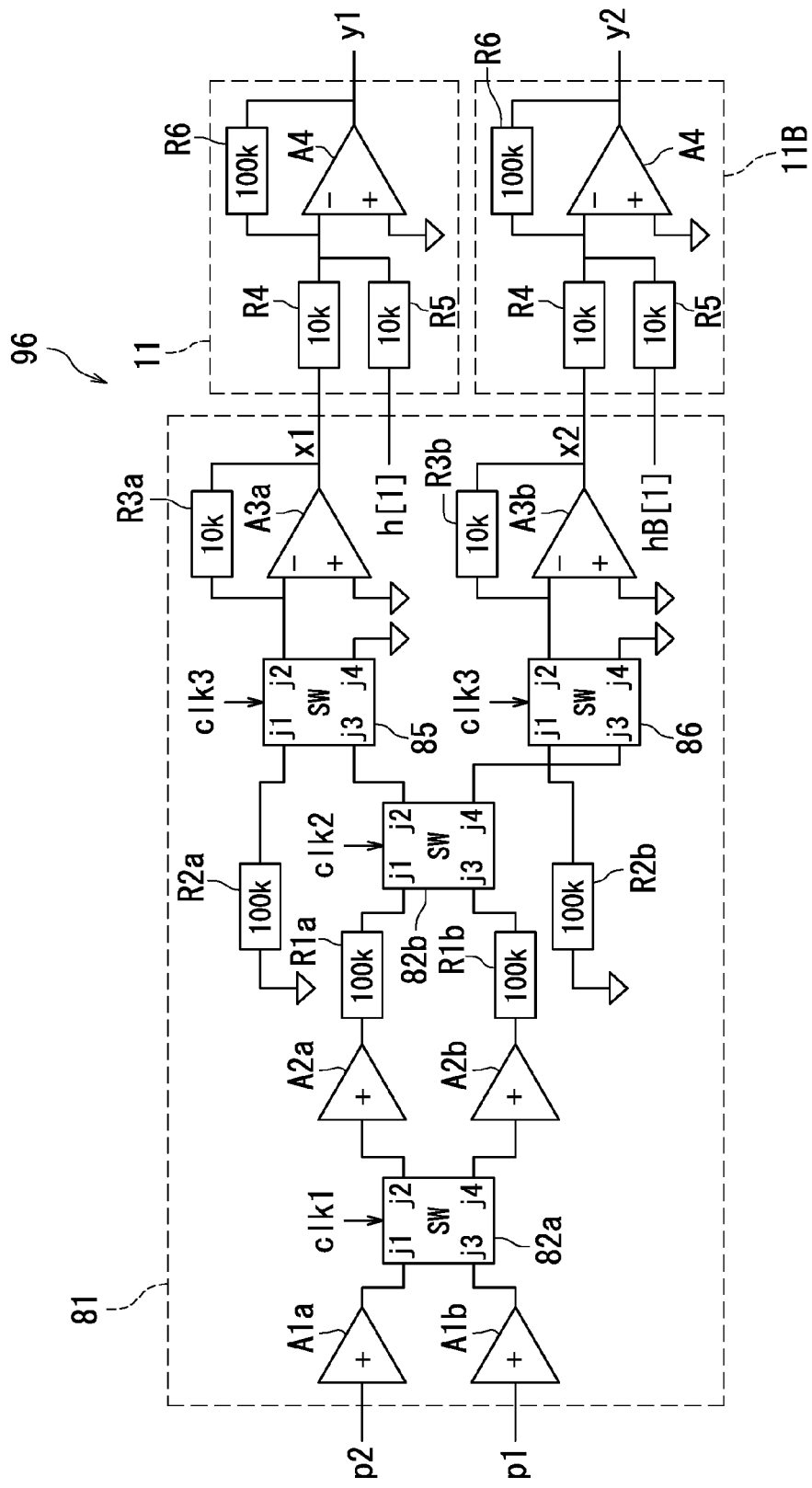
FIG. 28 is a circuit diagram illustrating the switching board in FIG. 26.

The following describes the SB 96 in detail with reference to FIG. 28. FIG. 28 is a circuit diagram illustrating the SB 96. The SB 96 includes the signal generation circuit 81, the first summing section 11, and the second summing section 11B. The signal generation circuit 81 illustrated in FIG. 27 is implemented as the signal generation circuit 81 illustrated in FIG. 28. The signal generation circuit 81 includes operational amplifiers A1a and A2a with a drift of 0, an operational amplifier A3a with field effect transistor (FET) input, operational amplifiers A1b and A2b with a drift of 0, an operational amplifier A3b with FET input, switches 82a, 82b, 85, and 86, resistance elements R1a to R3a, and resistance elements R1b to R3b. The operational amplifiers A1a, A2a, A1b, and A2b function as non-inverting amplifiers. Each of the switches 82a, 82b, 85, and 86 is an analog switch and has the same configuration as the switch section 82.

The direct current voltage p2 is input to an input terminal of the operational amplifier A1a, and the direct current voltage p1 is input to an input terminal of the operational amplifier A1b. Output terminals of the operational amplifiers A1a and A1b are connected with input terminals j1 and j3 of the switch 82a. The operational amplifier A2a and the resistance element R1a are connected in series between an output terminal j2 of the switch 82a and an input terminal j1 of the switch 82b. The operational amplifier A2b and the resistance element R1b are connected in series between an output terminal j4 of the switch 82a and an input terminal j3 of the switch 82b.

An output terminal j2 of the switch 82b and the resistance element R2a are connected with input terminals j1 and j3 of the switch 85. An output terminal j2 of the switch 85 is connected with a negative terminal of the operational amplifier A3a, and an output terminal j4 thereof is grounded. The resistance element R3a is connected between an output terminal and the negative terminal of the operational amplifier A3a.

The output terminal j4 of the switch 82b and the resistance element R2b are connected with input terminals j3 and j1 of the switch 86. An output terminal j2 of the switch 86 is connected with a negative terminal of the operational amplifier A3b, and an output terminal j4 thereof is grounded. The resistance element R3b is connected between an output terminal and the negative terminal of the operational amplifier A3b.

The first summing section 11 is a summer obtained by modifying a non-inverting amplifier and includes resistance elements R4 to R6 and an operational amplifier A4 of FET input. One terminal of each of the resistance elements R4, R5, and R6 is connected with a negative terminal of the operational amplifier A4. The other terminal of the resistance element R6 is connected with an output terminal of the operational amplifier A4. A positive terminal of the operational amplifier A4 is grounded.

The signal generation circuit 81 generates the first source signal x1(t) and the second source signal x2(t) based on the direct current voltage p1 and the direct current voltage p2 through switching of the switches 82a, 82b, 85, and 86. The input capacitance of the operational amplifiers A2a and A2b is dependent on input voltage, and accordingly switching noise of the switch 82a behaves non-linearly with respect to the direct current voltage p1 and the direct current voltage p2. Embodiment 8 therefore includes switches in two stages (the switch 82a and the switch 82b) so that noise of the operational amplifiers A2a and A2b is not superimposed on the first source signal x1(t) and the second source signal x2(t).

The output terminal of the operational amplifier A3a is connected with the other terminal of the resistance element R4, and the harmonic electric signal h[1] is input to the other terminal of the resistance element R5. Thus, the first source signal x1(t) generated by the signal generation circuit 81 and the harmonic electric signal h[1] generated by the FG 92 are input into the first summing section 11. As a result, the first summing section 11 sums, and inverts and amplifies the first source signal x1(t) and the harmonic electric signal h[1] to output the first summed signal y1(t).

The second summing section 11B has the same configuration as the configuration of the first summing section 11. However, the output terminal of the operational amplifier A3b is connected with the resistance element R4, and the harmonic electric signal hB[1] is input to the resistance element R5. Accordingly, the second summing section 11B sums, and inverts and amplifies the second source signal x2(t) and the harmonic electric signal hB[1] to output the second summed signal y2(t).

According to Embodiment 8, as described above with reference to FIGS. 26 to 28, influence of non-linearity of the ADC 97 can be reduced by removing some or all of the harmonics from the first measurement signal z1(t) and some or all of the harmonics from the second measurement signal z2(t) in voltage measurement. As a result, a non-linearity error included in the value r of the ratio, that is, a voltage ratio can be reduced. In addition to the above, Embodiment 8 also achieves the same effects as Embodiment 6.

(Embodiment 9)

The following describes a measuring device 1 according to Embodiment 9 of the present invention with reference to FIGS. 19A-19B, 21, 29A-29B, and 30. The measuring devices 1 according to Embodiments 6 to 8 reduce non-linearity of the measurement section 7 and are utilized in simultaneous calibration while performing measurement. In contrast, the measuring device 1 according to Embodiment 9 is not only utilized in simultaneous calibration but also utilized in multipoint calibration.

The measuring device 1 according to Embodiment 9 has a non-linearity error reduction mode and a non-linearity error measurement mode. The measuring device 1 in the non-linearity error reduction mode operates in the same manner as the measuring device 1 according to Embodiment 6 and is utilized in simultaneous calibration. The following describes the non-linearity error measurement mode and utilization in multipoint calibration. The non-linearity error measurement mode of the measuring device 1 includes a first mode and a second mode.

FIG. 29A is a block diagram illustrating the measuring device 1 according to Embodiment 9. The measuring device 1 includes a two-channel signal source 8 in addition to the configuration of the measuring device 1 according to Embodiment 6. The signal source 8 has the same configuration as the configuration of the signal source 8 illustrated in FIG. 19A. However, the signal source 8 according to Embodiment 9 outputs the first signal p1 indicating the first physical quantity p1 to the first signal generation section 3 and the second signal generation section 3B. The signal source 8 also outputs the second signal p2 indicating the second physical quantity p2 to the first signal generation section 3 and the second signal generation section 3B.

The first signal generation section 3, the first removal section 5, the second signal generation section 3B, the second removal section 5B, and the measurement section 7 of the measuring device 1 according to Embodiment 9 respectively have the same configurations as the configurations of the first signal generation section 3, the first removal section 5, the second signal generation section 3B, the second removal section 5B, and the measurement section 7 of the measuring device 1 according to Embodiment 6. An electrical configuration of the measurement section 7 according to Embodiment 9 is the same as the electrical configuration illustrated in FIG. 5A. The detector 19 is a two-channel detector. However, the measurement section 7 has a different configuration from the configuration illustrated in FIG. 5B. The following mainly describes differences of Embodiment 9 from Embodiment 6 (FIGS. 21 to 24) and from Embodiment 5 (FIGS. 19A-19B and 20).

Figure 30:
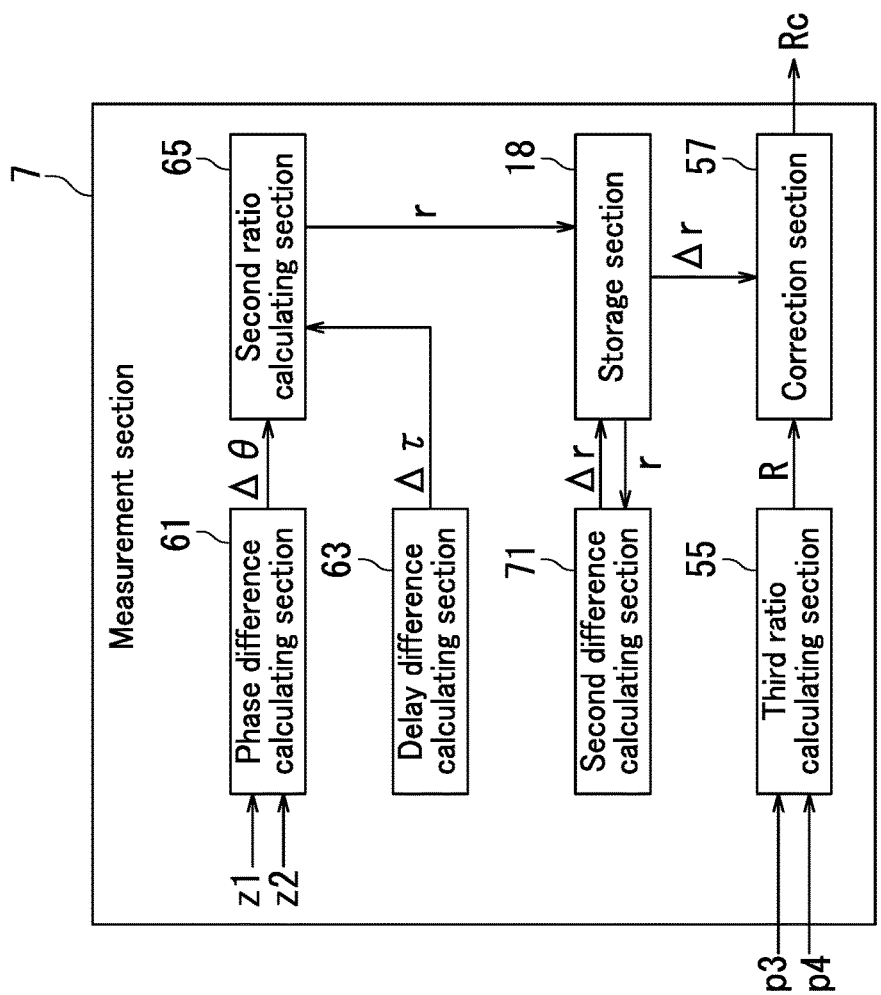
FIG. 30 is a functional block diagram illustrating the measurement section in FIGS. 29A and 29B.

FIG. 30 is a functional block diagram illustrating the measurement section 7. The measurement section 7 includes a second difference calculating section 71 (second difference calculating means), a storage section 18 (storage means), a third ratio calculating section 55 (third ratio calculating means), and a correction section 57 (correction means) in addition to the configuration of the measurement section 7 illustrated in FIG. 23.

The processor 17 functions as the phase difference calculating section 61, the delay difference calculating section 63, the second ratio calculating section 65, the second difference calculating section 71, the third ratio calculating section 55, and the correction section 57 through execution of a computer program stored in the storage section 18.

The following describes operation of the measuring device 1 in the first mode with reference to FIGS. 21, 29A, and 30. Operation of the signal source 8, the first signal generation section 3, and the first removal section 5 is the same as the operation of the signal source 8, the first signal generation section 3, and the first removal section 5 in the first mode according to Embodiment 5.

The second signal generation section 3B outputs the second source signal x2(t) in which the first physical quantity p1 is maintained constant and the second physical quantity p2 is changed in a stepwise manner. The second summing section 11B of the second removal section 5B sums the harmonic signal hB[n] and the second source signal x2(t) to output the second summed signal y2(t). Having the harmonic signal hB[n] added thereto, the second summed signal y2(t) is a signal from which a corresponding harmonic has been removed. The measurement section 7 inputs the second summed signal y2(t) and outputs the second measurement signal z2(t) from which the harmonic has been removed. In Embodiment 9, the second measurement signal z2(t) from which the harmonic has been removed is referred to as a second measurement signal z2a(t). It should be noted that as in Embodiment 5, the first measurement signal z1(t) from which the harmonic has been removed is referred to as the first measurement signal z1a(t).

Based on the first measurement signal z1a(t) and the second measurement signal z2a(t), the second ratio calculating section 65 calculates the value r of the ratio of the second physical quantity p2 to the first physical quantity p1 for each second physical quantity p2. That is, the phase difference calculating section 61 calculates a phase difference $\Delta\theta$ between the fundamental in the first measurement signal z1a(t) and the fundamental in the second measurement signal z2a(t) for each second physical quantity p2. The delay difference calculating section 63 calculates a delay time difference $\Delta\tau$ between the first measurement signal z1a(t) and the second measurement signal z2a(t). The second ratio calculating section 65 calculates the value r of the ratio in accordance with the equation (2) using the phase difference $\Delta\theta$ and the delay time difference $\Delta\tau$ based on the first measurement signal z1a(t) and the second measurement signal z2a(t) for each second physical quantity p2, and stores the value r of the ratio in the storage section 18. The value r of the ratio includes a reduced non-linearity error, and therefore the accuracy thereof is high. Through the above, the first mode has been described.

The following describes operation of the measuring device 1 in the second mode. Operation of the signal source 8, the first signal generation section 3, and the second signal generation section 3B is the same as the operation of the signal source 8, the first signal generation section 3, and the second signal generation section 3B in the first mode. Operation of the first removal section 5 is the same as the operation of the first removal section 5 in the second mode according to Embodiment 5.

The harmonic generation section 9B [n] of the second removal section 5B does not generate the harmonic signal hB [n]. Accordingly, the second summing section 11B outputs the second source signal x2(t) as the second summed signal y2(t) without summing the harmonic signal hB[n] and the second source signal x2(t). Having no harmonic signal hB [n] added thereto, the second summed signal y2(t) is a signal from which none of the harmonics has been removed. The measurement section 7 inputs the second summed signal y2(t) and outputs the second measurement signal z2(t) from which none of the harmonics has been removed. In Embodiment 9, the second measurement signal z2(t) from which none of the harmonics has been removed is referred to as a second measurement signal z2b(t). It should be noted that as in Embodiment 5, the first measurement signal z1(t)

from which none of the harmonics has been removed is referred to as a first measurement signal z1b(t).

Based on the first measurement signal z1b(t) and the second measurement signal z2b(t), the second ratio calculating section 65 calculates the value r of the ratio of the second physical quantity p2 to the first physical quantity p1 for each second physical quantity p2. That is, the phase difference calculating section 61 calculates a phase difference $\Delta\theta$ between the fundamental in the first measurement signal z1b(t) and the fundamental in the second measurement signal z2b(t) for each second physical quantity p2. The delay difference calculating section 63 calculates a delay time difference $\Delta\tau$ between the first measurement signal z1b(t) and the second measurement signal z2b(t). The second ratio calculating section 65 calculates the value r of the ratio in accordance with the equation (2) using the phase difference $\Delta\theta$ and the delay time difference $\Delta\tau$ based on the first measurement signal z1b(t) and the second measurement signal z2b(t) for each second physical quantity p2, and stores the value r of the ratio in the storage section 18. The value r of the ratio includes a non-linearity error that is not reduced. Through the above, the second mode has been described.

The second difference calculating section 71 acquires from the storage section 18 the value r of the ratio calculated in the first mode and the value r of the ratio calculated in the second mode for each second physical quantity p2. Subsequently, the second difference calculating section 71 calculates a difference $\Delta r$ between the value r of the ratio calculated in the first mode and the value r of the ratio calculated in the second mode for each second physical quantity p2. The storage section 18 stores therein the difference $\Delta r$ in association with the value r of the ratio calculated in the second mode for each second physical quantity p2.

As a result, a table associating the value r of the ratio calculated in the second mode with the difference $\Delta r$ (hereinafter, referred to as an "error table") is created. The difference $\Delta r$ represents the non-linearity error, and therefore the error table is a table associating the value r of the ratio calculated in the second mode with the non-linearity error. Preferably, the second physical quantity p2 is changed finely in a sufficiently large number of steps so that data in the error table is sufficiently continuous and sufficiently precise.

Since the error table is prepared, an analog signal p3 indicating a third physical quantity p3 and an analog signal p4 indicating a fourth physical quantity p4 can be input into the measurement section 7 as in Embodiment 5. Therefore, as in Embodiment 5, the third ratio calculating section 55 calculates a value R (=p4/p3) of a ratio of the fourth physical quantity p4 to the third physical quantity p3. The correction section 57 corrects the value R of the ratio calculated by the third ratio calculating section 55 based on the error table, that is, based on the difference $\Delta r$ stored in the storage section 18 to calculate a value Rc of the ratio including a reduced non-linearity error. In a case where a drift in the non-linearity error is negligible, the error table may be prepared at any timing as in Embodiment 5.

The following describes a measuring device 1 according to a variation of Embodiment 9 with reference to FIG. 29B. FIG. 29B is a block diagram illustrating the measuring device 1 according to the variation. The measuring device 1 includes a first signal source 8 and a second signal source 8B instead of the signal source 8 of the measuring device 1 illustrated in FIG. 29A. The first signal source 8 is included in the first signal generation section 3, and the second signal source 8B is included in the second signal generation section 3B. According to the variation, in each of the first and second modes, the first signal source 8 generates and outputs the first source signal x1(t) in which the first physical quantity p1 is maintained constant and the second physical quantity p2 is changed in a stepwise manner, and the second signal source 8B generates and outputs the second source signal x2(t) in which the first physical quantity p1 is maintained constant and the second physical quantity p2 is changed in a stepwise manner.

According to Embodiment 9 (hereinafter, including the variation thereof), as described above with reference to FIGS. 29A-29B and 30, it is possible to easily determine the value r of the ratio including a non-linearity error reduced through harmonic removal and the value r of the ratio including a non-linearity error that is not reduced. Therefore, the error table for achieving utilization in multipoint calibration can be easily prepared. In addition to the above, Embodiment 9 also achieves the same effects as Embodiment 5.

The measuring device 1 according to Embodiment 8 described with reference to FIGS. 26 and 28 may have the non-linearity error reduction mode and the non-linearity error measurement mode. As described with reference to FIGS. 26 and 28, the measuring device 1 in the non-linearity error reduction mode is utilized in simultaneous calibration. The measuring device 1 in the non-linearity error measurement mode operates in the same manner as the measuring device 1 according to Embodiment 9 and is utilized in multipoint calibration.

(Embodiment 10)

Figure 31:
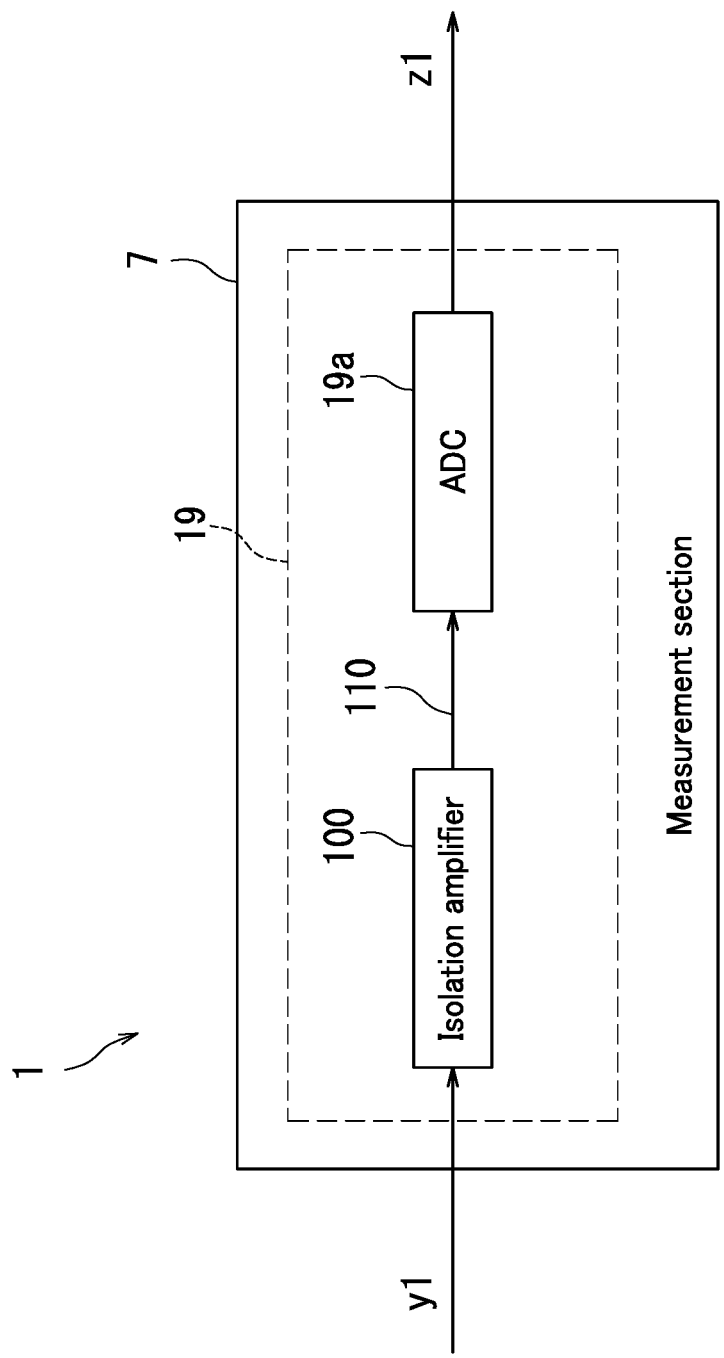
FIG. 31 is a block diagram illustrating a measurement section of a measuring device according to Embodiment 10 of the present invention.

The following describes a measuring device 1 according to Embodiment 10 of the present invention with reference to FIGS. 13 and 31. As illustrated in FIG. 13, the measuring device 1 according to Embodiment 10 has the same configuration as the configuration of the measuring device 1 according to Embodiment 2. However, the measuring device 1 according to Embodiment 10 includes a measurement section 7 illustrated in FIG. 31 instead of the measurement section 7 of the measuring device 1 according to Embodiment 2. The measuring device 1 according to Embodiment 10 is utilized in simultaneous calibration.

FIG. 31 is a block diagram illustrating the measurement section 7 of the measuring device 1 according to Embodiment 10. As illustrated in FIG. 31, a detector 19 of the measurement section 7 includes an isolation amplifier 100 and an ADC 19a. The isolation amplifier 100 is an amplifier in which an input section and an output section of the isolation amplifier 100 are isolated from each other. The isolation amplifier 100 amplifies the first summed signal y1(t) and outputs the first summed signal y1(t) to the ADC 19a as an amplified signal 110. The ADC 19a converts the amplified signal 110, which is an analog signal, to a digital signal and outputs the digital signal as the first measurement signal z1(t). Other than the above, operation of the measuring device 1 is the same as that of Embodiment 2, and therefore description thereof is omitted.

The measuring device 1 according to Embodiment 10 can for example be applied to an isolation input type digital voltmeter in which an isolation amplifier is located upstream of an AD converter. Generally, non-linearity of the isolation amplifier is higher than non-linearity of the AD converter. It is therefore difficult to perform measurement with high linearity using a general insulation input type digital voltmeter. However, the use of the measuring device 1 according to Embodiment 10 can for example allow an insulation input type digital voltmeter having a linearity of 10 ppm to be achieved. In addition to the above, the measuring device 1 according to Embodiment 10 also achieves the same effects as the measuring device 1 according to Embodiment 2.

(Embodiment 11)

Figure 32:
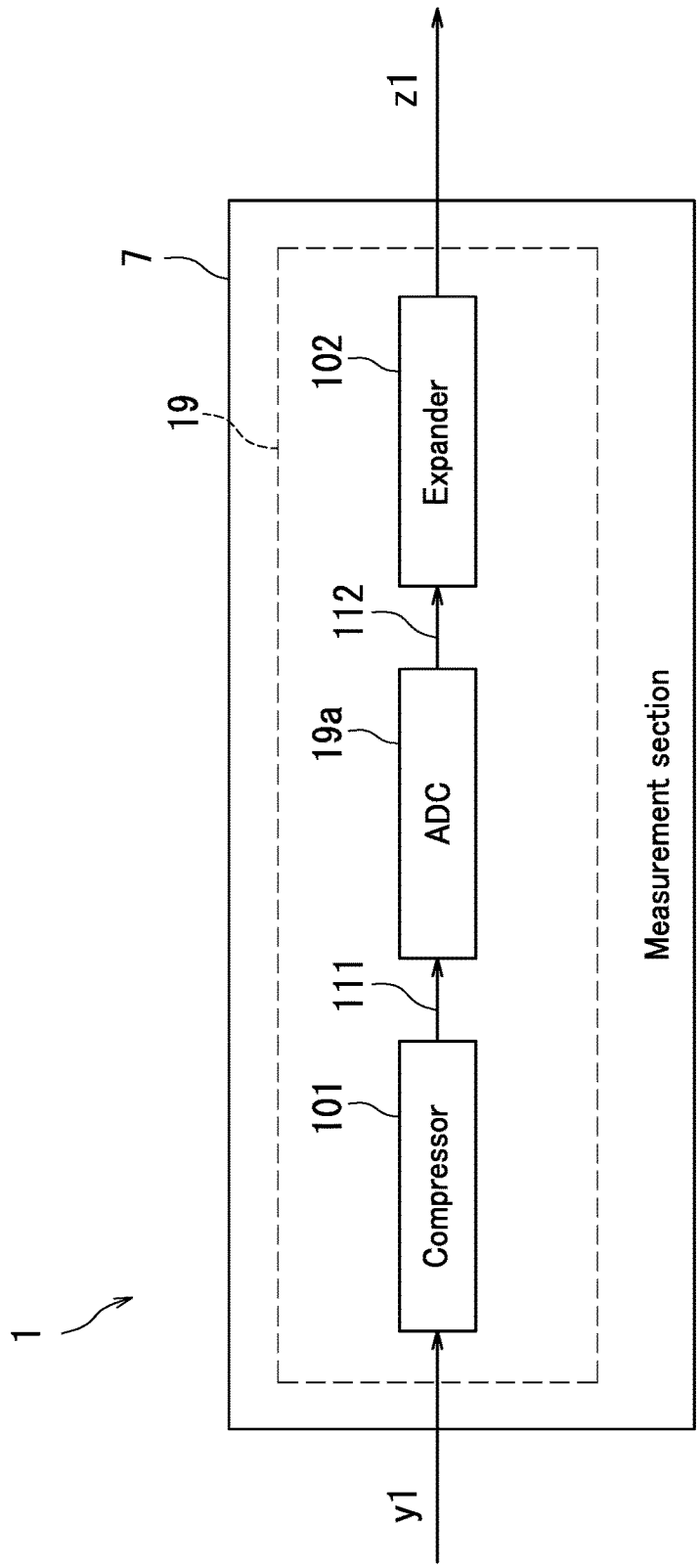
FIG. 32 is a block diagram illustrating a measurement section of a measuring device according to Embodiment 11 of the present invention.

The following describes a measuring device 1 according to Embodiment 11 of the present invention with reference to FIGS. 13 and 32. As illustrated in FIG. 13, the measuring device 1 according to Embodiment 11 has the same configuration as the configuration of the measuring device 1 according to Embodiment 2. However, the measuring device 1 according to Embodiment 11 includes a measurement section 7 illustrated in FIG. 32 instead of the measurement section 7 of the measuring device 1 according to Embodiment 2. The measuring device 1 according to Embodiment 11 is utilized in simultaneous calibration.

FIG. 32 is a block diagram illustrating the measurement section 7 of the measuring device 1 according to Embodiment 11. As illustrated in FIG. 32, a detector 19 of the measurement section 7 includes a compressor 101, an ADC 19a, and an expander 102. The compressor 101 compresses the amplitude of the first summed signal y1(t) and outputs the first summed signal y1(t) as an amplitude-compressed signal 111 to the ADC 19a. The compressor 101 is for example an amplitude compression circuit such as a logarithmic amplifier. The ADC 19a converts the amplitude-compressed signal 111, which is an analog signal, to a digital signal and outputs the digital signal to the expander 102 as an amplitude-compressed signal 112. The expander 102 expands the amplitude of the amplitude-compressed signal 112 and outputs the amplitude-compressed signal 112 as the first measurement signal z1(t). The expander 102 is for example a digital expansion operation device. Other than the above, operation of the measuring device 1 is the same as that of Embodiment 2, and therefore description thereof is omitted.

The measuring device 1 according to Embodiment 11 can for example be applied to a compressed amplitude input type digital voltmeter. In the compressed amplitude input type digital voltmeter, an amplitude compression circuit is located upstream of an AD converter, and a digital expansion operation device is located downstream of the AD converter. Generally, a compression function of the amplitude compression circuit drifts depending on temperature and elapsed time, and therefore it is difficult to accurately expand an amplitude-compressed signal with the amplitude compression circuit. Therefore, a digital signal expanded by the digital expansion operation device typically exhibits higher non-linearity than a digital signal output by the AD converter. The compressed amplitude input type digital voltmeter is therefore rarely used in general quantitative voltage measurement. That is, the compressed amplitude input type digital voltmeter has limited applicability and is for example used in ultrasonic diagnostic equipment for dynamic range expansion.

However, the use of the measuring device 1 according to Embodiment 11 can for example allow a compressed amplitude input type digital voltmeter having a linearity of 100 ppm to be achieved. As a result, the use of the measuring device 1 enables voltage measurement with a wide dynamic range in a wider range of applications than that requiring quantification. In addition to the above, the measuring device 1 according to Embodiment 11 also achieves the same effects as the measuring device 1 according to Embodiment 2.

The following describes the present invention in detail using an example. However, the present invention is not limited to the following example.

EXAMPLE

In the present example, the measuring device 1 according to Embodiment 8 described with reference to FIGS. 26 and 28 was used to experiment with utilization in simultaneous calibration. The frequency f of the fundamentals in the first source signal x1(t) and the second source signal x2(t) was set to 307.2 Hz. The ADC 97 was a 24 bit delta-sigma (ΔΣ type) analog-digital converter (PEX-320724, product of Interface Corporation). A reduction of a non-linearity error in the ADC 97 was confirmed in the present example.

First, conditions in the present example will be described. The FG 91 (WF1947, product of NF CORPORATION) generated a square wave at 12.288 MHz as the base clock clk0. The base clock clk0 was input into the FPGA 94 (DE0, product of Terasic Inc.). The FPGA 94 generated the clocks clk1 and clk2 at 153.6 Hz(=f/2) by dividing the base clock clk0 by 80,000. The FPGA 94 also generated the clock clk3 at 307.2 Hz (=f) by dividing the base clock clk0 by 40,000. The clock clk1 was used for driving the switch 82a. The clock clk2 was used for driving the switch 82b. The clock clk3 was used for driving the switch 85 and the switch 86.

The FPGA 94 generated the sampling clock clk4 at 614.4 kHz by dividing the base clock clk0 by 20. The sampling clock clk4 was common among both the channels of the ADC 97. The non-linearity error and signal bandwidth of the ADC 97 were 24 ppm and 614.4 kHz, respectively, which are typical values.

The SG 93 included three nickel-metal-hydride rechargeable batteries (Eneloop 1.3 V, product of SANYO Electric Co., Ltd.) and a six resistor divider. The SG 93 maintained the direct current voltage p1 at approximately 3.9 V. The SG 93 changed the direct current voltage p2 in a range of from 0 V to 3.6 V in six steps at equal intervals. The reference voltage pr was 0 V. The direct current voltage p1 and the direct current voltage p2 generated by the SG 93 were measured using a ratiometer provided in the DVM 95 (6581, product of ADC CORPORATION). The DVM 95 had an accuracy of 1 microvolt, which was equal to an error of approximately 0.3 ppm in ratio measurement.

The SB 96 generated the first source signal x1(t) and the second source signal x2(t) through the switches 82a, 82b, 85, and 86 (MAX4527, product of Maxim). The harmonic electric signal h[1] and the harmonic electric signal hB[1] at 614.4 Hz (=20 were input into the SB 96 from the FG 92 (WF1948, product of NF CORPORATION). Each of the harmonic electric signal h[1] and the harmonic electric signal hB[1] was a sine wave. Through the first summing section 11, the SB 96 summed the first source signal x1(t) and the harmonic electric signal h[1] to generate the first summed signal y1(t). Through the second summing section 11B, the SB 96 summed the second source signal x2(t) and the harmonic electric signal hB [1] to generate the second summed signal y2(t). The resistance elements R1a, R1b, R2a, R2b, and R6 each had a resistance value of 100 kΩ The resistance element R3a and R3b each had a resistance value of 10 kΩ.

The ADC 97 measured the first summed signal y1(t) and the second summed signal y2(t). The ADC 97 accumulated digital data for 2.5 seconds and determined mean data for random noise reduction. Prior to the measurement, two input terminals of the ADC 97 were grounded, a reference signal including offset of an operational amplifier and switching noise was obtained, and the offset of the operational amplifier and the switching noise were removed by subtraction.

The following describes calculation of a voltage ratio rt by time averaging with reference to FIGS. 33A-33E. FIG.

33A is a waveform diagram illustrating the first measurement signal z1(t) from which none of the harmonics has been removed. FIG. 33B is a waveform diagram illustrating the second measurement signal z2(t) from which none of the harmonics has been removed. In order to remove switching noise and a transition time effect, an average voltage value was calculated in each of regions V11 to V28 represented by shaded areas. The average voltage values in the respective regions V11 to V28 are indicated by the same reference signs as those of the regions. For example, the average voltage value in the region V11 is indicated by the reference sign V11. The voltage ratio rt was calculated in accordance with an equation (3).

[Formula 6]

$$rt = \frac{1}{4}\left(\frac{V13-V14}{V12-V11} + \frac{V17-V18}{V16-V15} + \frac{V23-V24}{V22-V21} + \frac{V27-V28}{V26-V25}\right) \quad (3)$$

The voltage ratio rt was recorded in the PC 98 and compared with a measurement value determined by the DVM 95. Thus, the non-linearity error in the ADC 97 was calculated.

Figure 34A:
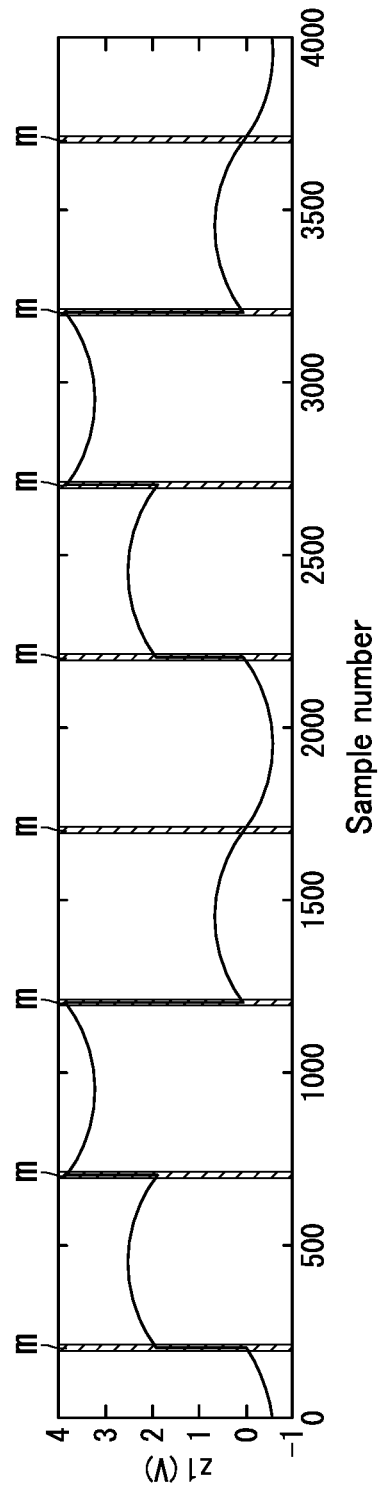
FIG. 34A is a waveform diagram illustrating a first measurement signal from which a harmonic has been removed in an example of the present invention.
Figure 34B:
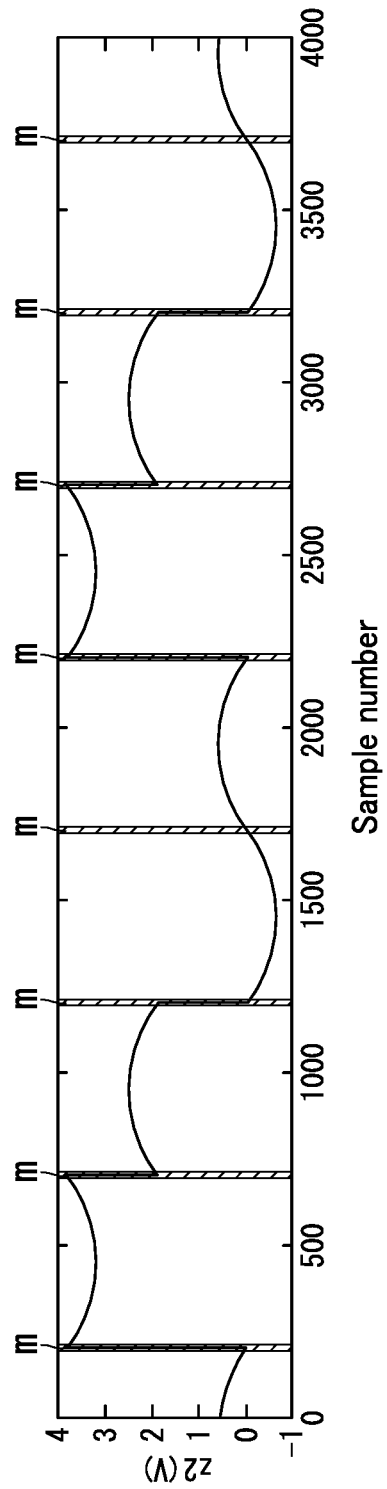
FIG. 34B is a waveform diagram illustrating a second measurement signal from which a harmonic has been removed in the example of the present invention.

The following describes calculation of the voltage ratio r based on the phase with reference to FIGS. 34A-34B. FIG. 34A is a waveform diagram illustrating the first measurement signal z1(t) from which the second-order harmonic has been removed. FIG. 34B is a waveform diagram illustrating the second measurement signal z2(t) from which the second-order harmonic has been removed. The PC 98 performed zero replacement in each of regions m represented by shaded areas to remove remaining switching noise. Subsequently, the PC 98 calculated the fundamental (frequency f) and the second-order harmonic (frequency 2f) in each of the first measurement signal z1(t) and the second measurement signal z2(t) through Fourier transform of each of the first measurement signal z1(t) and the second measurement signal z2(t).

The PC 98 calculated and displayed on a display the phase and the amplitude of the second-order harmonic in each of the first measurement signal z1(t) and the second measurement signal z2(t). In the present example, an operator manually controlled the FG 92 while monitoring the phase and the amplitude of the second-order harmonic and thus adjusted the amplitude and the phase of the harmonic electric signal h[1] and the harmonic electric signal hB[1] such that the amplitude of the second-order harmonic was less than 0.1. The PC 98 then calculated the voltage ratio r in accordance with the equation (2). The voltage ratio r was recorded in the PC 98 and compared with a measurement value determined by the DVM 95. Thus, the non-linearity error in the ADC 97 was calculated. An effect of the harmonic removal was evaluated through comparison between the non-linearity error in the voltage ratio r and the non-linearity error in the voltage ratio rt.

Figure 35:
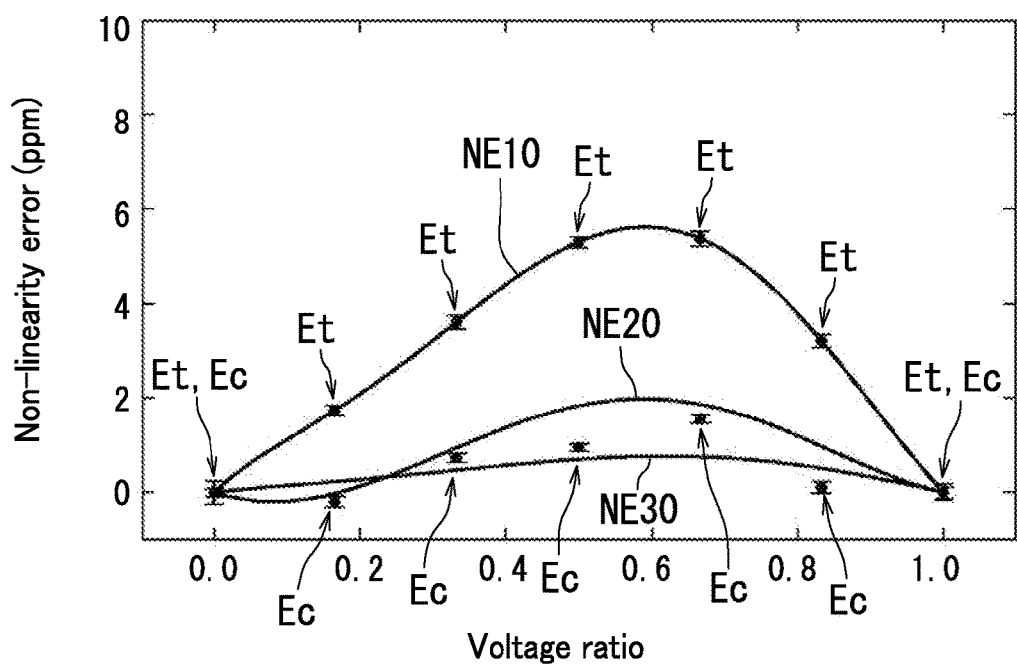
FIG. 35 is a diagram illustrating a non-linearity error in the example of the present invention.

The following describes the effect of the harmonic removal with reference to FIG. 35. FIG. 35 is a diagram illustrating the non-linearity error. The horizontal axis represents voltage ratio based on the measurement values determined by the DVM 95, and the vertical axis represents non-linearity error. Points Et represent the non-linearity error in the voltage ratio rt, and points Ec represent the non-linearity error in the voltage ratio r. Through comparison between points Et and points Ec, it was confirmed that the removal of the second-order harmonic reduced the non-linearity error by approximately 70%. The non-linearity error in the voltage ratio r was reduced to as low as approximately 2 ppm or less.

A curve NE 10 represents a result obtained by approximating the non-linearity of the ADC 97 before the harmonic removal with a sixth-order polynomial function G(r). The curve NE10 agrees with the experimental result of the voltage ratio rt. A curve NE20 was obtained by approximating the non-linearity of the ADC 97 with the curve NE10. The curve NE20 represents a result of simulation for the non-linearity error in the case where the second-order harmonic is removed. The curve NE20 agrees with the experimental result of the voltage ratio r. A curve NE30 represents a result of simulation for the non-linearity error when the second-order harmonic, the third-order harmonic, and the fifth-order harmonic are removed. The curve NE30 was obtained by approximating the non-linearity of the ADC 97 with the curve NE10. The non-linearity error was reduced to less than 1 ppm.

The following describes switching operation in the signal generation circuit 81 with reference to FIGS. 28 and 33A-33E.

The switch 82a will be described. When the clock clk1 is at a high level, a signal input to the terminal j1 is output from the terminal j2, and a signal input to the terminal j3 is output from the terminal j4. When the clock clk1 is at a low level, a signal input to the terminal j1 is output from the terminal j4, and a signal input to the terminal j3 is output from the terminal j2.

In the case of the switch 82b, the clock clk1 is replaced with the clock clk2 in the description of the switch 82a. In the case of each of the switches 85 and 86, the clock clk1 is replaced with the clock clk3 in the description of the switch 82a.

FIG. 33A illustrates the first measurement signal z1(t) from which none of the harmonics has been removed. Accordingly, this first measurement signal z1(t) has the same waveform as the waveform of the first source signal x1(t). The following description therefore deems the waveform of the first measurement signal z1(t) as the waveform of the first source signal x1(t). Likewise, the following description deems the waveform of the second measurement signal z2(t) in FIG. 33B as the waveform of the second source signal x2(t).

FIG. 33C is a waveform diagram illustrating the clk1 that is supplied to the switch 82a. FIG. 33D is a waveform diagram illustrating the clock clk2 that is supplied to the switch 82b. FIG. 33E is a waveform diagram illustrating the clock clk3 that is supplied to the switches 85 and 86.

During an interval from time t0 to time t1, the clock clk1 is at a high level, the clock clk2 is at a low level, and the clock clk3 is at a low level. Accordingly, the first source signal x1(t) has a level of the direct current voltage p1, and the second source signal x2(t) has a level of the direct current voltage p2.

During an interval from time t1 to time t2, the clock clk1 is at the high level, the clock clk2 is at the low level, and the clock clk3 is at a high level. Accordingly, the first source signal x1(t) and the second source signal x2(t) have the level of the reference voltage pr.

During an interval from time t2 to time t3, the clock clk1 is at a low level, the clock clk2 is at the low level, and the clock clk3 is at the high level. Accordingly, the first source signal x1(t) and the second source signal x2(t) have the level of the reference voltage pr.

During an interval from time t3 to time t4, the clock clk1 is at the low level, the clock clk2 is at the low level, and the clock clk3 is at the low level. Accordingly, the first source signal x1(t) has the level of the direct current voltage p2, and the second source signal x2(t) has the level of the direct current voltage p1.

As described above, the signal generation circuit 81 generates the staircase first source signal x1(t) and the staircase second source signal x2(t) through the switching operation.

Through the above, embodiments of the present invention have been described with reference to the drawings. However, the present invention is not limited to the above-described embodiments and can be practiced in various ways within the scope without departing from the essence of the present invention (for example, as described below in sections (1)-(8)). The drawings schematically illustrate elements of configuration in order to facilitate understanding and properties of elements of configuration illustrated in the drawings, such as thickness, length, and number thereof, may differ from actual properties thereof in order to facilitate preparation of the drawings. Furthermore, properties of elements of configuration described in the above embodiments, such as shapes and dimensions, are merely examples and are not intended as specific limitations. Various alterations may be made so long as there is no substantial deviation from the effects of the present invention.

(1) In Embodiments 1 to 11 (FIGS. 1 to 32), which order of harmonic is to be removed can be determined as appropriate, and the number N of harmonics to be removed can be determined as appropriate. Removing only a low-order harmonic can reduce the non-linearity error. However, further removing higher-order harmonics can further reduce the non-linearity error.

(2) In Embodiments 1 to 11 (FIGS. 1 to 32), each measuring device 1 may be produced as one product, or the measuring device 1 excluding the measurement section 7 may be produced as one product. In the latter case, an existing or commercially available measuring device is used as the measurement section 7.

(3) In Embodiments 2, 10, and 11 (FIGS. 13, 31, and 32), the first summer 11a is provided in one stage. Alternatively, a plurality of stages of summers may be provided to sum the first source signal x1(t) and the harmonic electric signal ha[n]. For example, a first-stage summer sums the harmonic electric signals ha[1] to ha[N] to generate a summed signal including the harmonic electric signals ha[1] to ha[N], and a second-stage summer sums the thus generated summed signal and the first source signal x1(t) to generate the first summed signal y1(t).

(4) In Embodiments 2, 10, and 11 (FIGS. 13, 31, and 32), the oscillator 9a[n] generates the harmonic electric signal ha[n] of a sine wave. Alternatively, the oscillator 9a[n] may generate the harmonic electric signal ha[n] of any other waveform. For example, the oscillator 9a[n] may generate the harmonic electric signal ha[n] of a square wave or the harmonic electric signal ha[n] of a triangle wave. In Embodiment 3 (FIG. 14), the harmonic generation section 9b[n] generates the harmonic optical signal hb[n] of a square wave. Alternatively, the harmonic generation section 9b[n] may generate the harmonic optical signal hb[n] of any other waveform. For example, the harmonic generation section 9b[n] may generate the harmonic optical signal hb[n] of a triangle wave.

(5) The measuring device 1 according to Embodiment 3 (FIG. 14) may be applied to a spectrometry instrument with an array detector, which is referred to as a multi-channel spectrograph or polychromator. In the case of quantitative determination (chemometrics) performed based on spectroscopic measurement result, it is an important factor that measurement data is highly precise. The present invention can therefore be applied to spectroscopic measurement in such a case.

(6) In Embodiments 4 and 7 (FIGS. 18 and 25), a low-pass filter may be provided instead of the first bandpass filter 4 or in addition to the first bandpass filter 4. In Embodiment 7, a low-pass filter may be provided instead of the second bandpass filter 4B or in addition to the second bandpass filter 4B. The low-pass filter is an analog filter for attenuating a harmonic. The low-pass filter may be additionally used in order to remove high-order harmonics (for example, frequency-decoupled or higher harmonics) in Embodiments 1 to 11. For example, the low-pass filter is located upstream or downstream of the first summing section 11, upstream or downstream of the first summer 11a, upstream or downstream of the first summer 11b, or upstream or downstream of the second summing section 11B.

(7) In a case where the measuring device 1 according to Embodiment 4, 5, 6, 7, or 9 (FIG. 18, 19A-19B, 21, 25, or 29A-29B) is applied to voltage measurement, the configuration of the measurement section 7 may be the same as the configuration of the measurement section 7 according to Embodiment 10 (FIG. 31) or the configuration of the measurement section 7 according to Embodiment 11 (FIG. 32). In Embodiment 8 (FIG. 26), the isolation amplifier 100 illustrated in FIG. 31 may be disposed upstream of the ADC 97. Alternatively, in Embodiment 8, the compressor 101 illustrated in FIG. 32 may be disposed upstream of the ADC 97, and the expander 102 illustrated in FIG. 32 may be disposed downstream of the ADC 97.

(8) In Embodiments 1 to 11 and the example, the measuring device 1 is applied to voltage measurement or optical measurement. However, scope of application of the present invention is not limited thereto. For example, the measuring device 1 according to Embodiment 1, 4, 5, 6, 7, or 9 (FIG. 1, 18, 19A-19B, 21, 25, or 29A-29B) may be applied to current measurement, acoustic measurement, or vibration measurement.

In the case where the measuring device 1 is applied to current measurement, for example, each of the first physical quantity p1 to the fourth physical quantity p4 and the reference physical quantity pr is an electric current, and each of the first source signal x1(t), the second source signal x2(t), the harmonic signal h[n], the harmonic signal hB[n], the first summed signal y1(t), the second summed signal y2(t), the first measurement signal z1(t), and the second measurement signal z2(t) is an electric signal.

In the case where the measuring device 1 is applied to acoustic measurement, for example, each of the first physical quantity p1 to the fourth physical quantity p4 and the reference physical quantity pr is an acoustic pressure, and each of the first source signal x1(t), the second source signal x2(t), the harmonic signal h[n], the harmonic signal hB[n], the first summed signal y1(t), and the second summed signal y2(t) is an acoustic wave. Each of the first measurement signal z1(t) and the second measurement signal z2(t) is an electric signal.

In the case where the measuring device 1 is applied to vibration measurement, for example, each of the first physical quantity p1 to the fourth physical quantity p4 and the reference physical quantity pr is an elastic wave displacement, and each of the first source signal x1(t), the second source signal x2(t), the harmonic signal h[n], the harmonic signal hB[n], the first summed signal y1(t), and the second summed signal y2(t) is an elastic wave. Each of the first measurement signal z1(t) and the second measurement signal z2(t) is an electric signal.

INDUSTRIAL APPLICABILITY

The present invention is applicable to the field of measuring devices for measuring physical quantities.

REFERENCE SIGNS LIST

1 Measuring device
3 First signal generation section
3B Second signal generation section
5 First removal section
5B Second removal section
7 Measurement section
9[n] Harmonic generation section
9B [n] Harmonic generation section
11 First summing section
11B Second summing section
13 First Fourier transform section
13B Second Fourier transform section
15 First control section
15B Second control section
18 Storage section
19 Detector
21 Phase calculating section
23 Delay calculating section
25 First ratio calculating section
53 First difference calculating section
55 Third ratio calculating section
57 Correction section
61 Phase difference calculating section
63 Delay difference calculating section
65 Second ratio calculating section
71 Second difference calculating section

The invention claimed is:

1. A measuring device comprising:
a first signal generator configured to generate a first source signal including a fundamental and a plurality of harmonics based on a first physical quantity and a second physical quantity; and
a first removal section configured to remove some or all of the plurality of harmonics from the first source signal to reduce influence of non-linearity of a detector of a measuring instrument, wherein
the first removal section includes:
a first summer configured to sum the first source signal and a harmonic signal having the same frequency as a removal target harmonic among the plurality of harmonics to output a first summed signal;
a harmonic generator configured to generate the harmonic signal;
a first Fourier transformer configured to input therein a first measurement signal in digital form output from the detector and calculate a plurality of harmonics included in the first measurement signal, the first measurement signal in digital form being output by the detector based on the first summed signal in analog form detected by the detector; and
a first controller configured to cause the harmonic generator to adjust either or both of an amplitude and a phase of the harmonic signal so that a harmonic that matches the removal target harmonic is removed from the first measurement signal, the measuring device is applied to voltage measurement, optical measurement, current measurement, acoustic measurement, or vibration measurement, when the measuring device is applied to the voltage measurement, each of the first physical quantity and the second physical quantity is a voltage, and each of the first source signal, the harmonic signal, the first summed signal, and the first measurement signal is an electric signal, when the measuring device is applied to the optical measurement, each of the first physical quantity and the second physical quantity is an optical intensity, each of the first source signal, the harmonic signal, and the first summed signal is an optical signal, and the first measurement signal is an electric signal, when the measuring device is applied to the current measurement, each of the first physical quantity and the second physical quantity is an electric current, and each of the first source signal, the harmonic signal, the first summed signal, and the first measurement signal is an electric signal, when the measuring device is applied to the acoustic measurement, each of the first physical quantity and the second physical quantity is an acoustic pressure, each of the first source signal, the harmonic signal, and the first summed signal is an acoustic wave, and the first measurement signal is an electric signal, and when the measuring device is applied to the vibration measurement, each of the first physical quantity and the second physical quantity is an elastic wave displacement, each of the first source signal, the harmonic signal, and the first summed signal is an elastic wave, and the first measurement signal is an electric signal.

2. The measuring device according to claim 1, wherein the first source signal is a periodic signal, and
one period of the first source signal includes:
a first signal having a first duration and indicating the first physical quantity;
a second signal having a second duration and indicating the second physical quantity; and
a reference signal having a third duration and indicating a reference physical quantity.

3. The measuring device according to claim 1, further comprising the measuring instrument including the detector, wherein each of the first physical quantity and the second physical quantity is a voltage, each of the first source signal and the harmonic signal is an electric signal, and
the detector includes an analog-digital converter configured to convert the first summed signal being an analog signal to a digital signal and output the digital signal as the first measurement signal.

4. The measuring device according to claim 1, further comprising
the measuring instrument including the detector, wherein
each of the first physical quantity and the second physical quantity is an optical intensity,
each of the first source signal and the harmonic signal is an optical signal, and
the detector includes:
a photoelectric converter configured to convert the first summed signal being an optical signal to an electric signal; and
an analog-digital converter configured to convert the electric signal being an analog signal to a digital signal and output the digital signal as the first measurement signal.

5. The measuring device according to claim 1, further comprising
the measuring instrument, wherein
the instrument includes:
the detector;
a phase calculating section configured to calculate a phase of a fundamental in the first measurement signal; and
a first ratio calculating section configured to calculate a value of a ratio of the second physical quantity to the first physical quantity based on the phase of the fundamental in the first measurement signal.

6. The measuring device according to claim 5, wherein
the measuring instrument further includes a delay calculating section configured to calculate a delay time of the first measurement signal relative to the first summed signal, and
the first ratio calculating section calculates the value of the ratio in accordance with an equation (1), $$r = \frac{p2 - pr}{p1 - pr} = \tan\left(\frac{\pi}{4} + \theta + 2\pi f \tau\right) \quad (1)$$

where r represents the value of the ratio,
p1 represents the first physical quantity,
p2 represents the second physical quantity,
pr represents a reference physical quantity,
$\theta$ represents the phase of the fundamental in the first measurement signal,
f represents a frequency of the fundamental in the first measurement signal, and
$\tau$ represents the delay time.

7. The measuring device according to claim 5, having
a non-linearity error measurement mode including a first mode and a second mode,
in each of the first mode and the second mode, the first signal generator outputs the first source signal in which the first physical quantity is maintained constant and the second physical quantity is changed in a stepwise manner,
in the first mode, the first summer sums the harmonic signal and the first source signal to output the first summed signal, and the detector outputs the first measurement signal from which the harmonic has been removed,
in the first mode, the first ratio calculating section calculates the value of the ratio for each second physical quantity based on the first measurement signal from which the harmonic has been removed,
in the second mode, the first summer outputs the first source signal as the first summed signal without summing the harmonic signal and the first source signal, and the detector outputs the first measurement signal from which none of the harmonics has been removed,
in the second mode, the first ratio calculating section calculates the value of the ratio for each second physical quantity based on the first measurement signal from which none of the harmonics has been removed, and
the measuring instrument further includes:
a first difference calculating section configured to calculate a difference between the value of the ratio calculated in the first mode and the value of the ratio calculated in the second mode for each second physical quantity; and a storage configured to store therein the difference in association with the value of the ratio calculated in the second mode for each second physical quantity.

8. The measuring device according to claim 7, wherein
the measuring instrument further includes:
a third ratio calculating section configured to calculate a value of a ratio of a fourth physical quantity to a third physical quantity; and
a correction section configured to correct the value of the ratio calculated by the third ratio calculating section based on the difference stored in the storage.

9. The measuring device according to claim 1, further comprising:
a second signal generator configured to generate a second source signal including a fundamental and a plurality of harmonics and having a waveform of the first source signal with the first physical quantity and the second physical quantity interchanged; and
a second removal section configured to remove some or all of the plurality of harmonics from the second source signal.

10. The measuring device according to claim 1, further comprising:
a second signal generator configured to generate a second source signal including a fundamental and a plurality of harmonics and having a waveform of the first source signal with the first physical quantity and the second physical quantity interchanged; and
a second removal section configured to remove some or all of the plurality of harmonics from the second source signal, wherein
the second removal section includes:
a second summer configured to sum the second source signal and a harmonic signal having the same frequency as a removal target harmonic among the plurality of harmonics in the second source signal to output a second summed signal;
a harmonic generator configured to generate the harmonic signal that is summed with the second source signal;
a second Fourier transformer configured to input therein a second measurement signal in digital form output from the detector and calculate a plurality of harmonics included in the second measurement signal, the second measurement signal in digital form being output by the detector based on the second summed signal in analog form detected by the detector; and
a second controller configured to cause the harmonic generator to adjust either or both of an amplitude and a phase of the harmonic signal that is summed with the second source signal so that a harmonic that matches the removal target harmonic in the second source signal is removed.

11. The measuring device according to claim 10, further comprising
the measuring instrument, wherein
the measuring instrument includes:
the detector;
a phase difference calculating section configured to calculate a phase difference between a fundamental in the first measurement signal and a fundamental in the second measurement signal; and
a second ratio calculating section configured to calculate a value of a ratio of the second physical quantity to the first physical quantity based on the phase difference.

12. The measuring device according to claim 11, wherein
the measuring instrument further includes a delay difference calculating section configured to calculate a delay time difference between the first measurement signal and the second measurement signal, and the second ratio calculating section calculates the value of the ratio in accordance with an equation (2), $$r = \frac{p2 - pr}{p1 - pr} = \tan\left(\frac{\pi}{4} + \Delta\theta + \frac{2\pi f \Delta\tau}{2}\right) \quad (2)$$

where r represents the value of the ratio,
p1 represents the first physical quantity,
p2 represents the second physical quantity,
pr represents a reference physical quantity,
$\Delta\theta$ represents the phase difference,
f represents a frequency of the fundamental in the first measurement signal, and
$\Delta\tau$ represents the delay time difference.

13. The measuring device according to claim 11, having a non-linearity error measurement mode including a first mode and a second mode, wherein
in each of the first mode and the second mode, the first signal generator generates the first source signal in which the first physical quantity is maintained at a constant level and the second physical quantity is changed in a stepwise manner,
in each of the first mode and the second mode, the second signal generator generates the second source signal in which the first physical quantity is maintained at the constant level and the second physical quantity is changed in a stepwise manner,
in the first mode, the first summer sums the harmonic signal and the first source signal to output the first summed signal, and the detector outputs the first measurement signal from which the harmonic has been removed,
in the first mode, the second summer sums the harmonic signal and the second source signal to output the second summed signal, and the detector outputs the second measurement signal from which the harmonic has been removed,
in the first mode, the second ratio calculating section calculates the value of the ratio for each second physical quantity based on the first measurement signal from which the harmonic has been removed and the second measurement signal from which the harmonic has been removed,
in the second mode, the first summer outputs the first source signal as the first summed signal without summing the harmonic signal and the first source signal, and the detector outputs the first measurement signal from which none of the harmonics has been removed,
in the second mode, the second summer outputs the second source signal as the second summed signal without summing the harmonic signal and the second source signal, and the detector outputs the second measurement signal from which none of the harmonics has been removed,
in the second mode, the second ratio calculating section calculates the value of the ratio for each second physical quantity based on the first measurement signal from which none of the harmonics has been removed and the second measurement signal from which none of the harmonics has been removed, and
the measuring instrument further includes:
a second difference calculating section configured to calculate a difference between the value of the ratio calculated in the first mode and the value of the ratio calculated in the second mode for each second physical quantity; and
a storage configured to store therein the difference in association with the value of the ratio calculated in the second mode for each second physical quantity.

14. The measuring device according to claim 13, wherein the measuring instrument further includes:
a third ratio calculating section configured to calculate a value of a ratio of a fourth physical quantity to a third physical quantity; and
a correction section configured to correct the value of the ratio calculated by the third ratio calculating section based on the difference stored in the storage.

15. A measuring method comprising:
generating, by a signal generator, a first source signal including a fundamental and a plurality of harmonics based on a first physical quantity and a second physical quantity; and
removing, by a removing section, some or all of the plurality of harmonics from the first source signal to reduce influence of non-linearity of a detector of a measuring instrument, wherein
the removing includes:
summing, by a summer, the first source signal and a harmonic signal having the same frequency as a removal target harmonic among the plurality of harmonics to output a first summed signal;
inputting, by a Fourier transformer, therein a first measurement signal in digital form output from the detector and calculating a plurality of harmonics included in the first measurement signal through Fourier transform, the first measurement signal in digital form being output by the detector based on the first summed signal in analog form detected by the detector; and
adjusting, by a controller, either or both of an amplitude and a phase of the harmonic signal so that a harmonic that matches the removal target harmonic is removed from the first measurement signal,
the measuring method is applied to voltage measurement, optical measurement, current measurement, acoustic measurement, or vibration measurement,
when the measuring method is applied to the voltage measurement, each of the first physical quantity and the second physical quantity is a voltage, and each of the first source signal, the harmonic signal, the first summed signal, and the first measurement signal is an electric signal,
when the measuring method is applied to the optical measurement, each of the first physical quantity and the second physical quantity is an optical intensity, each of the first source signal, the harmonic signal, and the first summed signal is an optical signal, and the first measurement signal is an electric signal,
when the measuring method is applied to the current measurement, each of the first physical quantity and the second physical quantity is an electric current, and each of the first source signal, the harmonic signal, the first summed signal, and the first measurement signal is an electric signal,
when the measuring method is applied to the acoustic measurement, each of the first physical quantity and the second physical quantity is an acoustic pressure, each of the first source signal, the harmonic signal, and the first summed signal is an acoustic wave, and the first measurement signal is an electric signal, and when the measuring method is applied to the vibration measurement, each of the first physical quantity and the second physical quantity is an elastic wave displacement, each of the first source signal, the harmonic signal, and the first summed signal is an elastic wave, and the first measurement signal is an electric signal.

* * * * *